US012642860B2

(12) United States Patent
Cui et al.

(10) Patent No.: US 12,642,860 B2
(45) Date of Patent: Jun. 2, 2026

(54) FILAMENTOUS NANOSTRUCTURES AND THEIR USE FOR TREATMENT OF PULMONARY DISEASE

(71) Applicant: THE JOHNS HOPKINS UNIVERSITY, Baltimore, MD (US)

(72) Inventors: Honggang Cui, Lutherville, MD (US); Caleb French Anderson, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1074 days.

(21) Appl. No.: 17/770,826

(22) PCT Filed: Oct. 21, 2020

(86) PCT No.: PCT/US2020/056560
§ 371 (c)(1),
(2) Date: Apr. 21, 2022

(87) PCT Pub. No.: WO2021/081023
PCT Pub. Date: Apr. 29, 2021

(65) Prior Publication Data

US 2023/0127524 A1 Apr. 27, 2023

Related U.S. Application Data

(60) Provisional application No. 62/924,735, filed on Oct. 23, 2019.

(51) Int. Cl.

| | |
|---|---|
| ***A61K 47/65*** | (2017.01) |
| ***A61K 9/00*** | (2006.01) |
| ***A61K 9/12*** | (2006.01) |
| ***A61K 47/42*** | (2017.01) |

(52) U.S. Cl.
CPC ............ *A61K 47/65* (2017.08); *A61K 9/0092* (2013.01); *A61K 9/12* (2013.01); *A61K 47/42* (2013.01)

(58) Field of Classification Search
None
See application file for complete search history.

(56) References Cited

U.S. PATENT DOCUMENTS

| | | | | |
|---|---|---|---|---|
| 2002/0192780 A1* | 12/2002 | Sohn | C07K 5/1024 530/388.26 |
| 2008/0175892 A1* | 7/2008 | Wilson | B82Y 5/00 977/734 |
| 2011/0294952 A1 | 12/2011 | Petersen | |
| 2014/0113875 A1* | 4/2014 | Cui | A61K 47/551 514/21.7 |

FOREIGN PATENT DOCUMENTS

| | | |
|---|---|---|
| EP | 0324659 A2 | 7/1989 |
| WO | WO 2002/085927 | 10/2002 |

OTHER PUBLICATIONS

International Search Report and Written Opinion for PCT/US2020/056560. Mailed Feb. 1, 2021. 10 pages.
Acar et al., Cathepsin-Mediated Cleavage of Peptides from Peptide Amphiphiles Leads to Enhanced Intracellular Peptide Accumulation. Bioconjug Chem. Sep. 20, 2017;28(9):2316-2326.
Accardo et al., Nanostructures by self-assembling peptide amphiphile as potential selective drug carriers. Biopolymers. 2007;88(2):115-21.
Adjei et al., Pulmonary Delivery of Therapeutic Peptides and Proteins. J. Control. Release 1994, 29, 361-373.
Altunbas et al., Encapsulation of curcumin in self-assembling peptide hydrogels as injectable drug delivery vehicles. Biomaterials. Sep. 2011;32(25):5906-14.
Aulisa et al., Self-assembly of multidomain peptides: sequence variation allows control over cross-linking and viscoelasticity. Biomacromolecules. Sep. 14, 2009;10(9):2694-8.
Beniash et al., Self-assembling peptide amphiphile nanofiber matrices for cell entrapment. Acta Biomater. Jul. 2005;1(4):387-97.
Berndt et al., Synthetic Lipidation of Peptides and Amino Acids: Monolayer Structure and Properties. J. Am. Chem. Soc. 1995, 117, 9515-9522.
Black et al., Self-assembled peptide amphiphile micelles containing a cytotoxic T-cell epitope promote a protective immune response in vivo. Adv Mater. Jul. 24, 2012;24(28):3845-9.
Boylan et al., Highly compacted DNA nanoparticles with low MW PEG coatings: in vitro, ex vivo and in vivo evaluation. J Control Release. Jan. 10, 2012;157(1):72-9.
Carvalho et al., The function and performance of aqueous aerosol devices for inhalation therapy. J Pharm Pharmacol. May 2016; 68(5):556-78.
Chakrabartty et al., Aromatic side-chain contribution to far-ultraviolet circular dichroism of helical peptides and its effect on measurement of helix propensities. Biochemistry. Jun. 1, 1993;32(21):5560-5.

(Continued)

*Primary Examiner* — Christina Bradley
(74) *Attorney, Agent, or Firm* — Casimir Jones, SC; Thomas A. Isenbarger

(57) ABSTRACT

The present invention provides supramolecular filament and/or sphere compositions and their use as inhalable drug carriers within aerosols. The invention provides insights into peptide designs and supramolecular stability and its crucial role in the interfacial stability and aerosolization properties of the supramolecular filament and/or sphere compositions. The compositions and their properties show that molecular enrichment at the air-liquid interface during nebulization is the primary factor to deplete the monomeric peptide amphiphiles in solution, accounting for the observed morphological disruption/transitions. Importantly, encapsulation of drugs and dyes within the inventive filament and/or sphere compositions notably stabilize their supramolecular structure during nebulization, and the loaded filaments exhibit a linear release profile from a nebulizer device. The compositions disclosed herein can be used as an effective platform for the inhalation-based treatment of many lung and sinusoidal diseases.

8 Claims, 32 Drawing Sheets

Specification includes a Sequence Listing.

(56) References Cited

OTHER PUBLICATIONS

Champion et al., Shape induced inhibition of phagocytosis of polymer particles. Pharm Res. Jan. 2009;26(1):244-9.
Champion et al., Role of target geometry in phagocytosis. Proc Natl Acad Sci U S A. Mar. 28, 2006;103(13):4930-4.
Chan et al., Fmoc Solid Phase Synthesis A Practical Approach, Oxford University Press, 2000. TOC only. 9 pages.
Cheetham et al., Supramolecular nanostructures formed by anticancer drug assembly. J Am Chem Soc. Feb. 27, 2013;135(8):2907-10.
Chen et al., Self-Repair of Structure and Bioactivity in a Supramolecular Nanostructure. Nano Lett. Nov. 14, 2018;18(11):6832-6841.
Choi et al., Rapid translocation of nanoparticles from the lung airspaces to the body. Nat Biotechnol. Dec. 2010;28(12):1300-3.
Chung et al., Fibrin-binding, peptide amphiphile micelles for targeting glioblastoma. Biomaterials. Jan. 2014;35(4):1249-56.
Cui et al., Self-assembly of peptide amphiphiles: from molecules to nanostructures to biomaterials. Biopolymers. 2010;94(1):1-18.
Da Silva et al., DNA nanoparticle-mediated thymulin gene therapy prevents airway remodeling in experimental allergic asthma. J Control Release. Apr. 28, 2014:180:125-33.
Da Silva et al., Super-resolution microscopy reveals structural diversity in molecular exchange among peptide amphiphile nanofibre. Nat Commun. May 19, 2016:7:11561. 1-10.
Dankers et al., A modular and supramolecular approach to bioactive scaffolds for tissue engineering. Nat Mater. Jul. 2005;4(7):568-74.
Dega-Szafran et al., Synthesis, IR and NMR studies of zwitterionic ω-(1-pyrrolidine)alkanocarboxylic acids and their N-methyl derivatives. J Mol Struc. 1997, 436-7, 107-121.
Edwards et al., Large Porous Particles for Pulmonary Drug Delivery. Science (80-. ). 1997, 276, 1868-1872.
Fasman ed., Practical Handbook of Biochemistry and Molecular Biology, CRC Press, Inc. 2018. TOC only. 21 pages.
Feng et al., Enzymatic Assemblies Disrupt the Membrane and Target Endoplasmic Reticulum for Selective Cancer Cell Death. J. Am. Chem. Soc. 2018, 140, 9566-9573.
Feng et al., Self-Assembling Ability Determines the Activity of Enzyme-Instructed Self-Assembly for Inhibiting Cancer Cells. J. Am. Chem. Soc. 2017, 139, 15377-15384.
Fieser and Fieser's Reagents for Organic Synthesis, vols. 1-17, John Wiley and Sons, New York, N.Y., 1991; TOC only. 54 pages.
Frederix et al., Exploring the sequence space for (tri-)peptide self-assembly to design and discover new hydrogels. Nat Chem. Jan. 2015;7(1):30-7.
Gao et al., Imaging Enzyme-Triggered Self-Assembly of Small Molecules inside Live Cells. Nat. Commun. 2012, 1, 1033-1038.
Garbuzenko et al., Inhibition of lung tumor growth by complex pulmonary delivery of drugs with oligonucleotides as suppressors of cellular resistance. Proc Natl Acad Sci U S A. Jun. 8, 2010;107(23):10737-42.
Garbuzenko et al., Intratracheal versus Intravenous Liposomal Delivery of SiRNA, Antisense Oligonucleotides and Anticancer Drug. Pharm. Res. 2009, 26(2), 382-394.
Garbuzenko et al., Biodegradable Janus Nanoparticles for Local Pulmonary Delivery of Hydrophilic and Hydrophobic Molecules to the Lungs. Langmuir. Nov. 4, 2014;30(43):12941-9.
Garbuzenko et al., Inhalation Treatment of Lung Cancer: The Influence of Composition, Size and Shape of Nanocarriers on Their Lung Accumulation and Retention. Cancer Biol Med 2014, 11(1), 44-55.
Geng et al., Shape effects of filaments versus spherical particles in flow and drug delivery. Nat Nanotechnol. Apr. 2007;2(4):249-55.
Goodman & Gilman's The Pharmacological Basis of Therapeutics. McGraw-Hill Educaiton. 2018. TOC only. 6 pages.
Grant (Ed.) Synthetic Peptides A User's Guide 2nd Ed., Oxford University Press, 2002, TOC only. 4 pages.
Gratton et al., The effect of particle design on cellular internalization pathways. Proc Natl Acad Sci U S A. Aug. 19, 2008;105(33):11613-8.
Guler et al., Encapsulation of Pyrene within Self-Assembled Peptide Amphiphile Nanofibers. J. Mater. Chem. 2005, 15, 4507-4512.
Haines-Butterick et al., Controlling hydrogelation kinetics by peptide design for three-dimensional encapsulation and injectable delivery of cells. Proc Natl Acad Sci U S A. May 8, 2007;104(19):7791-6.
Hartgerink et al., Peptide-amphiphile nanofibers: a versatile scaffold for the preparation of self-assembling materials. Proc Natl Acad Sci U S A. Apr. 16, 2002;99(8):5133-8.
Hartgerink et al., Self-assembly and mineralization of peptide-amphiphile nanofibers. Science. Nov. 23, 2001;294(5547):1684-8.
Herbst et al., Self-healing polymers via supramolecular forces. Macromol Rapid Commun. Feb. 12, 2013;34(3):203-20.
Hertel et al., Protein stability in pulmonary drug delivery via nebulization. Adv Drug Deliv Rev. Oct. 1, 2015:93:79-94.
Hu et al., Electrostatic-Driven Lamination and Untwisting of β-Sheet Assemblies. ACS Nano. Jan. 26, 2016;10(1):880-8.
Jayawarna et al., Nanostructured Hydrogels for Three-Dimensional Cell Culture through Self-Assembly of Fluorenylmethoxycarbonyl-Dipeptides. Adv. Mater. 2006, 18, 611-614.
Krittanai et al., Correcting the circular dichroism spectra of peptides for contributions of absorbing side chains. Anal Biochem. Nov. 1, 1997;253(1):57-64.
Kuzmov et al., Nanotechnology approaches for inhalation treatment of lung diseases. J Control Release. Dec. 10, 2015:219:500-518.
Lai et al., Rapid transport of large polymeric nanoparticles in fresh undiluted human mucus. Proc Natl Acad Sci U S A. Jan. 30, 2007;104(5):1482-7.
Larock: Comprehensive Organic Transformations, VCH Publishers, 1989. TOC only. 21 pages.
Lin et al., Isomeric control of the mechanical properties of supramolecular filament hydrogels. Biomater Sci. Dec. 19, 2018;6(1):216-224.
Lin et al., PH-Responsive Branched Peptide Amphiphile Hydrogel Designed for Applications in Regenerative Medicine with Potential as Injectable Tissue Scaffolds. J. Mater. Chem. 2012, 22, 19447-19454.
Lock et al., Design and construction of supramolecular nanobeacons for enzyme detection. ACS Nano. Jun. 25, 2013;7(6):4924-32.
Lock et al., Tuning Cellular Uptake of Molecular Probes by Rational Design of Their Assembly into Supramolecular Nanoprobes. J Am Chem Soc. Mar. 16, 2016;138(10):3533-40.
Maa et al., Protein denaturation by combined effect of shear and air-liquid interface. Biotechnol Bioeng. Jun. 20, 1997;54(6):503-12.
Mahmud et al., Lung vascular targeting through inhalation delivery: insight from filamentous viruses and other shapes. IUBMB Life. Aug. 2011;63(8):607-12.
Mahmud et al., Spray stability of self-assembled filaments for delivery. J Control Release. Oct. 10, 2017:263:162-171.
Majumdar et al., Peptide-mediated targeted drug delivery. Med Res Rev. 2010. DOI 10.1002/med.20225. 1-22.
March, Advanced Organic Chemistry, John Wiley and Sons, New York, N.Y., 2007. TOC only. 6 pages.
Matson et al., Self-assembling peptide scaffolds for regenerative medicine. Chem Commun (Camb). Jan. 4, 2012;48(1):26-33.
Matsuda et al., Reaction of N-(Alkoxymethyl)dialkylamines and N, N'-Methylene-bisdialkylamines with Isocyanides. Chemical & Pharmaceutical Bulletin, 1975, 23(1), 219-221.
Mcomie. Protective Groups in Organic Chemistry, Plenum Press, New York, 1973. TOC only. 9 pages.
Merck Index. Merck & Co. Inc. 2001. TOC only 3 pages.
Mlinar et al., Active targeting of early and mid-stage atherosclerotic plaques using self-assembled peptide amphiphile micelles. Biomaterials. Oct. 2014;35(30):8678-86.
Moore et al., Nanofibrous peptide hydrogel elicits angiogenesis and neurogenesis without drugs, proteins, or cells. Biomaterials. Apr. 2018:161:154-163.
Organic Reactions, vols. 1-40, John Wiley and Sons, New York, N.Y., 1991; TOC only. 32 pages.
Otter et al., Supramolecular assembly of functional peptide-polymer conjugates. Org Biomol Chem. Jul. 17, 2019;17(28):6719-6734.
Pakalns et al., Cellular recognition of synthetic peptide amphiphiles in self-assembled monolayer films. Biomaterials. Dec. 1999;20(23-24):2265-79.

(56) References Cited

OTHER PUBLICATIONS

Paramonov et al., Self-assembly of peptide-amphiphile nanofibers: the roles of hydrogen bonding and amphiphilic packing. J Am Chem Soc. Jun. 7, 2006;128(22):7291-8.
Pashuck et al., Tuning supramolecular rigidity of peptide fibers through molecular structure. J Am Chem Soc. May 5, 2010;132(17):6041-6.
Pashuk et al., Direct observation of morphological transformation from twisted ribbons into helical ribbons. J Am Chem Soc. Jul. 7, 2010;132(26):8819-21.
Physicians' Desk Reference. PDR Network LLC. 2014. TOC only. 5 pages.
Rajangam et al., Heparin binding nanostructures to promote growth of blood vessels. Nano Lett. Sep. 2006;6(9):2086-90.
Rajangam et al., Peptide amphiphile nanostructure-heparin interactions and their relationship to bioactivity. Biomaterials. Aug. 2008;29(23):3298-305.
Rodd's Chemistry of Carbon Compounds, vols. 1-5 and supplements, Elsevier Science Publishers, 1991; TOC only. 8 pages.
Rubin et al., Emerging aerosol drug delivery strategies: from bench to clinic. Adv Drug Deliv Rev. Aug. 2014:75:141-8.
Rudra et al., A self-assembling peptide acting as an immune adjuvant. Proc Natl Acad Sci U S A. Jan. 12, 2010;107(2):622-7.
Sahoo et al., Aromatic Identity, Electronic Substitution, and Sequence in Amphiphilic Tripeptide Self-Assembly. Soft Matter. Nov. 21, 2018;14(45):9168-9174.
Si et al., Intranasal delivery of adjuvant-free peptide nanofibers elicits resident CD8+ T cell responses. J Control Release. Jul. 28, 2018:282:120-130.
Silva et al., Selective differentiation of neural progenitor cells by high- epitope density nanofibers. Science. Feb. 27, 2004;303(5662):1352-5.
Soukasene et al., Antitumor activity of peptide amphiphile nanofiber-encapsulated camptothecin. ACS Nano. Nov. 22, 2011;5(11):9113-21.
Sun et al., Sustained release of active chemotherapeutics from injectable-solid β-hairpin peptide hydrogel. Biomater Sci. May 26, 2016;4(5):839-48.
Tantakitti et al., Energy landscapes and functions of supramolecular systems. Nat Mater. Apr. 2016; 15(4):469-76.
Todoroff et al., Fate of Nanomedicines in the Lungs. Curr. Opin. Colloid Interface Sci. 2011, 16, 246-254.
Vongroning et al., Tuning the aqueous self-assembly of multistimuli-responsive polyanionic peptide nanorods. J Mater Chem B. Apr. 21, 2013;1(15):2008-2012.
Webber et al., Supramolecular biomaterials. Nat Mater. Jan. 2016;15(1):13-26.
Yang et al., Enzymatic Formation of Supramolecular Hydrogels. Adv. Mater. 2004, 16, 1440-1444.
Yang et al., Using a kinase/phosphatase switch to regulate a supramolecular hydrogel and forming the supramolecular hydrogel in vivo. J Am Chem Soc. Mar. 8, 2006;128(9):3038-43.
Yavvari et al., Sculpting Nanofibers of a Bolaamphiphilic Peptide through Sonication, and Quantifying Its Interaction with Anions. RSC Adv. 2013, 3, 17244-17253.
Yu et al., Self-Assembling Amphiphiles for Construction of Protein Molecular Architecture. J. Am. Chem. Soc. 1996, 118, 12515-12520.
Zhang et al., Self-assembled Tat nanofibers as effective drug carrier and transporter. ACS Nano. Jul. 23, 2013;7(7):5965-77.
Zhou et al., Self-assembled peptide-based hydrogels as scaffolds for anchorage-dependent cells. Biomaterials. May 2009;30(13):2523-30.

* cited by examiner

A

BUD-buSS-CVVVGGKVLDGQDP

B

C

D

FILAMENTOUS NANOSTRUCTURES AND THEIR USE FOR TREATMENT OF PULMONARY DISEASE

REFERENCE TO RELATED APPLICATIONS

This application is a § 371 National Phase Entry of International Application No. PCT/US2020/056560, filed on Oct. 21, 2020, which claims the benefit of U.S. Provisional Patent Application No. 62/924,735, filed on Oct. 23, 2019, which is hereby incorporated by reference for all purposes as if fully set forth herein.

STATEMENT OF GOVERNMENTAL INTEREST

This invention was made with government support under grant no. DMR 1255281 awarded by the National Science Foundation. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Oct. 7, 2020, is named P16006-02_ST25.txt and is 4,700 bytes in size.

BACKGROUND OF THE INVENTION

Filamentous nanomaterials have been extensively explored for the delivery of therapeutic and/or imaging agents, where their shape can aid in enhancing cellular internalization, extending circulation times, inducing cell death for disease treatment, and improve the therapeutic potential of inhalable materials. Nature's own filamentous carriers of proteins and genetic material, bacteria and viruses (like *Mycobacterium tuberculosis* and influenza), exhibit effective transport through the air in aerosols with enhanced deposition and retention within the lungs as afforded by their shape. In this sense, filamentous systems may provide the unique benefit of enhanced retention within the lungs through avoidance of their clearance mechanisms, like the mucociliary escalator and phagocytosis by alveolar macrophages, which could improve therapeutic efficacy and mitigate off-target effects compared to aerosolized small molecule drugs. This shape-promoted effect has been demonstrated by Hanes and colleagues, where pulmonary delivery of their polymeric rod-like DNA nanoparticles provided long-term relief of allergic asthma symptoms in mice with a single dose. This effect has also been manifested with peptide-based systems, where Collier and coworkers showcased that intranasal delivery of self-assembling influenza epitope-bearing peptide nanofibers elicited greater CD8+ T cell responses in mice for flu vaccination. Additionally, spray and nebulization stability has been assessed by those in the art for filomicelles formed from amphiphilic block copolymers, demonstrating their ability to maintain their structure and deliver loaded pesticides within aerosol droplets. These studies demonstrate the advantages of filamentous carriers for aerosol-based delivery, much like the filamentous microorganisms that inspired them.

Self-assembling peptides and peptide amphiphiles represent a class of molecular building units for filamentous nanomaterials whose assembly behavior into one-dimensional nanostructures has been extensively explored for the development of supramolecular biomaterials. These supramolecular systems have been used for a wide variety of biomedical applications, such as tissue engineering, regenerative medicine, molecular imaging, and drug delivery. The increasing popularity of peptide-based supramolecular systems is partially due to their high biocompatibility, facile synthesis, and easily tunable bioactivity and assembly properties. Though therapeutic peptides have been studied for pulmonary delivery within aerosols, the ability of peptide-based supramolecular nanostructures to travel within aerosols and the use of supramolecular filaments as inhalable carriers of therapeutic and imaging agents has yet to be studied. The distinct shape-afforded advantage of peptide amphiphiles could be potentially used to create filamentous carriers to enhance aerosol-based delivery. However, the most important aspect to consider is the stability of these filamentous assemblies, since mechanical forces present during aerosol formation may disrupt supramolecular structures due to the non-covalent nature of their assemblies.

SUMMARY OF THE INVENTION

In accordance with some embodiments, the present inventors have now designed and synthesized peptide amphiphile compositions with varying surface charges and supramolecular stabilities that all spontaneously associate in aqueous solutions to form supramolecular filament or sphere compositions capable of encapsulating disease-relevant compounds such as drugs and dyes, and report on one pioneering aspect of the invention for use as inhalable drug carriers within aerosols for use in lung diseases.

In some embodiments, loaded supramolecular filament or sphere compositions of the present invention are able to maintain their shape during aerosol formation using a jet nebulizer, and the stability of these systems within aerosols can be tuned through molecular engineering of the peptide units.

In some embodiments, drug-loaded supramolecular filament or sphere compositions with adjustable loading capacities can be emitted from a nebulizer as a respirable aerosol at a constant rate, allowing for a controlled and sustainable delivery as therapeutic aerosols.

In accordance with an embodiment, the supramolecular filament compositions of the present invention have the general formula: H-Pep-L-C(I), wherein H is a hydrophobic moiety or domain. The hydrophobic moiety can be, in some embodiments, an alkyl chain. The alkyl chain can be a chain having 8 to 22 carbons. In some embodiments, H can be a hydrophobic drug or biologically active agent.

Pep is a hydrogen bond-regulating moiety or domain. In some embodiments, the hydrogen bond-regulating moiety is a peptide sequence of 4 to 6 amino acids. In some embodiments, Pep is YVVV (SEQ ID NO: 1). L is a linker moiety or domain. In some embodiments, the linker is a peptide of 1-4 amino acids. In some embodiments there can be more than one linker in the molecule, such as H-L-Pep-L-C(II). The linkers can be the same or different.

C is a surface charge-regulating moiety or domain. In some embodiments, the surface charge-regulating moiety can have a positive, neutral, or negative surface charge. In some embodiments, the charge is due to 1 to 4 amino acids having a positive, neutral or negative charged side chain. In some embodiments, Pep-L-C can be considered together as the hydrophilic domain.

In some embodiments, the supramolecular filament or sphere compositions are capable of spontaneously assembling in aqueous solutions into supramolecular filaments.

In accordance with an embodiment, the present invention provides supramolecular filament or sphere compositions comprising one or more drug or biologically active agents which provide a sustained release local drug delivery system. The use of such compositions is not limited to local in situ release of one or more biologically active agents into the tissues in contact with the supramolecular filament composition.

In accordance with an embodiment, the present invention provides supramolecular filament or sphere compositions comprising one or more compounds for use in a spray or aerosol delivery, application or administration of said compounds.

In accordance with an embodiment, the present invention provides supramolecular filament or sphere compositions comprising one or more additional compositions for use in a spray or aerosol delivery, application or administration of said additional compositions.

In accordance with an embodiment, the present invention provides supramolecular filament or sphere compositions comprising one or more drug or biologically active agents for use in a spray or aerosol delivery or administration of said drug or biologically active agent.

In accordance with an embodiment, the present invention provides supramolecular filament or sphere compositions comprising one or more drug or biologically active agents for use in a spray or aerosol delivery, application or administration of said drug or biologically active agent to a tissue of a subject.

In accordance with an embodiment, the present invention provides a method of local administration of one or more supramolecular filament or sphere compositions comprising one or more drug or biologically active agents, and upon contact with body fluids the composition is capable of undergoing a change from solution state to nanofiber gelation state.

In accordance with an embodiment, the delivered supramolecular filament or sphere compositions can sustainably release the encapsulated bioactive agents over a long period of time.

In accordance with an embodiment, the supramolecular filament or sphere compositions enable diffusion across larger areas relative to individual molecules and avoids capillary loss.

BRIEF DESCRIPTION OF THE DRAWINGS

FIGS. 30A-30E: (30A) Chemical structure of budesonide-based drug amphiphile CAB-3, where molecular design is composed of hydrophobic drug budesonide (red) and a hydrophilic peptide, which contains an aromatic interaction-promoting sequence (blue) to promote formation of 1D nanostructures and an anti-inflammatory sequence (pink) to enhance anti-inflammatory efficacy. (30B) Analytical RP-HPLC chromatogram of CAB-3, showing high purity after synthesis. (30C) MALDI-TOF mass spectrum of purified CAB-3, confirming correct molecular weight. (30D) Representative transmission electron microscopy images of CAB-3 at 1 mM at pH 7.4 in water after aging for 24 hours, showing formation of supramolecular filaments. CGFFFGGDPVKG (SEQ ID NO: 19).

DETAILED DESCRIPTION OF THE INVENTION

Figures 1A, 1B:
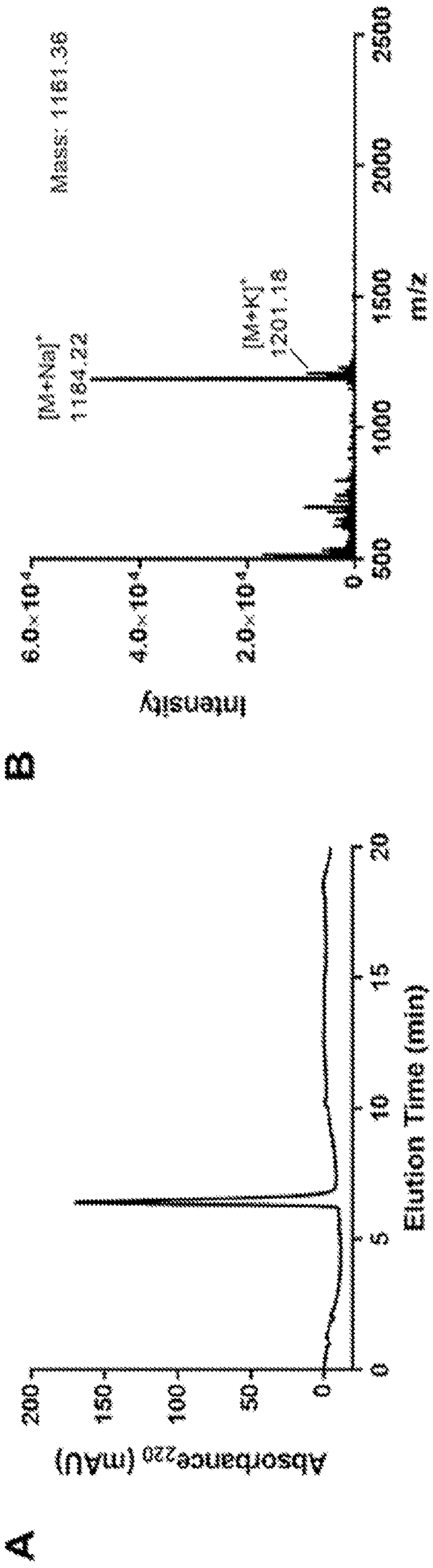
FIGS. 1A-1B depicts the (1A) Analytical RP-HPLC chromatogram and (1B) MALDI-TOF mass spectrum of EPA.

It is contemplated that the peptide-based supramolecular filaments and/or spheres of the present invention can be made in solid or liquid form, and then applied to the tissues of interest by spraying, aerosolizing, nebulizing, or otherwise applying the compositions directly to the tissues.

In some preferred embodiments, the compositions of the present invention can be prepared as a dry powder and then come into contact with aqueous solutions, for example, such as physiological buffers or tissue fluids such as blood or lymph, and will spontaneously form aqueous peptide-based supramolecular filaments or spheres.

In some embodiments, the biologically active agent or drug can act as the hydrophobic portion (H) of molecule in the nanofiber hydrogel compositions of the present invention.

In some embodiments, the H region could also be a hydrophobic drug or other therapeutic moiety or biologically active agent other than an alkyl chain.

In some embodiments, Pep-L-C can more broadly be categorized as a hydrophilic domain. The order of these segments can vary. Furthermore, the hydrophilic domain can have a bioactive or therapeutic moiety at the end to present these on the supramolecular structure's surface. Moreover, Pep-L-C can also be composed of nucleic acids or polymer chains. The L segment can also come in between H and Pep as a biodegradable linker to release the H from the molecule after responding to various environmental factors (like hydrolysis, redox potential, pH, etc.). This can also be true for the case of a L segment separating a hydrophilic therapeutic or bioactive moiety from the rest of the molecule. For a given design, the Pep, L, or C sections could also be missing and the designed molecule may still form supramolecular structures.

The hydrophobic moiety can be, in some embodiments, an alkyl chain. The alkyl chain can be a chain having 8 to 22 carbons. In some embodiments, H is a $C_{12}$ alkyl chain.

It is contemplated that the other hydrophobic molecules can be used in the hydrophobic (H) moiety of the present invention. For example, other hydrophobic molecules such as steroids, other conjugated ring containing molecules, and hydrophobic drugs or imaging agents can be used.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls," the latter of which refers to alkyl moieties having substituents replacing hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $—CF_3$, —CN and the like. Exemplary substituted alkyls are described below. Cycloalkyls may be further substituted with alkyls, alkenyls, alkoxys, alkylthios, aminoalkyls, carbonyl-substituted alkyls, $—CF_3$, —CN and the like.

As used herein, the term "hydrophobic" biologically active agents or drug molecules describes a heterogeneous group of molecules that exhibit poor solubility in water but that are typically, but certainly not always, soluble in various organic solvents. Often, the terms slightly soluble (1-10 mg/ml), very slightly soluble (0.1-1 mg/ml), and practically insoluble (<0.1 mg/ml) are used to categorize such substances. Drugs such as steroids and many anticancer drugs are important classes of poorly water-soluble drugs; however, their water solubility varies over at least two orders of magnitudes. Typically, such molecules require secondary solubilizers such as carrier molecules, liposomes, polymers, or macrocyclic molecules such as cyclodextrins to help the hydrophobic drug molecules dissolve in aqueous solutions necessary for drug delivery in vivo. Other types of hydrophobic drugs show even a lower aqueous solubility of only a few ng/ml. Since insufficient solubility commonly accompanies undesired pharmacokinetic properties, the high-throughput screening of kinetic and thermodynamic solubility as well as the prediction of solubility is of major importance in discovery (lead identification and optimization) and development.

Examples of hydrophobic moieties that can be used in accordance with the present invention include long chain fatty acids, such a stearate, and/or palmitate.

As used herein, the linker (L) moiety or domain can be 1-4 amino acids which may independently be the same or different. Preferably the amino acids are small and neutral. In one embodiment, for example, the L moiety or domain was a diglycine peptide. Other amino acids can also be used, such as, for example, alanine, serine or threonine.

In some other embodiments, L is 0 to 4 biodegradable linkers. The linker can be an ester bond, amide bond, carbonate bond, hydrozone, disulfide bond, or any amino acid with a side chain having a free amino, carboxyl or thiol group, or a short peptide that can be specifically cleaved by a particular enzyme or proteinase. In an embodiment, the linker can be a $C_1$-$C_6$ acyl-disulfide group. For example, the linker can be (4-(pyridin-2-yldisulfanyl) butanoate) (buSS).

The buSS linker has a disulfide moiety that allows it to be reductively cleaved primarily intracellularly by glutathione. In particular, the concentration of glutathione inside tumor cells is 100 to 1000 times higher than in the interstitial fluid, thus allowing the compositions of the present invention to act as a prodrug and enter the cell intact. Once inside the cell, the reduction of the linker bonds by glutathione occurs, and the free hydrophobic drug molecule can act on its target. It will be understood by those of ordinary skill in the art that other linker moieties can be used where they interact with the hydrophilic peptide in a similar manner.

In another embodiment, the linker can be the buSS analog, (4-pyridyldisulfanyl)ethyl carbonate (etcSS), which also can be reductively cleaved primarily intracellularly by glutathione.

Pep is a hydrogen bond-regulating moiety or domain. In some embodiments, Pep is a peptide composition having the amino acid sequence Bn, wherein Bn is an amino acid, of n=4 to 12 amino acids, which can be the same or different, and which can have biologically relevant properties including, but not limited to, tumor targeting, tissue penetrating, cell penetrating, apoptotic or capable of binding to known cellular epitopes, such as integrins or cancer cell receptors, and derivatives, or functional fragments or functional homolog of such peptides. In some embodiments, Pep can include anti-inflammatory peptides such as KVLDPVKG (SEQ ID NO: 14), and/or KVLDGQDP (SEQ ID NO: 8) and/or DPVKG (SEQ ID NO: 15) which block phospholipase $A_2$ ($PLA_2$) and transglutaminase which is reported in WO2002085927 and incorporated by reference herein. In some embodiments, Pep is hydrophilic. In other embodiments, Pep can act as a linker L.

In some embodiments, Pep comprises 4, 5, 6, 7, 8, 9, 10, 11, up to 12 amino acids.

The term, "amino acid" includes the residues of the natural α-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and non-natural amino acids. Many types of amino acid residues are useful in the polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

Reference herein to "derivatives" includes parts, fragments and portions of the Pep portion of the molecule. A derivative also includes a single or multiple amino acid substitution, deletion and/or addition. Homologues include functionally, structurally or stereochemically similar peptides from the naturally occurring peptide or protein. All such homologs are contemplated by the present invention.

Analogs and mimetics include molecules which include molecules which contain non-naturally occurring amino acids or which do not contain amino acids but nevertheless behave functionally the same as the peptide. Natural product screening is one useful strategy for identifying analogs and mimetics.

Examples of incorporating non-natural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, omithine, sarcosine, 4-amino-3-hydroxy-6-methylheptanoic acid, 2-thienyl alanine and/or D-isomers of amino acids. A partial list of known non-natural amino acid contemplated herein is shown in Table 1.

TABLE 1

| Non-natural Amino Acids | | | |
|---|---|---|---|
| Non-conventional amino acid | Code | Non-conventional amino acid | Code |
| α-aminobutyric acid | Abu | L-N-methylalanine | Nmala |
| α-amino-a-methylbutyrate | Mgabu | L-N-methylarginine | Nmarg |
| aminocyclopropane- | Cpro | L-N-methylasparagine | Nmasn |
| carboxylate | | L-N-methylaspartic acid | Nmasp |
| aminoisobutyric acid | Aib | L-N-methylcysteine | Nmcys |
| aminonorbomyl- | Norb | L-N-methylglutamine | Nmgln |
| carboxylate | | L-N-methylglutamic acid | Nmglu |
| cyclohexylalanine | | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |

TABLE 1-continued

| Non-natural Amino Acids | | | |
|---|---|---|---|
| Non-conventional amino acid | Code | Non-conventional amino acid | Code |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Analogs of the peptide-based supramolecular filaments contemplated herein include modifications to side chains, incorporation of non-natural amino acids and/or their derivatives during peptide synthesis and the use of crosslinkers and other methods which impose conformational constraints on the peptide molecule or their analogs.

Examples of side chain modifications contemplated by the peptide-based supramolecular filaments present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates small chemical analogs of the naturally occurring Pep moiety. Chemical analogs may not necessarily be derived from the peptides themselves but may share certain conformational similarities. Alternatively, chemical analogs may be specifically designed to mimic certain physiochemical properties of the peptides. Chemical analogs may be chemically synthesized or may be detected following, for example, natural product screening.

In some embodiments, the surface charge-regulating moiety or domain (C) can have a positive, neutral or negative surface charge. In some embodiments, the charge is due to 1 to 4 amino acids having a positive, neutral or negative charged side chain. For example, Arg, His, or Lys can be used for positively charged side chains ($NH_3$), Asp and Glu for negatively charged side chains (COOH), and various amino acids like Ser, Thr for uncharged or neutral side chains. In some other embodiments, the neutral side chains can be polar hydrophilic molecule, such as a polyethylene oxide (PEO), conjugated to an amino acid side chain. In one embodiment, the neutral surface charge-regulating moiety or domain comprises two Lys residues having the terminal ammonia moiety conjugated to PEO via an amide bond to the carboxyl group of the PEO molecules. In other embodiments, other biologically compatible polymers such as, for example, other hydrophilic polymers like hydrolyzed poly (vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, hydroxyalkylated celluloses such as hydroxyethyl cellulose and methylhydroxypropyl cellulose, oligosaccharides, cyclodextrins, ligands, and epitopes can be used.

In the following embodiments, the supramolecular filament compositions are capable of spontaneously assembling in aqueous solutions into supramolecular filaments.

In accordance with an embodiment, the present invention provides an embodiment of the peptide-based supramolecular filament having the general formula: H-Pep-L-C(I), having the following structure:

(III)

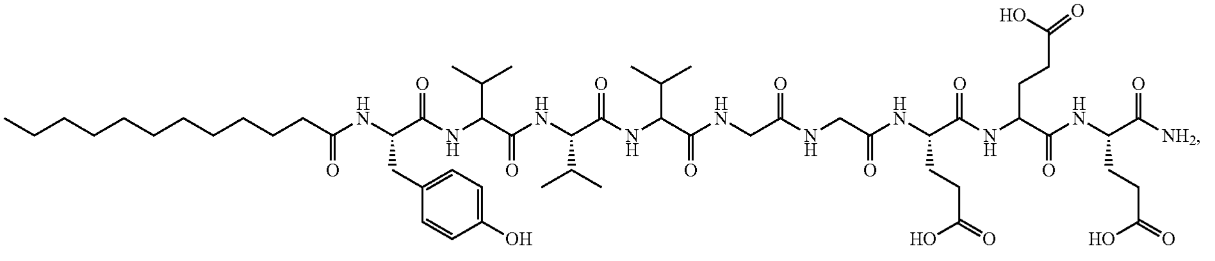

wherein His $C_{12}$ alkyl, Pep is YVVV (SEQ ID NO: 1), L is GG, and C is EEE. The supramolecular filament has a negative charge in aqueous solutions due to the glutamic acids at the C domain of the molecule. In another aspect, the supramolecular filament of formula II has the peptide sequence of YVVVGGEEE (SEQ ID NO: 2).

In accordance with another embodiment, the present invention provides an embodiment of the peptide-based supramolecular filament having the general formula: H-Pep-L-C(I), having the following structure:

(IV)

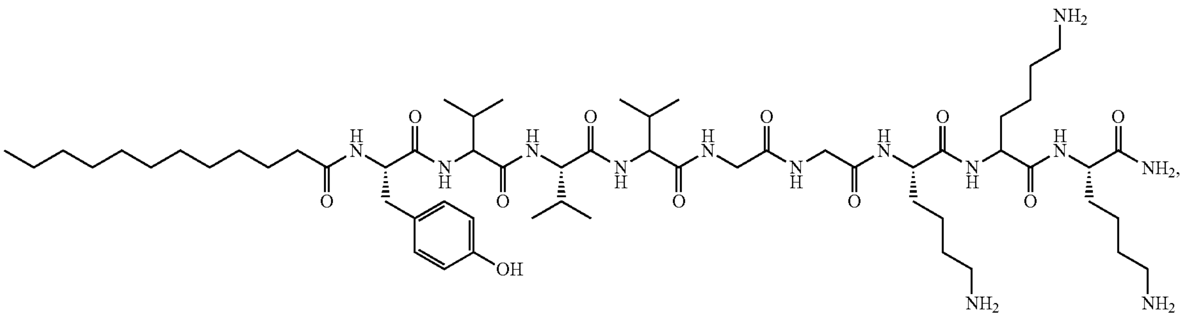

wherein H is $C_{12}$ alkyl, Pep is YVVV (SEQ ID NO: 1), L is GG, and C is KKK. The supramolecular filament has a positive charge in aqueous solutions due to the three lysine residues at the C domain of the molecule. In another aspect, the supramolecular filament of formula IV has the peptide sequence of YVVVGGKKK (SEQ ID NO: 3).

In accordance with a further embodiment, the present invention provides an embodiment of the peptide-based supramolecular filament having the general formula: H-Pep-L-C(I), having the following structure:

(V)

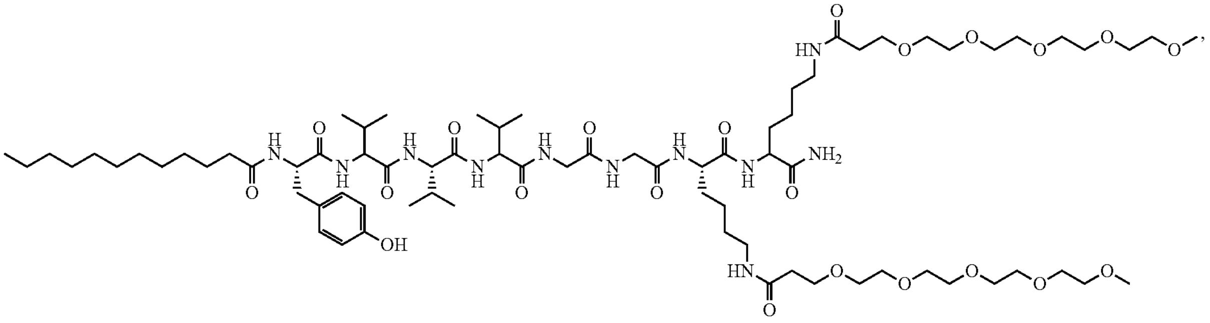

wherein H is $C_{12}$ alkyl, Pep is YVVV (SEQ ID NO: 1), L is GG, and C is (K-OEG) 2. The supramolecular filament has a neutral charge in aqueous solutions due to the two lysine residues covalently linked at the amino side chain due to an oligo (ethylene glycol) molecule at the C domain of the molecule. In another aspect, the supramolecular filament of formula III has the peptide sequence of YVVVGGKK (SEQ ID NO: 4).

In accordance with another embodiment the present invention provides an embodiment of the peptide-based supramolecular filament having the general formula: H-L-Pep-C(II), having the following structure (VI):

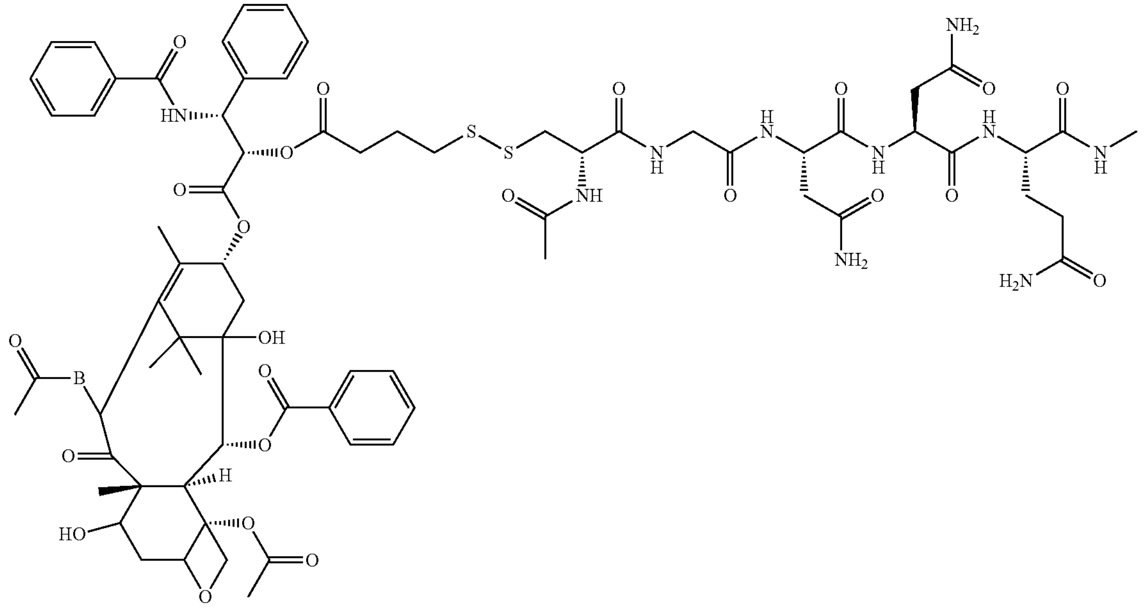

-continued (VI)

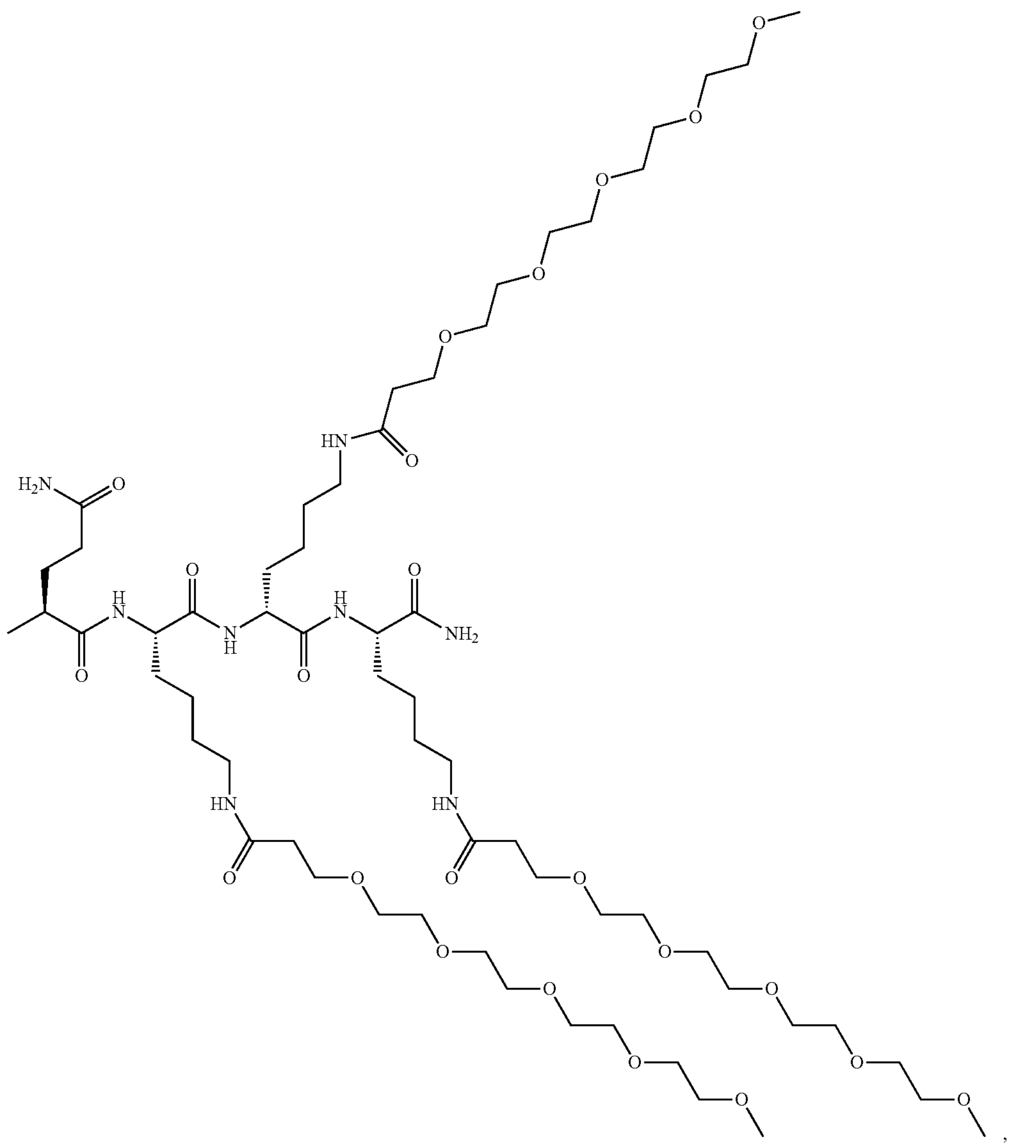

wherein H is paclitaxel conjugated to buSS, which is conjugated to Pep, L is buSS, Pep is CGNNQQ (SEQ ID NO: 5), and C is $(K\text{-}OEG)_3$. In another aspect, the supramolecular filament of formula VI has the peptide sequence of CGNNQQKKK (SEQ ID NO: 6).

In accordance with a further embodiment, the present invention provides an embodiment of the peptide-based supramolecular filament having the general formula: H-L-Pep-L-C(II), having the following structure (VII):

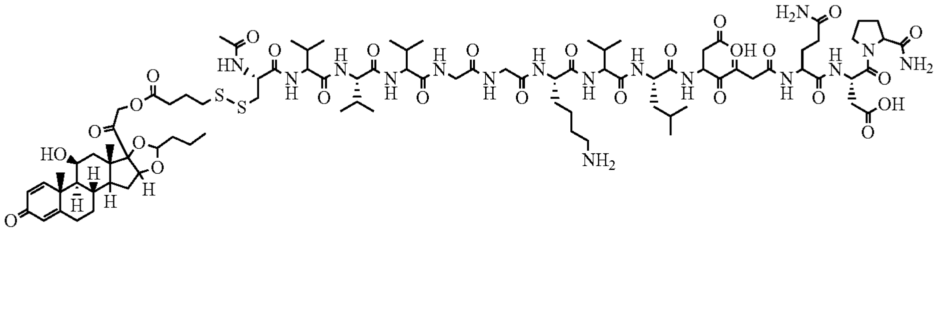

wherein H is budesonide conjugated to buSS, which is conjugated to Pep, L is buSS, Pep is CVVV (SEQ ID NO: 7), L is GG, and C is an anti-inflammatory peptide KVLDGQDP (SEQ ID NO: 8). In another aspect, the supramolecular filament of formula VII has the peptide sequence of CVVVGGKVLDGQDP (SEQ ID NO: 9).

In accordance with a further embodiment, the present invention provides an embodiment of the peptide-based supramolecular filament having the general formula: H-L-Pep-L-C(II), having the following structure (VIII):

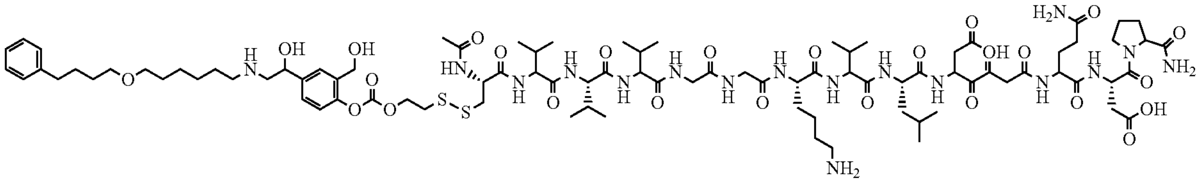

wherein H is salmeterol conjugated to etcSS, which is conjugated to Pep, L is etcSS, Pep is CVVV (SEQ ID NO: 7), L is GG, and C is an anti-inflammatory peptide KVLDGQDP (SEQ ID NO: 8). In another aspect, the supramolecular filament of formula IX has the peptide sequence of CVVVGGKVLDGQDP (SEQ ID NO: 9).

In accordance with a further embodiment, the present invention provides an embodiment of the peptide-based supramolecular filament having the general formula: H-L-Pep-L-C(II), having the following structure (IX):

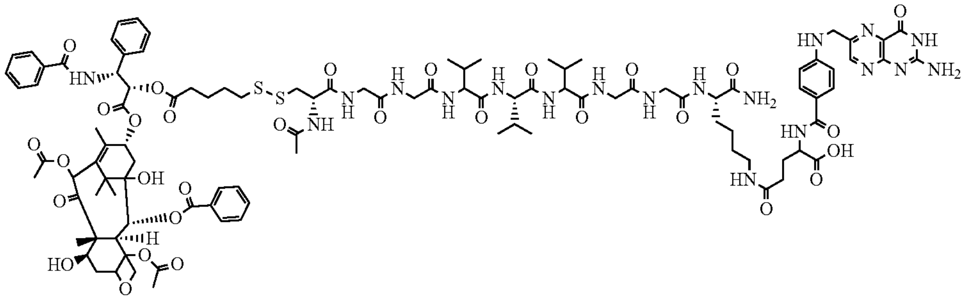

wherein H is paclitaxel conjugated to buSS, which is conjugated to Pep, L is buSS, Pep is CGGVVV (SEQ ID NO: 10), L is GG, and C is K conjugated to a folic acid molecule. In another aspect, the supramolecular filament of formula IX has the peptide sequence of

```
                                        (SEQ ID NO: 11)
          CGGVVVGGK.
```

In accordance with a further embodiment, the present invention provides an embodiment of the peptide-based supramolecular filament having the general formula: H-L-Pep-L-C(II), having the following structure (X):

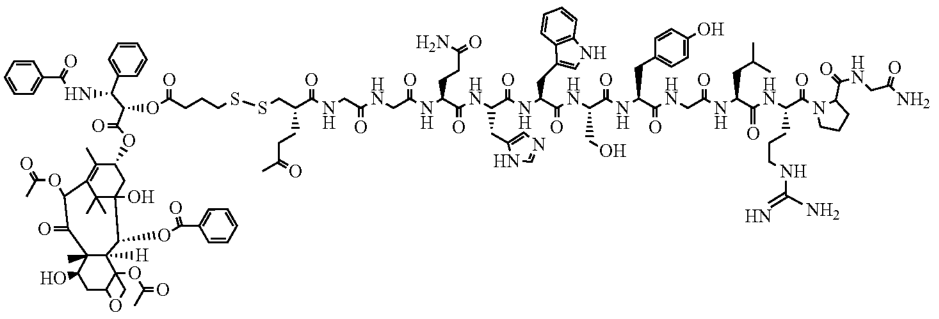

wherein H is paclitaxel conjugated to buSS, which is conjugated to Pep, L is buSS, Pep is interchangeable with L and is CGG, and C is an LHRH targeting peptide sequence QHWSYGLRPG (SEQ ID NO: 12). In another aspect, the supramolecular filament of formula X has the peptide sequence of CGGQHWSYGLRPG (SEQ ID NO: 13).

In accordance with an embodiment, the present invention provides an embodiment of the peptide-based supramolecular filament having the general formula: H-L-Pep-L-C(II), having the following structure:

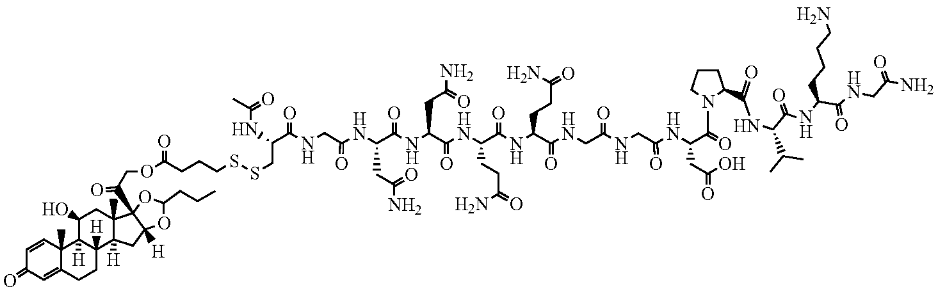

(XI) (CAB-1); wherein H is budesonide conjugated to buSS, which is conjugated to Pep, L is buSS, L is CG, Pep is NNQQ (SEQ ID NO: 16) L is GG and C is an anti-inflammatory peptide DPVKG (SEQ ID NO: 15). In another aspect, the supramolecular filament of formula XI has the peptide sequence of CGNNQQGGDPVKG (SEQ ID NO: 17).

In accordance with an embodiment, the present invention provides an embodiment of the peptide-based supramolecular filament having the general formula: H-L-Pep-L-C(II), having the following structure:

(XII) (CAB-2); wherein H is budesonide conjugated to buSS, which is conjugated to Pep, L is buSS, L is CG, Pep is VVV, L is GG and C is an anti-inflammatory peptide DPVKG (SEQ ID NO: 15). In another aspect, the supramolecular filament of formula XII has the peptide sequence of CGVVVGGDPVKG (SEQ ID NO: 18).

In accordance with an embodiment, the present invention provides an embodiment of the peptide-based supramolecular filament having the general formula: H-L-Pep-L-C(II), having the following structure:

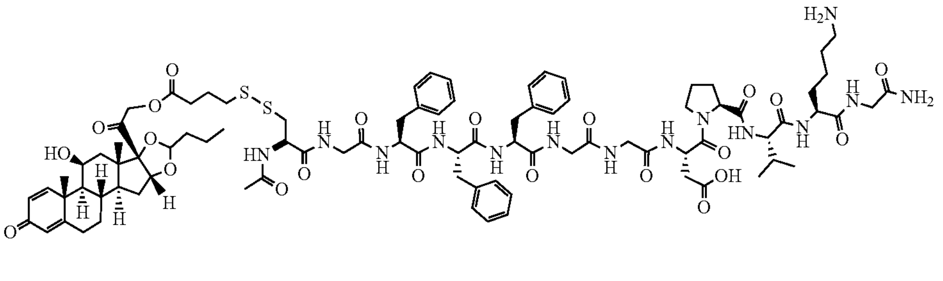

(XIII) (CAB-3); wherein H is budesonide conjugated to buSS, which is conjugated to Pep, L is buSS, L is CG, Pep is FFF, L is GG and C is an anti-inflammatory peptide DPVKG (SEQ ID NO: 15). In another aspect, the supramolecular filament of formula XIII has the peptide sequence of CGFFFGGDPVKG (SEQ ID NO: 19).

In accordance with an embodiment, the present invention provides an embodiment of the peptide-based supramolecular filament having the general formula: H-L-Pep-L-C(II), having the following structure:

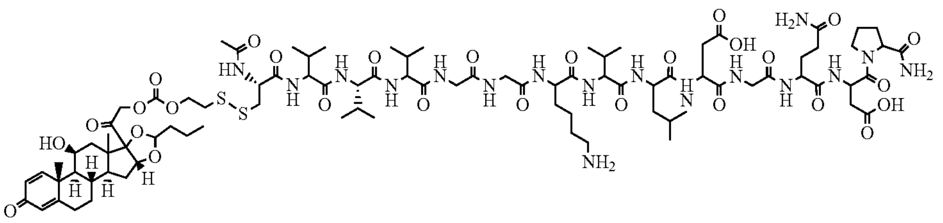

(XIV) (CAB-0); wherein H is budesonide conjugated to buSS, which is conjugated to Pep, L is buSS, L is C, Pep is VVV, L is GG, and C is an anti-inflammatory peptide KVLDGQDP (SEQ ID NO: 8). In another aspect, the supramolecular filament of formula XIV has the peptide sequence of CVVVGGKVLDGQDP (SEQ ID NO: 21).

In an alternative embodiment In accordance with an embodiment, the present invention provides an embodiment of the peptide-based supramolecular filament control having the general formula: H-L-Pep-L-C(II), having the following sequence: wherein H is budesonide conjugated to buSS, which is conjugated to Pep, L is buSS, L is CG, Pep is NNQQ (SEQ ID NO: 16) L is GG and K (OEG) 2. In another aspect, the supramolecular control filament has the peptide sequence of CGNNQQGGKK (SEQ ID NO: 22).

In some embodiments, the supramolecular filament compositions are capable of spontaneously assembling in aqueous solutions into supramolecular spheres.

In accordance with an embodiment, the present invention provides an embodiment of the peptide-based supramolecular sphere having the general formula: H-L-Pep-L-C(II), having the following structure:

(XV) (CAB-4); wherein H is budesonide conjugated to buSS, which is conjugated to Pep, L is buSS, L is CG, Pep is AAA, L is GG and C is an anti-inflammatory peptide DPVKG (SEQ ID NO: 15). In another aspect, the supramolecular sphere of formula XV has the peptide sequence of CGAAAGGDPVKG (SEQ ID NO: 20).

In an alternative embodiment In accordance with an embodiment, the present invention provides an embodiment of the peptide-based supramolecular sphere control having the general formula: H-L-Pep-L-C(II), having the following sequence: wherein H is budesonide conjugated to buSS, which is conjugated to Pep, L is buSS, L is CG, Pep is AAA Lis K (OEG) 3. In another aspect, the supramolecular control sphere has the peptide sequence of CGAAAKKK (SEQ ID NO: 22).

In accordance with an embodiment, the present invention provides supramolecular filament compositions comprising one or more drug or biologically active agents which provide a sustained release local drug delivery system. The use of such compositions is not limited to local in situ release of one or more biologically active agents into the tissues in contact with the supramolecular filament composition.

As used herein, the term "biologically active agent" include any compound, biologics for treating brain-related diseases, e.g. drugs, inhibitors, and proteins. An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: anti-neoplastics such as androgen inhibitors, antimetabolites, cytotoxic agents, and immunomodulators. More specifically, non-limiting examples of useful biologically active agents include the following therapeutic categories antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and *vinca* alkaloid natural antineoplastics, such as carboplatin and cisplatin; carmustine (BCNU); methotrexate; fluorouracil (5-FU) and gemcitabine; goserelin, leuprolide, and tamoxifen, aldesleukin, interleukin-2, docetaxel, etoposide, interferon; paclitaxel, other taxane derivatives, tretinoin (ATRA); bleomycin, dactinomycin, daunorubicin, doxorubicin, and mitomycin; vinblastine and vincristine.

As used herein, the term "biologically active agent" can also include imaging agents for use in identifying the location of the molecules in the tissues. In accordance with an embodiment, the imaging agent is a fluorescent dye. The dyes may be emitters in the visible or near-infrared (NIR) spectrum. Known dyes useful in the present invention include carbocyanine, indocarbocyanine, oxacarbocyanine, thüicarbocyanine and merocyanine, polymethine, coumarine, rhodamine, xanthene, fluorescein, boron~dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Organic dyes which are active in the NIR region are known in biomedical applications. However, there are only a few NIR dyes that are readily available due to the limitations of conventional dyes, such as poor hydrophilicity and photostability, low quantum yield, insufficient stability and low detection sensitivity in biological system, etc. Significant progress has been made on the recent development of NIR dyes (including cyanine dyes, squaraine, phthalocyanines, porphyrin derivatives and BODIPY (borondipyrromethane) analogues) with much improved chemical and photostability, high fluorescence intensity and long fluorescent life. Examples of NIR dyes include cyanine dyes (also called as polymethine cyanine dyes) are small organic molecules with two aromatic nitrogen-containing heterocycles linked by a polymethine bridge and include Cy5, Cy5.5, Cy7 and their derivatives. Squaraines (often called Squarylium dyes) consist of an oxocyclobutenolate core with aromatic or heterocyclic components at both ends of the molecules, an example is KSQ-4-H. Phthalocyanines, are two-dimensional 18π-electron aromatic porphyrin derivatives, consisting of four bridged pyrrole subunits linked together through nitrogen atoms. BODIPY (boron-dipyrromethane) dyes have a general structure of 4,4'-difluoro-4-bora-3a, 4a-diaza-s-indacene) and sharp fluorescence with high quantum yield and excellent thermal and photochemical stability.

Other imaging agents which are attached to the nanofiber hydrogel compositions of the present invention include PET and SPECT imaging agents. The most widely used agents include branched chelating agents such as di-ethylene triamine penta-acetic acid (DTPA), 1,4,7,10-tetra-azacyclododecane-1,4,7,10-tetraacetic acid (DOTA) and their analogs. Chelating agents, such as di-amine dithiols, activated mercaptoacetyl-glycyl-glycyl-gylcine (MAG3), and hydrazidonicotinamide (HYNIC), are able to chelate metals like $^{99m}$Tc and $^{186}$Re. Instead of using chelating agents, a prosthetic group such as N-succinimidyl-4-$^{18}$F-fluorobenzoate ($^{18}$F-SFB) is necessary for labeling peptides with $^{18}$F. In accordance with a preferred embodiment, the chelating agent is DOTA.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

In accordance with an embodiment, the present invention provides supramolecular filament compositions comprising one or more compounds for use in a spray or aerosol delivery, application or administration of said compounds.

In accordance with some embodiments, the present inventors now provide compositions comprising peptide-based supramolecular filaments, which are capable of being used as inhalable drug carriers within liquid aerosol droplets for use in pulmonary applications such as delivery to the lungs or sinuses. The several micron-long filaments formed by the self-assembly of peptide amphiphile compositions can travel within aerosol droplets, where nebulization reduces their contour length.

As used herein, the term "aerosol" or "aerosolization" means creating a liquid aerosol generated using a variety of means. In some embodiments, aerosolized filaments of the present invention can be generated using nebulizers. There are two main types of nebulizers available: the first and most common type is jet nebulizer that works based on changes in air pressure. The liquid formulation containing drug particles along with the compressed air within the inhaler chamber pass through a very narrow tube and enter a wide area; the increase in the volume of compressed air leads to reduction of its pressure and atomizes the liquid into micron size droplets. In order to catch large and non-inhalable particles there is a baffle within the nebulizer. Finally, small inhalable particles of drug will be sucked into the respiratory track to reach the site of action or the site of systemic absorption.

Another type of nebulizer utilizes ultrasonic power in order to produce micron-scaled inhalable particles; ultrasonic nebulizers break down the drug solution into small droplets via piezoelectric vibration. There is typically a baffle within the inhaler, as well as jet nebulizers, to remove large droplets and return them to the main chamber of device. A wide range of compressed air jet nebulizers have been characterized. Different units may be chosen based primarily on desired droplet particle size and concentration output. Ultrasonic nebulizers may also be used, particularly when high volumetric outputs are required. A significant concern for many nebulizers that have small liquid capacities is the increase in solute concentration that occurs over time as the reservoir volume is depleted with nebulization. This can lead to changes in concentration and particle size. This problem is often solved by using a feed system so that a constant level is maintained in the nebulizer reservoir for up to several hours of exposure. Another type of nebulizer which can be used is a vibrating mesh nebulizer.

Other embodiments for generating an inhaled aerosolized composition of the present invention include compressed air or inert gas inhalers or puff inhalers in which the inventive compositions are included and then inhaled when the container with the mixture is activated and the mixture is delivered when the compressed gas is released through a mouth piece and inhaled, such as used in asthma and COPD.

The formulation of drug solution is usually designed to optimize drug solubility and stability; small changes in formulation may also affect inhaled mass, particle size distribution, and treatment time. There are several advantages to jet nebulization, including the fact that effective use requires only simple, tidal breathing, and that dose modification and dose compounding are possible. Disadvantages include the duration of treatment time and equipment size.

Thus, in accordance with some embodiments, the present invention provides supramolecular filament compositions comprising one or more additional compositions for use in delivering drugs or biologically active agents to the interior of the lungs or nasal cavity of a subject.

In accordance with an alternative embodiment, the present invention provides peptide-based supramolecular filament compositions comprising one or more additional compositions for use in a spray or aerosol delivery, application or administration of said additional compositions, wherein the spray or aerosol is applied to the surface of a body of a subject, including specific locations on the body of the subject for local administration of a drug or biologically active agent. For example, the aerosolized drug can be applied in spray form to an area of skin on a subject.

In accordance with an embodiment, the present invention provides peptide-based supramolecular filament compositions comprising one or more drug or biologically active agents for use in a spray or aerosol delivery or administration of said drug or biologically active agent.

In accordance with an embodiment, the present invention provides peptide-based supramolecular filament compositions comprising one or more drug or biologically active agents for use in a spray or aerosol delivery, application or administration of said drug or biologically active agent to a tissue of a subject.

In accordance with another embodiment, the present invention provides a method of local administration of one or more peptide-based supramolecular filament compositions comprising one or more drug or biologically active agents, and upon contact with body fluids the composition is capable of undergoing a change from solution state to nanofiber gelation state.

Enrichment at the large air-liquid interface produced from aerosol droplet formation was concluded to be the main driving force of supramolecular filament breakdown. The impact of the interactions with the air-liquid interface are dependent on the thermodynamic stability of the assembled state, which is reflected in the system's CAC values. Low stability systems (with a high CAC) show a higher degree of filament fragmentation and hydrogen bonding disruption, whereas high stability systems (low CAC) better maintain their filamentous shape and length. Therefore, through rational design of the peptidic units, particularly through alterations of the C-terminal amino acids, these peptide amphiphile compositions comprising supramolecular filaments can be engineered with suitable stability within liquid aerosols. Regardless of the CAC of the system however, the supramolecular structure stability can be further enhanced by encapsulating drugs and dyes within the core of the filaments, thereby increasing the strength of hydrophobic interactions to outweigh the influence of the air-liquid interface. The present inventors also show that tuning of the loading capacity of the supramolecular filament compositions influences the drug/dye output rate from the nebulizer device, allowing for controllable linear release profiles.

The peptide-based supramolecular filament compositions are a platform technology which can have multiple uses for inhalation-based therapy and imaging applications of lung-resident and other pulmonary diseases or conditions. The distinct shape and size of the filaments after nebulization should provide beneficial delivery properties of their loaded cargo into the lungs, where these systems can enhance therapeutic efficacy and retention through avoidance of the lungs' clearance mechanisms, particularly by exhibiting high aspect ratios that in turns mitigates the effects of the mucociliary escalator and alveolar macrophages. Moreover, the inventors show that through molecular design of C-terminal amino acids, they can modify the mucosal penetration properties of the compositions.

"Treating" or "treatment" is an art-recognized term which includes curing as well as ameliorating at least one symptom of any condition or disease. Treating includes reducing the likelihood of a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder or condition, e.g., causing any level of regression of the disease; inhibiting the disease, disorder or condition, e.g., impeding its progress; and relieving the disease, disorder or condition, even if the underlying pathophysiology is not affected or other symptoms remain at the same level.

"Prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

In one aspect of this invention, the peptide-based supramolecular filament compositions and one or more biologically active agents may be prepared. The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject. In some embodiments, a biologically active agent may be used in admixture with the peptide-based supramolecular filament compositions of this invention, to, for example, treat a bronchial infection.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention. Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: anti-neoplastics such as androgen inhibitors, antimetabolites, cytotoxic agents, and immunomodulators; anti-tussives such as dextromethorphan, hydrobromide, noscapine, carbetapentane citrate, and chlophedianol hydrochloride; antihistamines such as chlorpheniramine phenindamine tartrate, pyrilamine doxylamine succinate, and phenyltoloxamine citrate; decongestants such as hydrochloride, phenylpropanolamine hydrochloride, pseudoephedrine hydrochloride, and ephedrine; various alkaloids such as codeine phosphate, codeine sulfate, and morphine; mineral supplements such as potassium chloride, zinc chloride, calcium carbonate, magnesium oxide, and other alkali metal and alkaline earth metal salts; ion exchange resins such as such as N-acetylprocainamide; antipyretics and analgesics such as acetaminophen, aspirin and ibuprofen; appetite suppressants such as phenyl-propanol amine or caffeine; expectorants such as guaifenesin; antacids such as aluminum hydroxide and magnesium hydroxide; biologicals such as peptides, polypeptides, proteins and amino acids, hormones, interferons or cytokines and other bioactive peptidic compounds, such as calcitonin, ANF, EPO and insulin; anti-infective agents such as anti-fungals, antivirals, antiseptics and antibiotics; and desensitizing agents and antigenic materials, such as those useful for vaccine applications.

More specifically, non-limiting examples of useful biologically active agents include the following therapeutic categories: analgesics, such as nonsteroidal anti-inflammatory drugs, opiate agonists and salicylates; antihistamines, such as $H_1$-blockers and $H_2$-blockers; anti-infective agents, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary antiinfectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and *vinca* alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, α-blocker sympatholytics, sympatholytics, sympathomimetics, and adrenergic agonist sympathomimetics; cardiovascular agents, such as antianginals, antianginals, calcium-channel blocker antianginals, nitrate antianginals, antiarrhythmics, cardiac glycoside antiarrhythmics, class I antiarrhythmics, class antiarrhythmics, class antiarrhythmics, class IV antiarrhythmics, antihypertensive agents, a-blocker antihypertensives, angiotensin-converting enzyme inhibitor (ACE inhibitor) antihypertensives, β-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, reductase inhibitor antilipemics, inotropes, cardiac glycoside inotropes, and thrombolytic agents; dermatological agents, such as antihistamines, anti-inflammatory agents, corticosteroid anti-inflammatory agents, anesthetics, topical antiinfectives, topical antiinfectives, antiviral topical antiinfectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal antiinflammatory drugs, salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, anti-glaucoma agents, mitotics, anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid antiinflammatory agents, and ophthalmic nonsteroidal anti-inflammatory drugs; psychotropic agents, such as antidepressants, heterocyclic antidepressants, monoamine oxidase inhibitors selective serotonin re-uptake inhibitors tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory antiinflammatory agents, and respiratory corticosteroid anti-inflammatory agents; toxicology agents, such as antidotes, heavy agents, substance abuse agents, deterrent substance abuse agents, and withdrawal substance abuse agents; minerals; and vitamins, such as vitamin A, vitamin B, vitamin C, vitamin D, vitamin E, and vitamin K.

Other classes of biologically active agents from the above categories include: analgesics in general, such as lidocaine, other “caine” analgesics or derivatives thereof, and non-steroidal anti-int1ammatory drugs (NSAIDs) analgesics, including diclofenac, ibuprofen, ketoprofen, and naproxen; opiate agonist analgesics, such as codeine, fentanyl, hydromorphone, and morphine; salicylate analgesics, such as aspirin (ASA) (enteric coated ASA); $H_1$-blocker antihistamines, such as clemastine and terfenadine; $H_2$-blocker antihistamines, such as cimetidine, famotidine, nizadine, and ranitidine; anti-infective agents, such as mupirocin; antianaerobic antiinfectives, such as chloramphenicol and clindarnycin; antifungal antibiotic antiinfectives, such as amphotericin b, clotrimazole, fluconazole, and ketoconazole; macrolide antibiotic antiinfectives, such as azithromycin and erythromycin; miscellaneous antibiotic antiinfectives, such as and imipenem; penicillin, antibiotic anti-infectives, such as nafcillin, oxacillin, penicillin G, and penicillin V; quinolone antibiotic anti-infectives, such as ciprofloxacin and nortfloxacin; tetracycline antibiotic anti-infectives, such as doxycycline, minocycline and tetracycline; antituberculosis antimycobacterial antiinfectives such as isoniazid and rifampin; antiprotozoal antiinfectives, such as atovaquone and dapsone; antimalarial antiprotozoal anti-infectives, such as chloroquine and pyrimethamine; anti-retroviral antiinfectives, such as ritonavir and zidovudine; antiviral anti-infective agents, such as acyclovir, ganciclovir, interferon-γ, and rimantadine; alkylating antineoplastic agents, such as carboplatin and cisplatin; nitrosourea alkylating antineoplastic agents, such as carmustine (BCNU); antimetabolite antineoplastic agents, such as methotrexate; pyrimidine analog antineoplastic agents, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide, interferon; paclitaxel, other taxane derivatives, and tretinoin (ATRA); antibiotic natural antineoplastics, such as bleomycin, dactinomycin, daunorubicin, doxorubicin, and mitomycin; *vinca* alkaloid natural antineoplastics, such as vinblastine and vincristine; autonomic agents, such as nicotine; anticholinergic autonomic agents, such as benztropine and trihexyphenidyl; antimuscarinic anticholinergic autonomic agents, such as atropine and oxybutynin; ergot alkaloid autonomic agents, such as bromocriptine; cholinergic agonist parasympathomimetics, such as pilocarpine; cholinesterase inhibitor parasympathomimetics, such as pyridostigmine; α-blocker sympatholytics, such as prazosin; β-blocker sympatholytics, such as atenolol; adrenergic sympathomimetics, such as albuterol and dobutamine; cardiovascular agents, such as aspirin (ASA) (enteric coated ASA); β-blocker antianginals, such as atenolol and propranolol; calcium-channel blocker antianginals, such as nifedipine and verapamil; nitrate antianginals, such as isosorbide dinitrate (ISDN); cardiac glycoside antiarrhythmics, such as class I antiarrhythmics, such as lidocaine, mexiletine, phenytoin, procainamide, and quinidine; class antiarrhythmics II, such as atenolol, metoprolol, propranolol, and timolol; class III antiarrhythmics, such as amiodarone; class IV antiarrhythmics, such as diltiazem and verapamil; antihypertensives, such as prazosin; angiotensin-converting enzyme inhibitor (ACE inhibitor) antihypertensives, such as captopril and enalapril; antihypertensives, such as atenolol, metoprolol, nadolol, and propanolol; calcium-channel blocker antihypertensive agents, such as diltiazem and nifedipine; central-acting adrenergic antihypertensives, such as clonidine and methyldopa; diuretic antihypertensive agents, such as amiloride, furosemide, hydrochlorothiazide (HCTZ), and spironolactone; peripheral vasodilator antihypertensives, such as minoxidil; antilipemics, such as gemfibrozil and probucol; bile acid sequestrant antilipemics, such as cholestyramine; reductase inhibitor antilipemics, such as lovastatin and pravastatin; inotropes, such as amrinone, dobutamine, and dopamine; cardiac glycoside inotropes, such as thrombolytic agents, such as alteplase, anistreplase, streptokinase, and urokinase; dermatological agents, such as colchicine, isotretinoin, methotrexate, minoxidil, tretinoin dermatological corticosteroid anti-inflammatory agents, such as betamethasone and dexamethasone; antifungal topical antiinfectives, such as amphotericin clotrimazole, miconazole, and nystatin; antiviral topical antiinfectives, such as acyclovir; topical antineoplastics, such as electrolytic and renal agents, such as lactulose; loop diuretics, such as furosemide; potassium-sparing diuretics, such as triamterene; thiazide diuretics, such as hydrochlorothiazide (HCTZ); uricosuric agents, such as probenecid; enzymes and thrombolytic enzymes, such as alteplase, anistreplase, streptokinase and urokinase; antiemetics, such as prochlorperazine; salicylate gastrointestinal anti-inflammatory agents, such as sulfasalazine; gastric acid-pump inhibitor anti-ulcer agents, such as omeprazole;) $H_2$-blocker anti-ulcer agents, such as cimetidine, famotidine, nizatidine, ranitidine; digestants, such as pancrelipase; prokinetic agents, such as erythromycin; opiate agonist intravenous anesthetics such as fentanyl; hematopoietic antianemia agents, such as (G-CSF), and (GM-CSF); coagulation agents, such as factors 1-10 (AHF 1-10); anticoagulants, such as warfarin; thrombolytic enzyme coagulation agents, such as alteplase, anistreplase, streptokinase and urokinase; hormones and hormone modifiers, such as bromocriptine; abortifacients, such as methotrexate; antidiabetic agents, such as insulin; oral contraceptives, such as estrogen and progestin; progestin contraceptives, such as levonorgestrel and norgestrel; estrogens such as conjugated estrogens, diethylstilbestrol (DES), estrogen (estradiol, estrone, and estropipate); fertility agents, such as clomiphene, human chorionic gonadotropin (HCG), and menotropins; parathyroid agents such as calcitonin; pituitary hormones, such as desmopressin, goserelin, oxytocin, and vasopressin (ADH); progestins, such as medroxyprogesterone, norethindrone, and progesterone; thyroid hormones, such as levothyroxine; immunobiologic agents, such as interferon beta-1b and interferon gamma-lb; immunoglobulins, such as immune globulin IgM, IgG, IgA; amide local anesthetics, as lidocaine; ester local anesthetics, such as benzocaine and procaine; musculoskeletal corticosteroid antiinflammatory agents, such as beclomethasone, betamethasone, cortisone, dexamethasone, hydrocortisone, and prednisone; musculoskeletal anti-inflammatory immunosuppressives, such as azathioprine, cyclophosphamide, and methotrexate; musculoskeletal nonsteroidal anti-inflammatory drugs such as diclofenac, ibuprofen, ketoprofen, ketorlac, and naproxen; skeletal muscle relaxants, such as and diazepam; reverse neuromuscular blocker skeletal muscle relaxants, such as pyridostigmine; neurological agents, such as nimodipine, riluzole, tacrine and ticlopidine; anticonvulsants, such as carbamazepine, gabapentin, lamotrigine, phenytoin, and valproic acid; barbiturate anticonvulsants, such as phenobarbital and primidone; benzodiazepine anticonvulsants, such as clonazepam, diazepam, and lorazepam; anti-Parkinson's' agents, such as bromocriptine, levodopa, carbidopa, and pergolide; anti-vertigo agents, such as meclizine; opiate agonists, such as codeine, fentanyl, hydromorphone, methadone, and morphine; opiate antagonists, such as naloxone; antiglaucoma agents, such as timolol; mitotic anti-glaucoma agents, such as pilocarpine; ophthalmic aminoglycoside antiinfectives, such as gentamicin, neomycin, and tobramycin; ophthalmic quinolone antiinfectives, such as ciprofloxacin, norfloxacin, and ofloxacin; ophthalmic corticosteroid anti-agents, such as dexamethasone and prednisolone; ophthalmic nonsteroidal anti-inflammatory drugs such as diclofenac; antipsychotics, such as clozapine, haloperidol, and risperidone; benzodiazepine anxiolytics, sedatives and hypnotics, such as clonazepam, diazepam, lorazepam, oxazepam, and prazepam; psychostimulants, such as methylphenidate and pemoline; such as codeine; bronchodilators, such as adrenergic agonist bronchodilators, such as albuterol; respiratory corticosteroid antiinflammatory agents, such as dexamethasone; antidotes, such as flumazenil and naloxone; heavy metal agents, such as penicillamine; deterrent substance abuse agents, such as disulfiram, naltrexone, and nicotine; withdrawal substance abuse agents, such as bromocriptine; minerals, such as iron, calcium, and magnesium; vitamin B compounds, such as cyanocobalamin (vitamin B12) and niacin (vitamin B3); vitamin C compounds, such as ascorbic acid; and vitamin D such as calcitriol.

Further, recombinant or cell-derived proteins may be used, such as recombinant beta-glucan; bovine immunoglobulin concentrate; bovine superoxide dismutase; formulation comprising fluorouracil, epinephrine, and bovine collagen; recombinant hirudin (r-Hir), HIV-1 immunogen; recombinant human growth hormone recombinant EPO (r-EPO); gene-activated EPO (GA-EPO); recombinant human hemoglobin (r-Hb); recombinant human mecasermin (r-IGF-1); recombinant interferon α; lenograstim (G-CSF); olanzapine; recombinant thyroid stimulating hormone (r-TSH); and topotecan.

Still further, the following listing of peptides, proteins, and other large molecules may also be used, such as interleukins 1 through 18, including mutants and analogues; interferons a, y, and which may be useful for cartilage regeneration, hormone releasing hormone (LHRH) and analogues, gonadotropin releasing hormone transforming growth factor (TGF); fibroblast growth factor (FGF); tumor necrosis factor-α); nerve growth factor (NGF); growth hormone releasing factor (GHRF), epidermal growth factor (EGF), connective tissue activated osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-a-y-globulin; superoxide dismutase (SOD); and complement factors, and biologically active analogs, fragments, and derivatives of such factors, for example, growth factors.

Members of the transforming growth factor (TGF) supergene family, which are multifunctional regulatory proteins, may be incorporated in a polymer matrix of the present invention. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)), (for example, inhibin A, inhibin B), growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Buffers, acids and bases may be incorporated in the inventive compositions to adjust pH. Agents to increase the diffusion distance of agents released from the composition may also be included.

The charge, lipophilicity or hydrophilicity of the peptide-based supramolecular filament compositions may be modified by employing an additive. For example, surfactants may be used to enhance miscibility of poorly miscible liquids. Examples of suitable surfactants include dextran, polysorbates and sodium lauryl sulfate. In general, surfactants are used in low concentrations, generally less than about 5%.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to retard microbial growth, and may be added in amounts ranging from 0.2%-1% (w/v). Suitable preservatives for use with the present invention include phenol, benzyl alcohol, m-cresol, octadecyldimethylbenzyl ammonium chloride, benzyaconium halides (e.g., chloride, bromide and iodide), hexamethonium chloride, alkyl parabens, such as, methyl or propyl paraben, catechol, resorcinol, cyclohexanol and 3-pentanol.

Isotonicifiers are present to ensure physiological isotonicity of liquid compositions of the instant invention and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose or glucose; disaccharides, such as lactose, maltose and sucrose; trisaccharides, such as raffinose; polysaccharides, such as, dextran and so on. Stabilizers can be present in the range from 0.1 to 10,000 w/w per part of biopolymer.

Additional miscellaneous excipients include bulking agents, (e.g., starch), chelating agents (e.g., EDTA), antioxidants (e.g., ascorbic acid, methionine or vitamin E) and cosolvents.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

The present the peptide-based supramolecular filament compositions provide liquid formulations of the peptide-based supramolecular filament compositions having a pH ranging from about 5.0 to about 8.0, or about 5.5 to about 7.5, or about 5.8 to about 7.2, or about 7.0 to about 7.5, or about 7.0 to about 7.4.

The instant peptide-based supramolecular filament compositions encompass formulations, such as, liquid formulations having stability at temperatures found in a commercial refrigerator and freezer found in the office of a physician or laboratory, such as from about 20° C. to about 5° C., said stability assessed, for example, by microscopic analysis, for storage purposes, such as for about 60 days, for about 120 days, for about 180 days, for about a year, for about 2 years or more. The liquid formulations of the present invention also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10%

The peptide-based supramolecular filament compositions formulations to be used for in vivo administration must be sterile. That can be accomplished, for example, by filtration through sterile filtration membranes. For example, the formulations of the present invention may be sterilized by filtration.

The peptide-based supramolecular filament compositions will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the biopolymer to be administered will be governed by such considerations, and can be the minimum amount necessary to prevent, ameliorate or treat a disorder of interest. As used herein, the term "effective amount" is an equivalent phrase refers to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease.

Biologically active agents and other additives may be incorporated into the peptide-based supramolecular filament compositions by admixture or added to a reagent preparation. Alternatively, the agents may be incorporated into peptide-based supramolecular filament compositions by binding these agents to the functional groups on the molecules of interest. Such compositions may include linkages that can be easily biodegraded, for example as a result of enzymatic degradation, resulting in the release of the active agent or additive into the target tissue, where it will exert its desired therapeutic effect.

In certain embodiments, the peptide-based supramolecular filament compositions of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between about 25 and 37° C. In other embodiments, the nanofiber hydrogel degrades in a period of between about one hour and several weeks, depending on the desired application. In some embodiments, the nanofiber hydrogel may include a detectable agent that is released on degradation.

Starting materials and reagents used in preparing these peptide-based supramolecular filament of the present invention are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols. 1-17, John Wiley and Sons, New York, N.Y., 1991; Rodd's Chemistry of Carbon Compounds, vols. 1-5 and supplements, Elsevier Science Publishers, 1989; Organic Reactions, vols. 1-40, John Wiley and Sons, New York, N.Y., 1991; March J; Advanced Organic Chemistry, $4^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature. For example, N-pyrrolidineacetic acid is described in Dega-Szafran Z and Pryzbylak R. Synthesis, IR, and NMR studies of zwitterionic α-(1-pyrrolidine)alkanocarboxylic acids and their N-methyl derivatives. J. Mol. Struct.: 436-7, 107-121, 1997; and N-piperidineacetic acid is described in Matsuda O, Ito S, and Sekiya M. each article herein expressly incorporated herein fully by reference.

Conveniently, synthetic production of the peptide-based supramolecular filaments of the invention may be according to the solid-phase synthetic method described by Goodman M. (ed.), "Synthesis of Peptides and Peptidomimetics" in Methods of organic chemistry (Houben-Weyl) (Workbench Edition, E22a, b, c, d, e; 2004; Georg Thieme Verlag, Stuttgart, New York), herein expressly incorporated fully by reference. This technique is well understood and is a common method for preparation of peptides. The general concept of this method depends on attachment of the first amino acid of the chain to a solid polymer by a covalent bond. Succeeding protected amino acids are added, on at a time (stepwise strategy), or in blocks (segment strategy), until the desired sequence is assembled. Finally, the protected peptide is removed from the solid resin support and the protecting groups are cleaved off. By this procedure, reagents and by-products are removed by filtration, thus eliminating the necessity of purifying intermediaries.

Amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate and polystyrene. Suitable resins are commercially available and well known to those of skill in the art. Appropriate protective groups usable in such synthesis include tert-butyloxycarbonyl (BOC), benzyl (Bzl), t-amyloxycarbonyl (Aoc), tosyl (Tos), o-bromo-phenylmethoxycarbonyl (BrZ), 2,6-dichlorobenzyl ($BzlCl_3$), and phenylmethoxycarbonyl (Z or CBZ). Additional protective groups are identified in Goodman, cited above, as well as in McOmie J F W: Protective Groups in Organic Chemistry, Plenum Press, New York, 1973, both references expressly incorporated fully herein by reference.

General procedures for preparing peptide-based supramolecular filament compositions of the present invention of this invention involve initially attaching a carboxyl-terminal protected amino acid to the resin. After attachment the resin is filtered, washed and the protecting group on the alpha-amino group of the carboxyl-terminal amino acid is removed. The removal of this protecting group must take place, of course, without breaking the bond between that amino acid and the resin. The next amino, and if necessary, side chain protected amino acid, is then coupled to the free amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide. The cleavage techniques used to separate the peptide from the resin and to remove the protecting groups depend upon the selection of resin and protecting groups and are known to those familiar with the art of peptide synthesis.

Peptides may be cyclized by the formation of a disulfide bond between two cysteine residues. Methods for the formation of such bonds are known and include such methods as those described in G. A. Grant (Ed.) Synthetic Peptides A User's Guide $2^{nd}$ Ed., Oxford University Press, 2002, W. C. Chan and P. D. White (Eds.) Fmoc Solid Phase Synthesis A Practical Approach, Oxford University Press, 2000 and references therein.

Alternative techniques for peptide synthesis are described in Bodanszky et al, Peptide Synthesis, 2nd ed, John Wiley and Sons, New York, 1976, expressly incorporated herein fully by reference. For example, the peptides of the invention may also be synthesized using solution peptide synthesis methodologies, involving either stepwise or block coupling of amino acids or peptide fragments using chemical or enzymatic methods of amide bond formation (see, e.g. H. D. Jakubke in The Peptides, Analysis, Synthesis, Biology, Academic Press, New York, 1987, p. 103-165; J. D. Glass, ibid., pp. 167-184; and European Patent 0324659 A2, describing enzymatic peptide synthesis methods.)

Commercial peptide synthesizers, such as the Applied Biosystems Model 430A, are available for the practice of these methods.

Prior to mixture with one or more drugs or biologically active agents, the peptide-based supramolecular filament solutions are dissolved in an aqueous solution and allowed to age for a period of time to attain their desired 3-dimensional form. The period for aging the supramolecular filament compositions of the present invention ranges from a few hours to a day or more, including, for example, 3, 4, 5, 6, 7, 8, 9, 10, 11, 12, 14, 18, 20, 24, 30, 36, up to 48 hours.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Materials

All Fmoc amino acids and resins were purchased from Advanced Automated Peptide Protein Technologies (AAPPTEC, Louisville, KY). The oligoethylene glycol chain with carboxylic acid terminal ($mPEG_4$-$CH_2CH_2COOH$ ($OEG_5$-COOH)) was purchased from PurePEG LLC (San Diego, CA). Paclitaxel was purchased from Ava Chem Scientific (San Antonio, TX). Coumarin 6 was acquired from Acros Organics (Fairlawn, NJ). Budesonide was sourced from TCI America (Portland, OR). All other reagents and solvents were sourced from VWR (Radnor, PA) or Sigma-Aldrich (St. Louis, MO).

Peptide Synthesis and Purification

All peptide amphiphile molecules were synthesized with the standard 9-fluorenylmethoxycarbonyl (Fmoc) solid phase peptide synthesis technique. All three peptide amphiphiles (EPA, OPA, and KPA) were synthesized onto a Rink Amide MBHA resin. Fmoc deprotection was performed with 20% 4-methylpiperidine in dimethylformamide (DMF) for 15 minutes, repeated once. After Fmoc removal, each amino acid was conjugated onto the peptide chain at a 4:4:6 molar ratio of the Fmoc-amino acid, O-benzotriazole-N,N,N',N'-tetramehtyl-uronium-hexafluorophosphate (HBTU), and diisopropylethylamine (DIEA) to resin in DMF and allowed to react for 2 h. After last amino acid conjugation, lauric acid ($C_{12}$ alkyl chain) was coupled to the peptide sequence in a 4:4:6 molar ratio to resin of lauric acid, HBTU, and DIEA in DMF and allowed to react overnight. For the OPA peptide, Mtt deprotection to lysine side chains was conducted with 3% trifluoroacetic acid (TFA) solution (5% triisopropylsilane (TIS), 92% dichloromethane (DCM)) for 10 min and repeated 5-6 times. $OEG_5$-COOH was coupled to the lysine side chains at a molar ratio of 2:2:3 to resin of $OEG_5$-COOH, HBTU, and DIEA. The completed PAs were cleaved from their resin by addition of a 10 mL mixture of 95% TFA, 2.5% TIS, and 2.5% water and shaken for 3 h. After cleavage, the TFA solution containing PA was collected and precipitated with cold diethyl ether. After washing with diethyl ether, the crude PA precipitate was left under a fume hood to dry.

The crude PA solids were then dissolved in a water and acetonitrile (ACN) mixture containing 0/1% v/v TFA for KPA and OPA molecules and 0.1% v/v $NH_4OH$ for EPA. A Varian ProStar Model 325 high performance liquid chromatography (HPLC) (Agilent Technologies, Santa Clara, CA) was used to purify the PA molecules using mobile phases of water and acetonitrile. Separation of PAs from impurities was performed using a Varian PLRP-S column (100 Å, 10 μm, 150×25 mm) with a flow rate of 20 mL/min, 10 mL injections, and monitoring at 220 nm for all molecules. For EPA, the gradient was run from 5% to 35% over 30 min; for OPA, the gradient was run from 20% to 65% ACN over 30 min; for KPA, the gradient was run from 20% to 50% ACN over 25 min. The collected fractions were analyzed by matrix-assisted laser desorption/ionization time of flight (MALDI-TOF) mass spectrometry to isolate the fractions containing the molecule of interest. The correct fractions were combined, and excess ACN was removed via rotary evaporation. Samples were then lyophilized using a FreeZone −105° C. 4.5 L freeze dryer (Labconco, Kansas City, MO). Re-characterization of the purified PA powders were conducted by RP-HPLC and MALDI-TOF, where PAs were calibrated, aliquoted into cryo-vials, and re-lyophilized. The purified powders were stored in a −20° C. freezer for future use.

Budesonide Drug Amphiphile Synthesis

Synthesis of 4-(pyridin-2-yldisufanyl) butyric acid

First, 4-bromobutyric acid (2 g, 12 mmol) and thiourea (0.96 g, 12.6 mmol) were dissolved in ethanol (50 mL) and refluxed at 90° C. for 4 hours. Afterward, an NaOH solution (4.8 g in a 5:1 water/ethanol ratio by volume solution) was added dropwise and the resulting mixture was refluxed for an additional 16 hours and then cooled to room temperature. The resulting white precipitate was collected and redissolved in water (40 mL), where subsequently 4 M HCl (aq) was added to adjust the solution pH to 5. Next, the product was isolated by extraction into diethyl ether as the organic phase, which was then dried over anhydrous magnesium sulfate to give 4-sulfanylbutyric acid as a colorless oil (350 mg, 15%) and used in the next step without further purification. Next, 4-sulfanylbutyric acid (105 mg, 0.87 mmol) and 2-aldrithiol (440 mg, 2.0 mmol, 2.3 eq) were dissolved in methanol (7 mL) and stirred for 3 hours. The solution was then purified by RP-HPLC (5% to 95% of acetonitrile in water with 0.1% v/v TFA over 45 min), where product fractions were collected and solvents removed to gives 4-(pyridin-2-yldisulfanyl) butyric acid as an oil (118 mg, 59%).

Synthesis of budesonide C2 ester

Budesonide C2 ester was synthesized using a previously published procedure with adaptation for the drug budesonide. Budesonide (216 mg, 0.5 mmol), 4-(pyridine-2-yldisulfanyl) butyric acid (298 mg, 1.3 mmol, 2.6 eq), DIC (180 μL, 1.15 mmol, 2.3 eq), and DMAP (61 mg, 0.5 mmol) were added to an oven-dried flask equipped with a stir bar. The flask was evacuated and refilled with nitrogen 3 times to remove air, and then the reactants were dissolved in anhydrous dichloromethane (10 mL). The reaction was allowed to stir in the dark at room temperature for 48 hours. The solvents were removed in vacuo and the remaining residue was dissolved in chloroform, where then the product was purified by flash chromatography (3:2 v/v ethyl acetate/hexane as elution solvent), yielding the product as a white solid (164 mg, 51%).

Scheme 1. Synthesis of budesonide C2 ester (BUD-buSS).

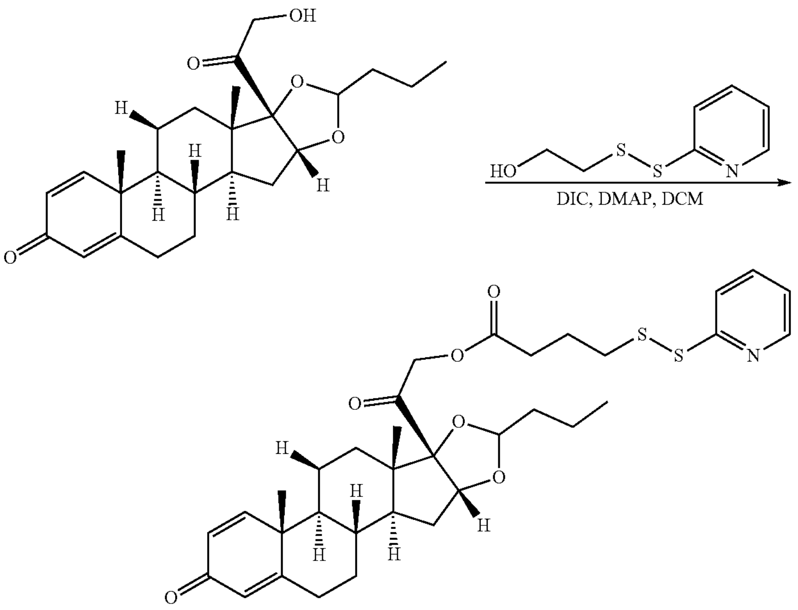

Synthesis of Budesonide-Peptide Conjugates

Previously synthesized peptides (1 eq by mole) and budesonide C2 ester (2 eq by mole) were added to an over-dried flask equipped with a stir bar. The reagents were then dissolved in DMF (2 mL) and the solution was allowed to stir in the dark for 24 s before purification by HPLC (10% to 90% acetonitrile in water over 30 min). Product fractions were collected, combined, and then lyophilized to give products as a white powder.

Matrix-Assisted Laser Desorption/Ionization Time of Flight Mass Spectrometry (MALDI-TOF)

Figures 2A, 2B:
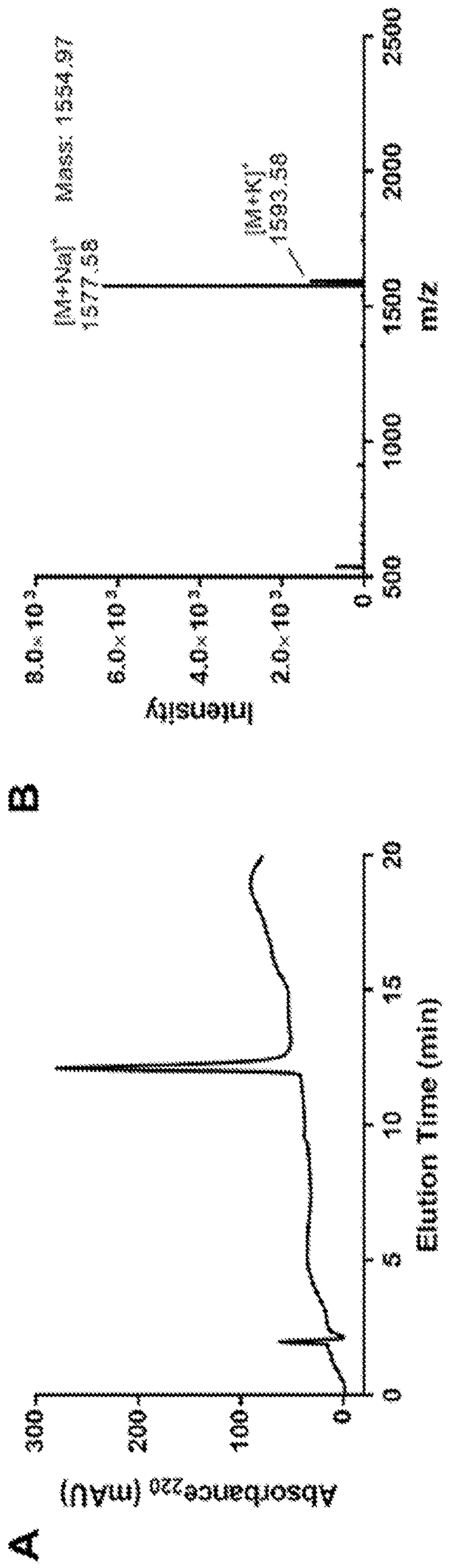
FIGS. 2A-2B depicts the (2A) Analytical RP-HPLC chromatogram and (2B) MALDI-TOF mass spectrum of OPA.
Figures 3A, 3B:
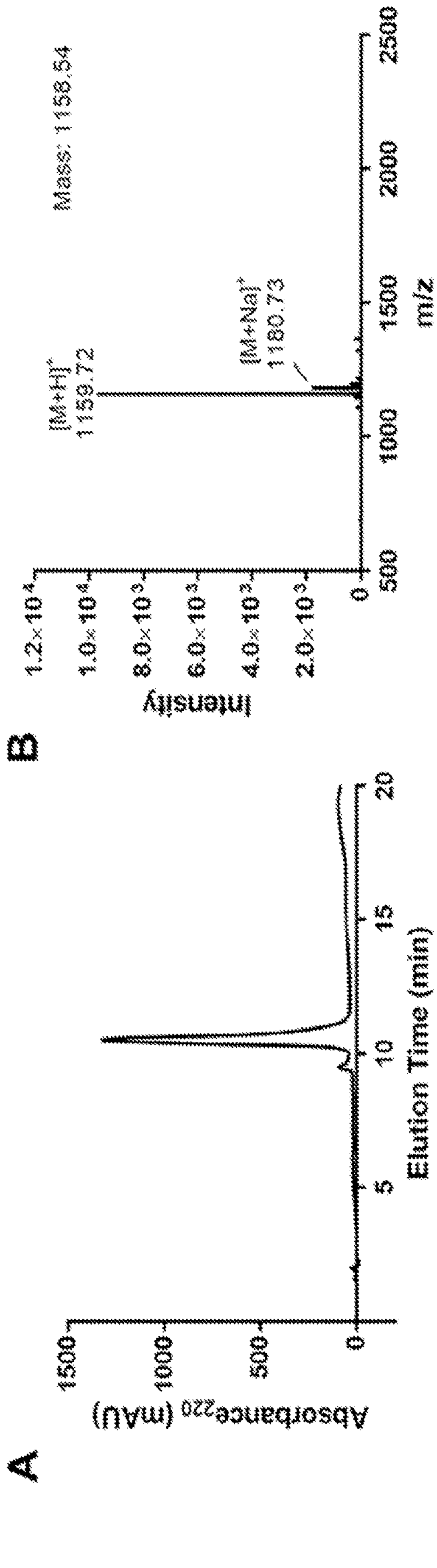
FIGS. 3A-3B depicts the (3A) Analytical RP-HPLC chromatogram and (3B) MALDI-TOF mass spectrum of KPA.

The molecular weights of the synthesized PAs were determined using MALDI-TOF mass spectrometry with a BrukerAutoflex III MALDI-TOF instrument (Bruker, Billerica, MA). For sample preparation, 2 μL of sinapic acid matrix (10 mg/mL in 1:1 v/v water/ACN with 0.05% v/v TFA; Sigma-Aldrich, St. Louis, MO) was deposited onto an MTP 384 ground steel target plate (Bruker, Billerica, MA). The matrix was allowed to dry for 5-10 min. After drying, 1 μL of aqueous PA solution was added to the corresponding spot of dried matrix followed by an immediate addition of 1 μL of sinapic matrix and mixed with the PA solution. The samples were allowed to dry for 10-20 min. In the instrument, the samples were irradiated with a 355 nm UV laser and analyzed in the reflectron mode. Representative mass spectra of the PAs are represented in FIGS. 1-3.

Analytical High Performance Liquid Chromatography (HPLC)

Analytical measurements with reverse-phase HPLC were performed with a Varian ProStar Model 325 HPLC (Agilent Technologies, Santa Clara, CA) using a Varian Pursuit XRs C18 column (5 μm, 150×4.6 mm) with a flow rate of 1 mL/min, 20 μL injections, and monitoring at 220 nm. The purity of the three PA molecules was confirmed using a gradient of 5% to 95% ACN over 15 min, where area under the curve (AUC) of the PA peak relative to total AUC of all peaks was used to confirm purity greater than 95%. The purity data for each molecule is shown in FIGS. 1-3.

Calibration curves of the PA molecule concentrations were constructed by running different concentrations of the PAs at a gradient of 35% to 90% ACN over 15 min with monitoring at 280 nm (for tyrosine residue absorbance). The same gradient was used for calibration of the free drugs and dye studied in this work with monitoring at 237 nm for paclitaxel, 456 nm for coumarin 6, and 244 nm for budesonide. The AUC of the peak was plotted against the concentration, and the data fit with a linear regression.

Zeta Potential Measurements

Solutions of the three PAs were dissolved in water and calibrated to pH=7.4 using aqueous solutions of hydrochloric acid and sodium hydroxide. The solutions were allowed to age overnight at room temperature. The filament composition solutions were then added into a capillary cell and analyzed using a Malvern ZEN3690 Zetasizer (Malvern Panalytical, Westborough, MA) at 25° C. Three repeated measurements were performed for each sample (10 measurements/run) and then averaged. Zeta potential measurements of EPA, OPA, and KPA are displayed in FIG. 4.

Example 1

Figures 5A, 5B:
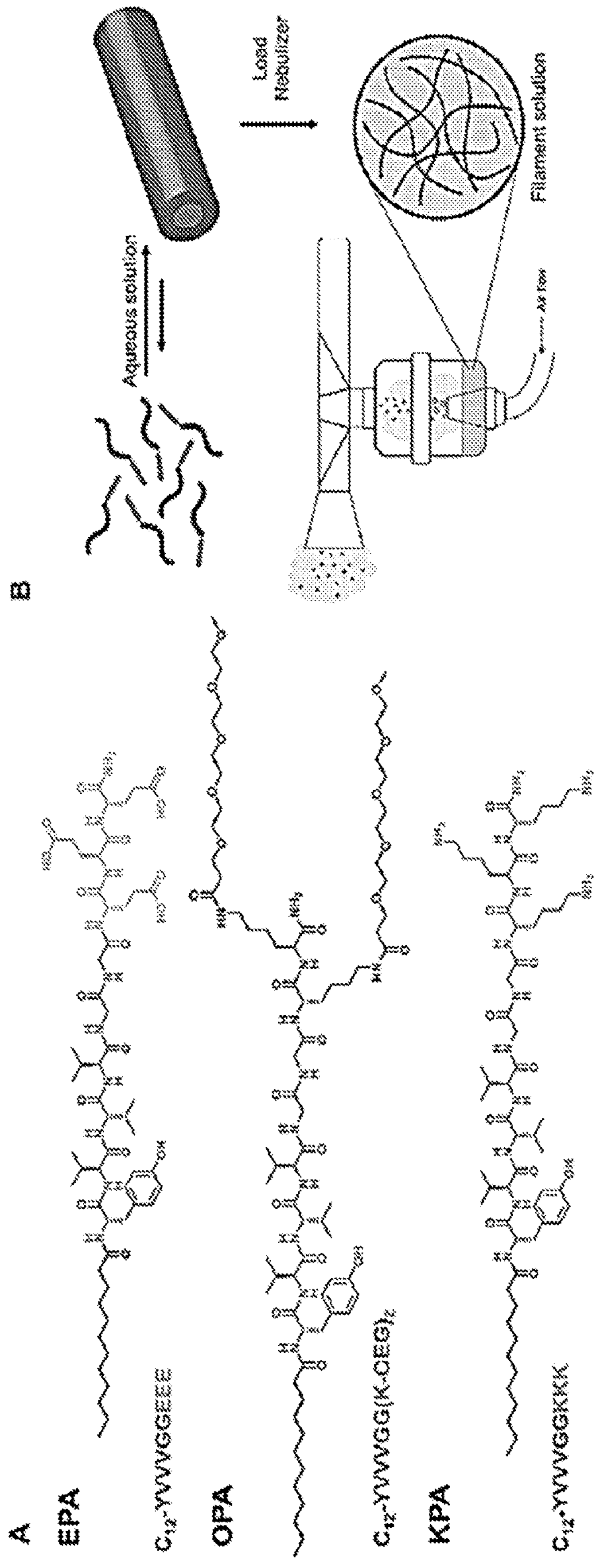
FIGS. 5A-5B depict the molecular design and assembly of three peptide amphiphiles and their potential use as inhalable drug carriers. (5A) Chemical structures of the three peptide amphiphiles studied, where each contains a dodecyl alkyl chain (black) and the same hydrogen bond-regulating peptide sequence with glycine spacer (blue) but vary by surface charge. EPA contains three glutamic acid residues (light blue) for negative charge; OPA contains two oligoethylene glycol-decorated lysines (green) for neutral charge; and KPA contains three lysine residues for positive charge (red). (5B) The peptide amphiphile monomers, composed of a hydrophobic alkyl chain (green) and a hydrophilic peptide segment (blue) spontaneously assemble in aqueous solutions into supramolecular filaments. Solutions of these filaments are then loaded into a jet nebulizer to produce filament-bearing liquid aerosol droplets. YVVVGGEEE (SEQ ID NO: 2); YVVVGGKK (SEQ ID NO: 4); YVVVGGKKK (SEQ ID NO: 3).

Molecular Design. Three peptide amphiphile (PA) molecules, each composed of a hydrophilic peptide segment and a hydrophobic alkyl chain, were designed to self-assemble into filamentous nanostructures. By manipulating the amino acid sequence at the C-terminus, we can influence the overall surface charge of the resulting supramolecular structures, with the aim of creating systems of varying surface charge to compare their aerosolization properties. As shown in FIG. 5, each molecule differs with respect to the charged or neutral amino acids at the C-terminus, which are separated by a double glycine (GG) spacer and help enhance the overall solubility and amphiphilicity of the PA molecule. The amphiphile EPA contains three glutamic acid residues (EEE) for a negative surface charge; OPA contains two lysine residues decorated with short oligoethylene glycol (OEG) chains for a neutral surface charge; and KPA contains three lysine residues (KKK) for a positive surface charge. Each PA contains a dodecyl chain ($C_{12}$ alkyl group) to act as the hydrophobic domain of the amphiphiles to promote hydrophobic interactions during self-assembly. Moreover, each molecule contains the same intermolecular hydrogen bond-regulating peptide sequence (YVVV) (SEQ ID NO: 1), where the tyrosine residue (whose absorbance is also used for concentration calibration) can partake in π-π interactions and the valine residues can promote β-sheet formation to provide directionality to the supramolecular structures. All peptide amphiphiles were synthesized following standard Fmoc solid-phase peptide synthesis protocols. After synthesis, the molecules were purified using reverse-phase high-performance liquid chromatography (RP-HPLC) and their molecular weights confirmed using MALDI-TOF mass spectroscopy (FIGS. 1-3). Upon dissolution in water and aging for one day, these peptide amphiphiles can spontaneously arrange into supramolecular filaments of several microns in length. The resulting filament solution could then be transferred to a jet nebulizer to study their aerosolization properties within liquid droplets, as depicted in FIG. 5B.

Example 2

Molecular Assembly and Filament Characterization Post-Nebulization.

Figure 4:
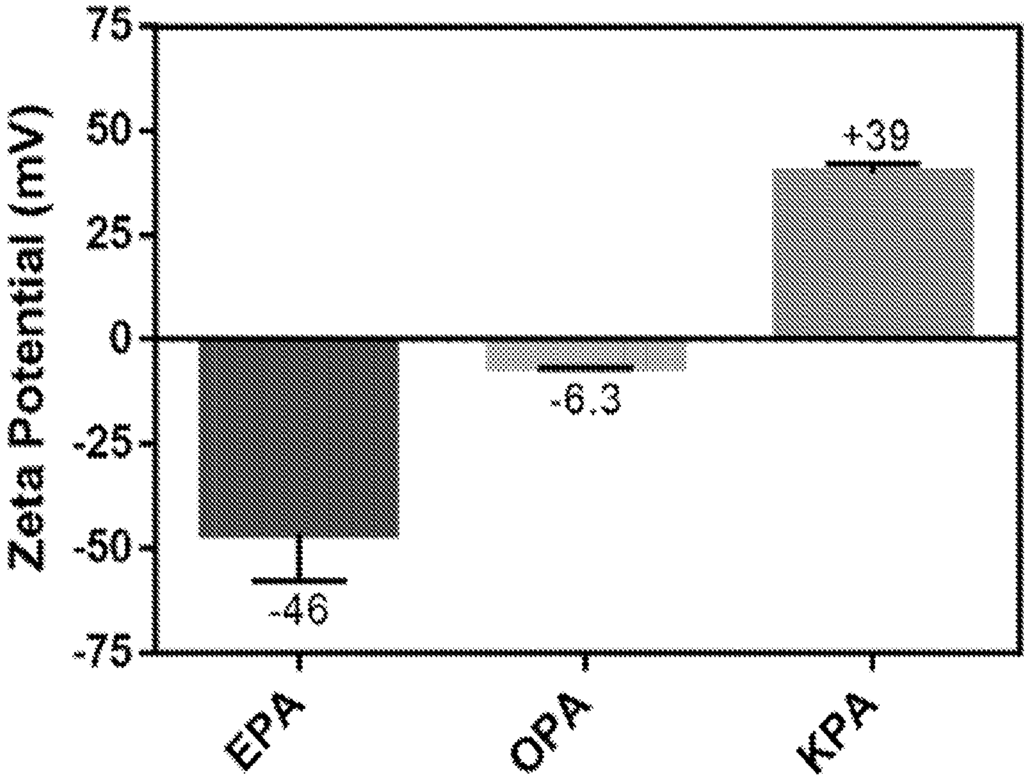
FIG. 4 shows Zeta potential (mV) measurements of the three PA filament systems, confirming intended surface charge by molecular design of C-terminus amino acids of the PAs. Data are given as mean±SD (n=3).
Figures 6A, 6B, 6C, 6D, 6E, 6F, 6G, 6H, 6I:
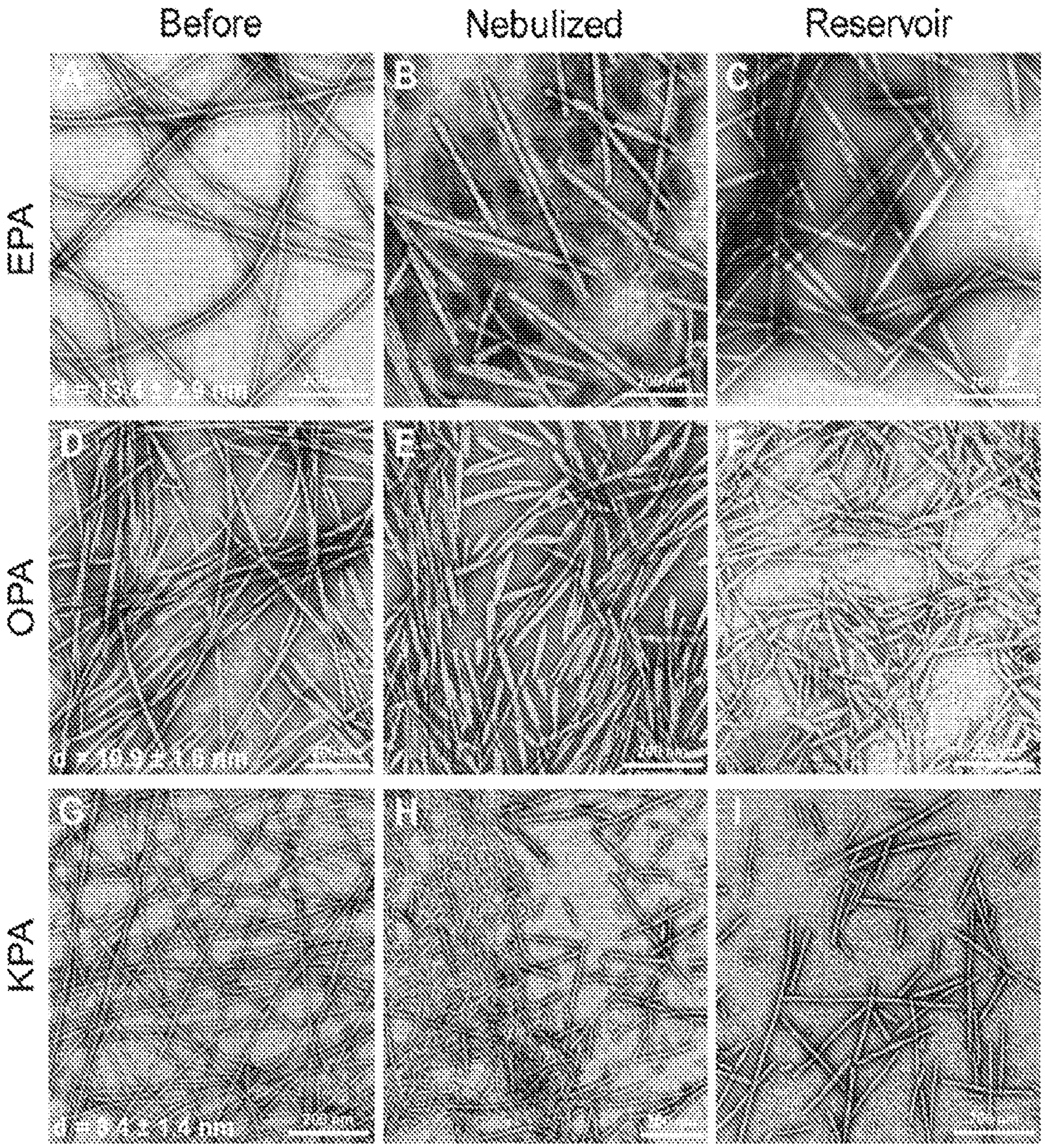
FIGS. 6A-6I show representative transmission electron microscopy (TEM) images of the supramolecular filaments formed from (6A) EPA, (6D) OPA, and (6G) KPA at 500 UM after dissolving in water and aging for 24 h. Filaments are several microns in length, and a ribbon-like morphology with variable twisting is observed for EPA and OPA, whereas KPA formed nanofibers. Filament diameters represented as mean±SD (n=35). TEM images of EPA filaments at 500 μM after jet nebulization for 10 min collected in the mist (6B) and leftover in the reservoir (6C), where filaments are still observed but with a reduced length. TEM images of OPA filaments at 500 μM after jet nebulization for 10 min collected in the mist (6E) and leftover in the reservoir (6F), where filaments are still observed with reduced length. TEM images of KPA filaments at 500 μM after jet nebulization for 10 min collected in the mist (6H) and leftover in the reservoir (6I), resulting in reduced filament length and the formation of fibrils and worm-like micelles. Scale bars represent 200 nm.

To understand the behavior of these filaments during aerosol delivery, the inventors first compared any observable structural changes to their morphology during jet nebulization. All PAs were dissolved at 2 mM in water and aged for 24 h at room temperature before observing their assemblies. FIGS. 6A, 6D, and 6G depict transmission electron microscopy (TEM) images of EPA, OPA, and KPA, respectively, where all three PAs are observed to form filamentous nanostructures over several microns in length. Our analysis revealed the tendency for EPA and OPA to produce ribbon-like structures with varying degrees of twisting, while KPA favored straight fibers. Moreover, zeta potential measurements were conducted on the filament systems, which confirmed the surface charge of the assemblies was aptly conferred by the C-terminal amino acid design (FIG. 4).

Figures 7A, 7B:
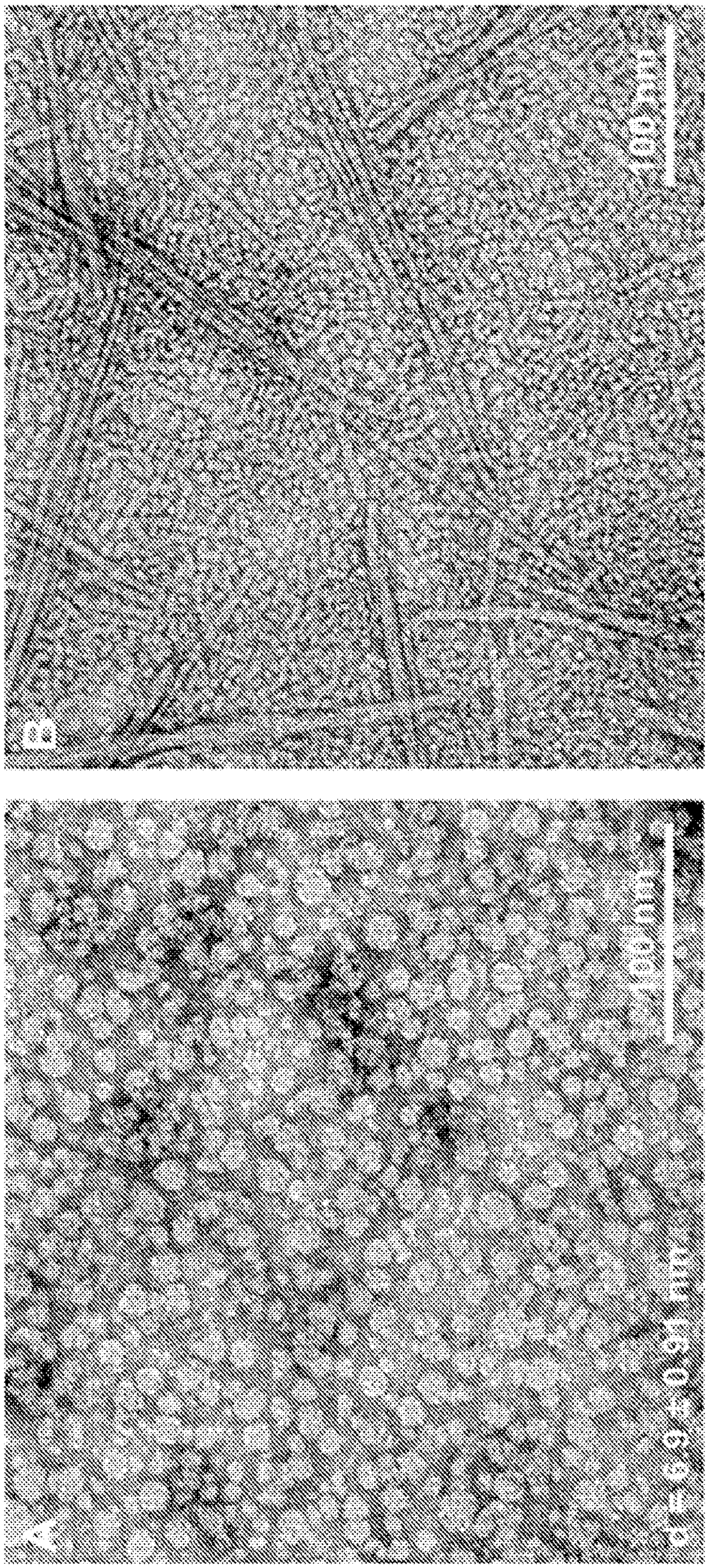
FIGS. 7A-7B show representative TEM images of the formed spherical micelles resulting from jet nebulization (10 min) of KPA filaments that are present in the solutions of the (7A) nebulized mist and (7B) reservoir. Concentration of KPA is 500 UM in water. Diameter of the spherical micelles is given as mean±SD (n=35). Scale bars represent 100 nm.
Figures 8A, 8B:
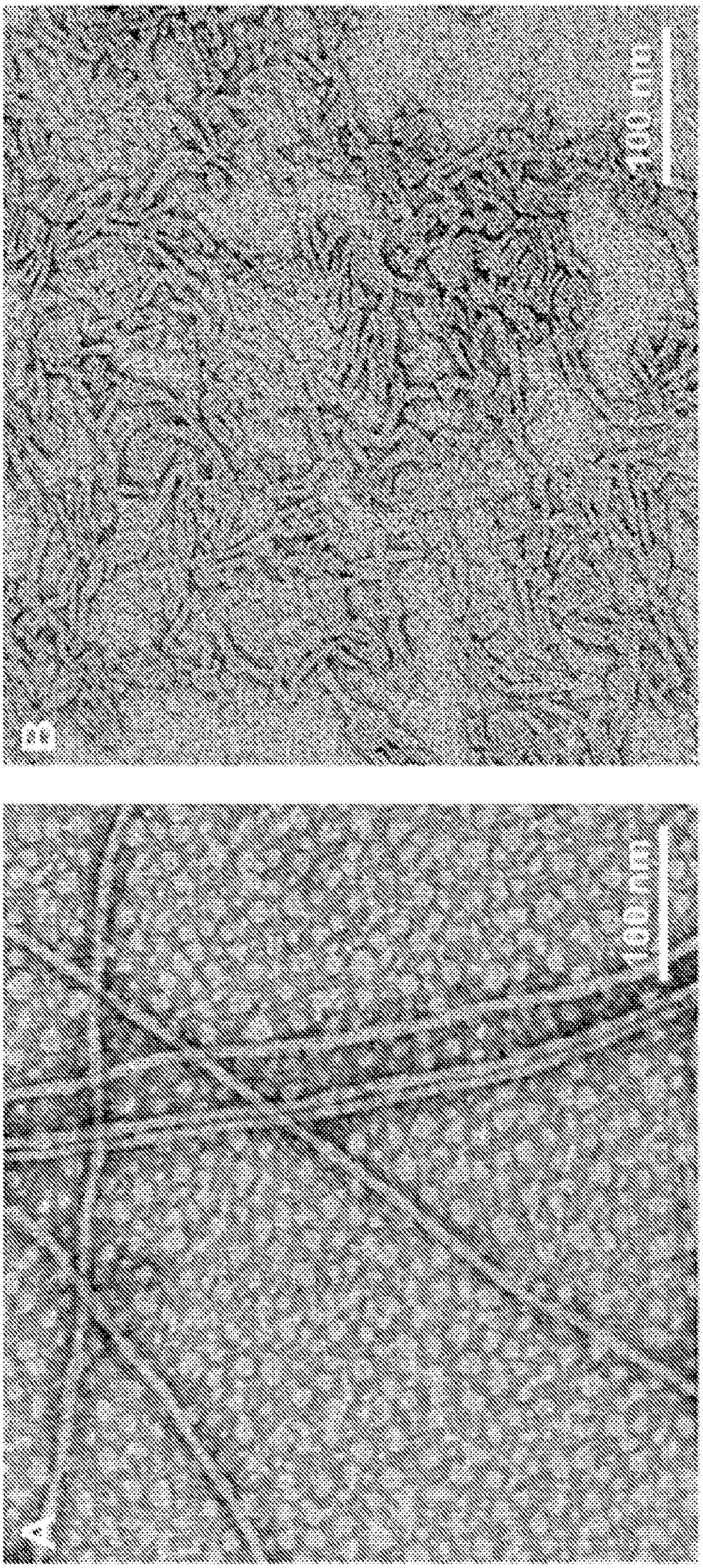
FIGS. 8A-8B show representative TEM images of KPA filaments after dilution from 500 UM to 100 μM. (8A) Spherical micelles are observed alongside the long filaments. Moreover, (8B) worm-like micelles are also observed, suggesting the filament breakdown of KPA is reminiscent of a dilution effect.

Since the supramolecular filament compositions are several microns long and are formed through non-covalent interactions, their structural integrity may be influenced by a number of factors during nebulization, such as agitation and aerosol formation. Thus, we first assessed the structural stability of these systems while traveling in aerosol droplets generated by a jet nebulizer. Nebulizers are commonly employed medical devices for producing liquid aerosol droplets containing therapeutics via high velocity airflow through the device nozzle. Droplets very large in diameter impact baffles and/or the walls of the nebulizer and are recycled back into the device's reservoir, but droplets small enough to circumvent these barriers (typically ranging in diameter from 1 to 10 μm) exit the device as a respirable aerosol. Therefore, we characterized two groups of structures after nebulization: the exiting mist and the leftover solution in the reservoir. Filament compositions in solutions diluted down to 500 M of the different PAs were loaded into a jet nebulizer and nebulized for 10 minutes, and the mist and leftover reservoir solutions were collected and subsequently analyzed with TEM. The EPA filaments after nebulization both in the mist (FIG. 6B) and reservoir (FIG. 6C) maintained their filamentous structure but a notable reduction in length was observed. This same observation is made for the OPA filaments for the nebulized (FIG. 6E) and reservoir populations (FIG. 6F), where shorter filaments are produced. However, a striking difference is observed for the KPA filaments; while a length reduction is noted, we also observed the formation of different morphologies in both populations (FIGS. 6H and 61). For both the nebulized and reservoir populations, we see the introduction of short bundled fibrils, worm-like micelles, and spherical micelles (spherical micelles depicted in FIG. 7). These resultant structures are reminiscent of a dilution effect, as the worm-like micelles and spherical micelles were observed for KPA after aging at 100 UM (FIG. 8).

Example 3

Figures 9A, 9B, 9C:
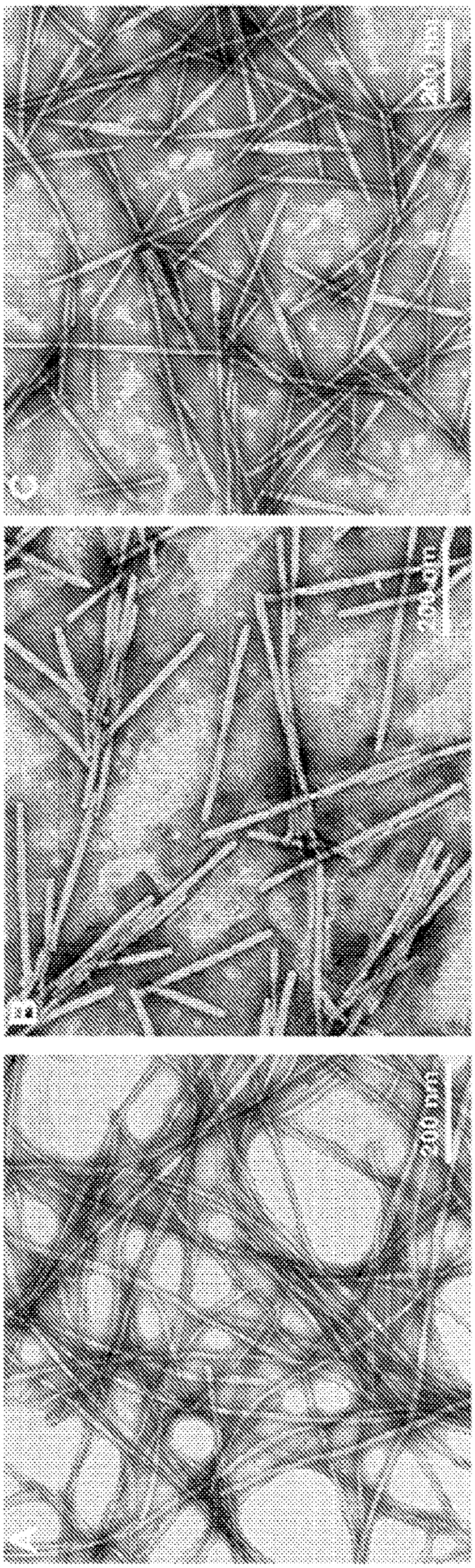
FIGS. 9A-9B show representative low magnification TEM images of EPA filaments (9A) before nebulization and after nebulization in the (9B) nebulized mist and (9C) reservoir. Filament solutions were nebulized at 500 μM in aqueous solution for 10 min. Scale bars represent 200 nm.
Figures 10A, 10B, 10C:
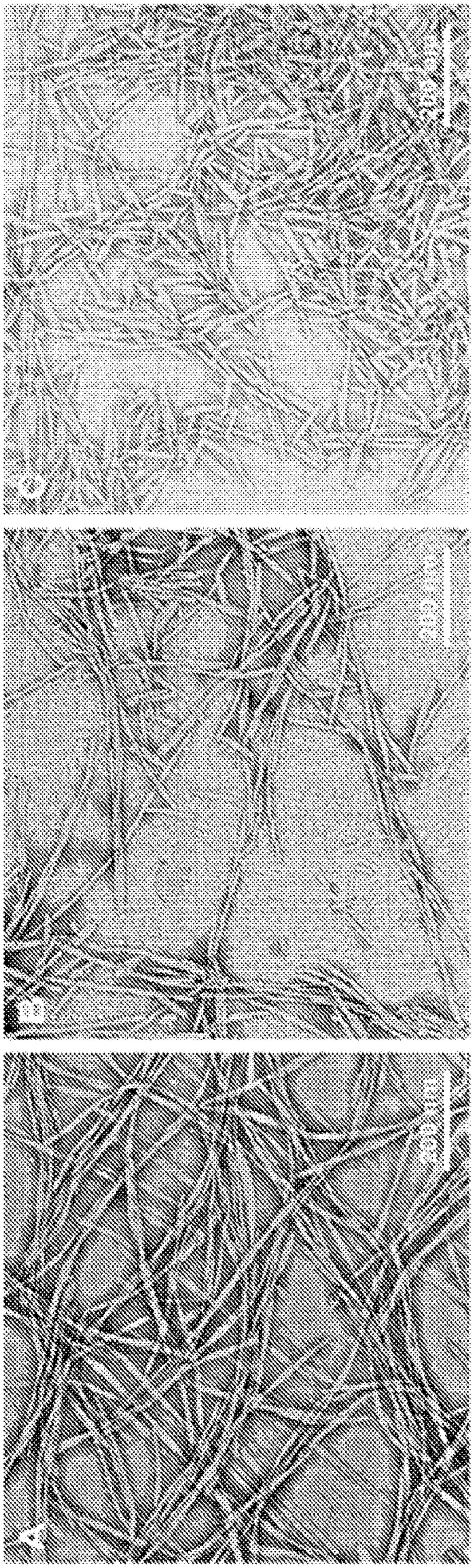
FIGS. 10A-10B show representative low magnification TEM images of OPA filaments (10A) before nebulization and after nebulization in the (10B) nebulized mist and (10C) reservoir. Filament solutions were nebulized at 500 μM in aqueous solution for 10 min. Scale bars represent 200 nm.
Figures 11A, 11B, 11C:
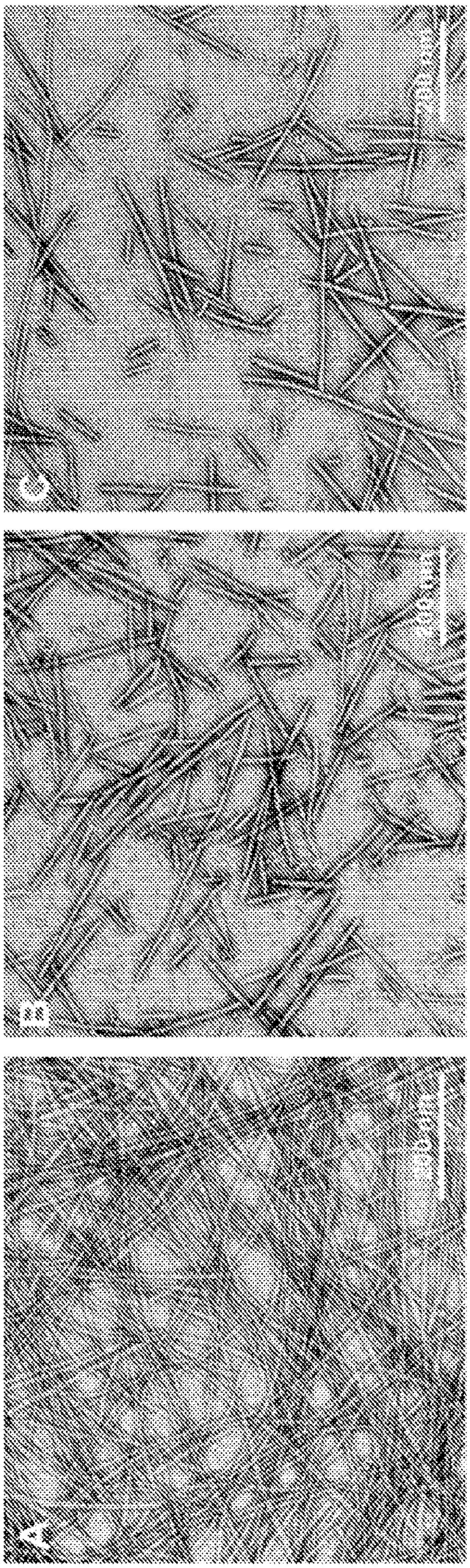
FIGS. 11A-11B show representative low magnification TEM images of KPA filaments (11A) before nebulization and after nebulization in the (11B) nebulized mist and (11C) reservoir. Filament solutions were nebulized at 500 μM in aqueous solution for 10 min. Scale bars represent 200 nm.
Figures 12A, 12B, 12C, 12D, 12E, 12F:
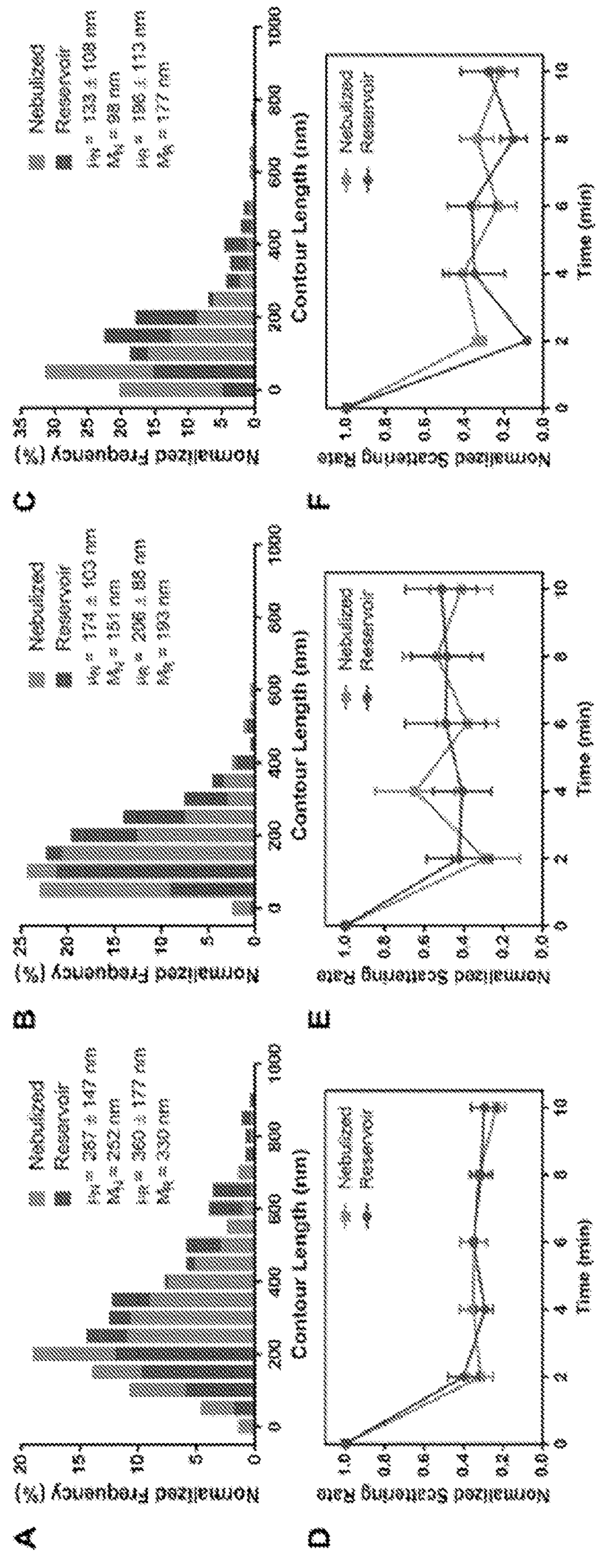
FIGS. 12A-12F are contour length reduction analyses of (12A) EPA, (12B) OPA, and (12C) KPA filaments after nebulization, comparing the nebulized (red) and reservoir (blue) populations' size distributions (20 bins, 50 nm each). Nebulized populations measured shorter on average compared to the reservoir populations. Average contour lengths (μ) given as mean±SD alongside medians (M) for each population (**p<0.0001, two-tail unpaired t test; EPA: $n_N$=316, $n_R$=316; OPA: $n_N$=311, $n_R$=339; KPA: $n_N$=377, $n_R$=369). Dynamic light scattering measurements of (12D) EPA, (12E) OPA, and (12**F) KPA over the course of a 10 min nebulization event as collected every 2 min, showing consistent filament breakdown over time. Data are normalized to molar scattering rate of filaments at t=0 min and given as mean±SD ($p>0.05$, two-way ANOVA, n=3).

Since a length reduction was observed for all three peptide-based supramolecular filament embodiments, we confirmed this phenomenon by analyzing the contour length of the filaments by tracing at least 300 structures in TEM images. Representative low-magnification TEM images of EPA, OPA, and KPA filaments before and after nebulization are provided in FIGS. 9-11. Filaments before nebulization were not measured, as accurate contour lengths could not be determined, since the filaments are over several microns long. Size distributions of the filaments for their nebulized and reservoir populations are shown in FIGS. 12A-12C. For all three systems, the nebulized population was measured to be on average shorter than its respective reservoir population. This suggests factors in play during aerosol droplet formation and delivery have a greater influence on filament size reduction compared to recycling in the reservoir. The EPA, OPA, and KPA filaments averaged around 287±147 nm, 174±103 nm, and 133±108 nm, respectively, exiting the nebulizer as a mist and around 360±177 nm, 206±88 nm, and 196±113 nm, respectively, leftover in the reservoir. For the KPA system, spherical micelles were omitted from this analysis as they bias the distribution representation toward non-filamentous structures. Additionally, we observe a correlation between filament breakdown and a transition from the negative to positive surface charge assemblies, where EPA filaments were longest in comparison to KPA filaments after nebulization, which suggests molecular design may play a role in filament breakdown.

Example 4

We next investigated whether this filament breakdown was consistent over the course of a nebulization event. We measured the molar scattering rate of the filaments with dynamic light scattering (DLS) every 2 min for a total 10 min as a measure of assembly size, as larger filamentous assemblies will scatter light more strongly than smaller ones. The molar scattering rate represents the scattering rate normalized to the sample concentration and is used here, since the DLS software uses models for fitting spherical particles and our structures are anisotropic. The EPA, OPA, and KPA filaments, as shown in FIGS. 12D-F respectively, showed consistent breakdown over the course of 10 min, where the molar scattering rate did not significantly vary over time. Moreover, the drop in molar scattering was consistent amongst the different filament systems and did not vary in value relative to the filaments before nebulization. In terms of delivering supramolecular filament systems with a jet nebulizer for treatment administration, the consistent filament breakdown over the course of a nebulization event is promising in regard to aerosol delivery, as the filaments are released reliably with a relatively uniform size drop over time from the device.

Example 5

Nebulization Impact on Molecular Packing

Figures 13A, 13B, 13C:
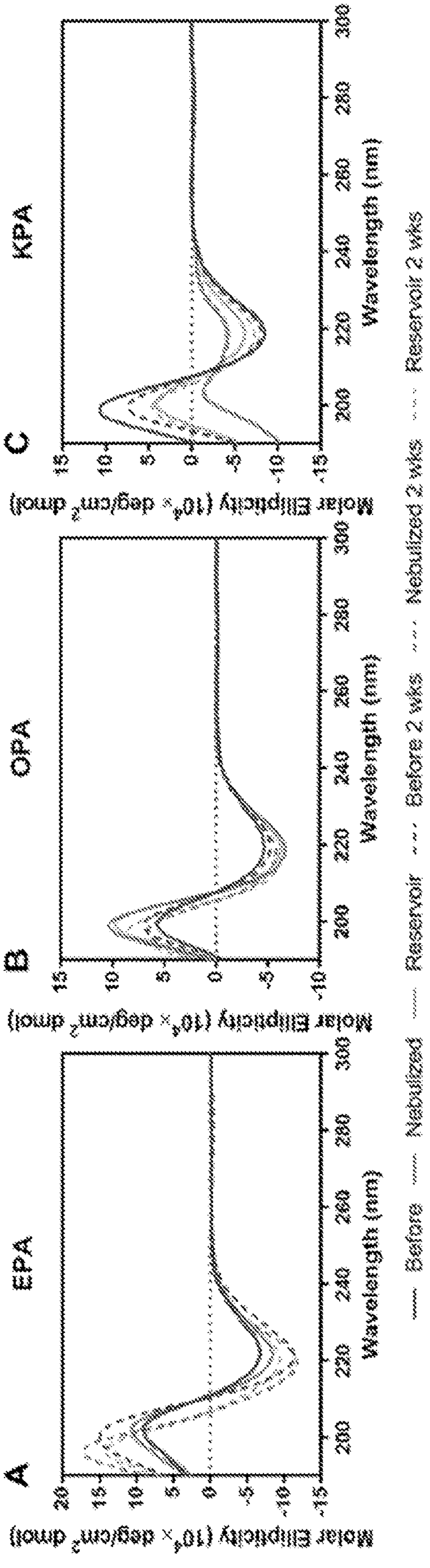
FIGS. 13A-13C show circular dichroism (CD) spectra of the supramolecular filament systems before and immediately after nebulization (solid lines) alongside the same solutions 2 weeks later (dashed lines). All filaments were nebulized at 500 UM for 10 min. Data given are mean spectra for each solution (n=3). (13A) EPA filaments before and after nebulization, showing preservation of β-sheet character during nebulization. (13B) OPA filaments before and after nebulization, showing retention of β-sheet character with a temporary increase in CD signal. (13C) KPA filaments before and after nebulization, showing a transition from β-sheet to random coil for the nebulization group and weakened β-sheet hydrogen bonding for the reservoir group.

While we were able to directly observe filament breakdown in terms of length, we investigated further the impact nebulization may have on the molecular packing of the PA monomers within the supramolecular filaments. FIG. 13 contains the representative circular dichroism (CD) spectra of the three filament systems before and after a 10 min nebulization event of both filaments that exit as mist and those leftover in the reservoir. EPA, OPA, and KPA filaments before nebulization show primarily β-sheet characteristic hydrogen bonding, as evidenced by a negative peak around 220 nm and a positive peak around 197 nm for each system. Immediately after nebulization, the EPA filaments collected in the mist exhibit a slightly increased β-sheet signal, while EPA filaments leftover in the reservoir show no change to their hydrogen bonding, as seen in FIG. 13A. As depicted in FIG. 13B, OPA filaments in both the nebulized and reservoir populations show an increased β-sheet signals, which suggests the nebulization process likely enhances the hydrogen bonding of the OPA monomers within the supramolecular filaments. This slightly contrasts from the behavior observed for the EPA filaments and is likely attributed to the potential alignment of OEG chains of OPA from aerosol formation forces, which reduces steric repulsion between OPA monomers. Conversely, the KPA filaments, as detailed in FIG. 13C, exhibit a secondary structure transition from β-sheet to random coil character in the nebulized group, as evidenced by a red-shifted negative band above 200 nm, whose shift is likely due to aromatic interactions between tyrosine residues. Moreover, the KPA reservoir group displays a weakened β-sheet signal compared to the filaments before nebulization. Altogether, the decrease in CD signal and transition to the unorganized random coil hydrogen bonding suggest partial dissociation of the KPA supramolecular filaments into smaller aggregates and/or PA monomers. This is corroborated by the morphologies observed for the KPA filaments after nebulization, as smaller worm-like micelles and spherical micelles were generated. The strength of the hydrogen-bonding network within the supramolecular filaments is evidently important in the maintenance and stabilization of β-sheet character after nebulization.

Figures 14A, 14B:
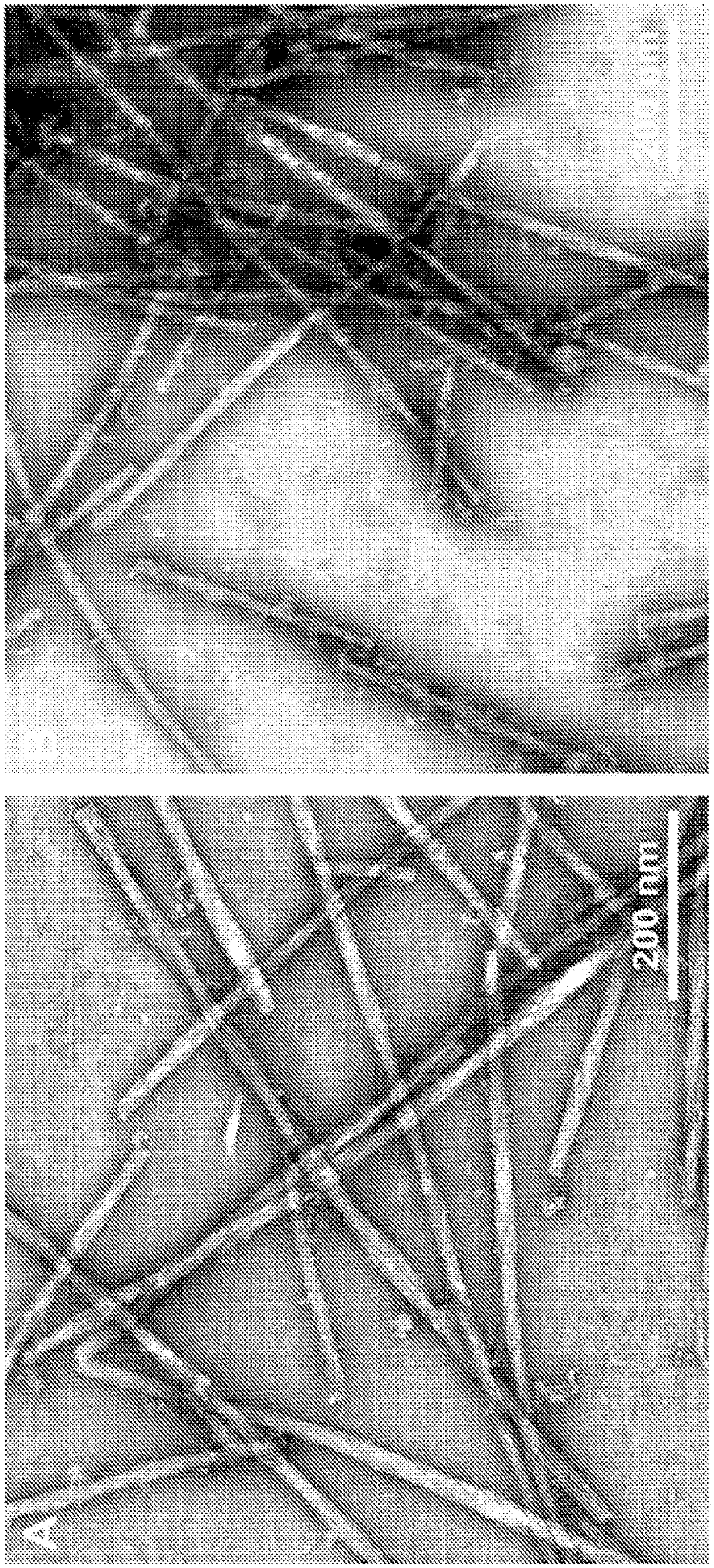
FIGS. 14A-14B show representative TEM images of EPA filaments at 500 μM in aqueous solution after ageing for 2 weeks after a 10 min nebulization event. Filaments from the (14A) nebulized mist and (14B) reservoir appear relatively unchanged compared to immediately after nebulization condition with the presence of some small aggregates. Scale bars are 200 nm.
Figures 15A, 15B:
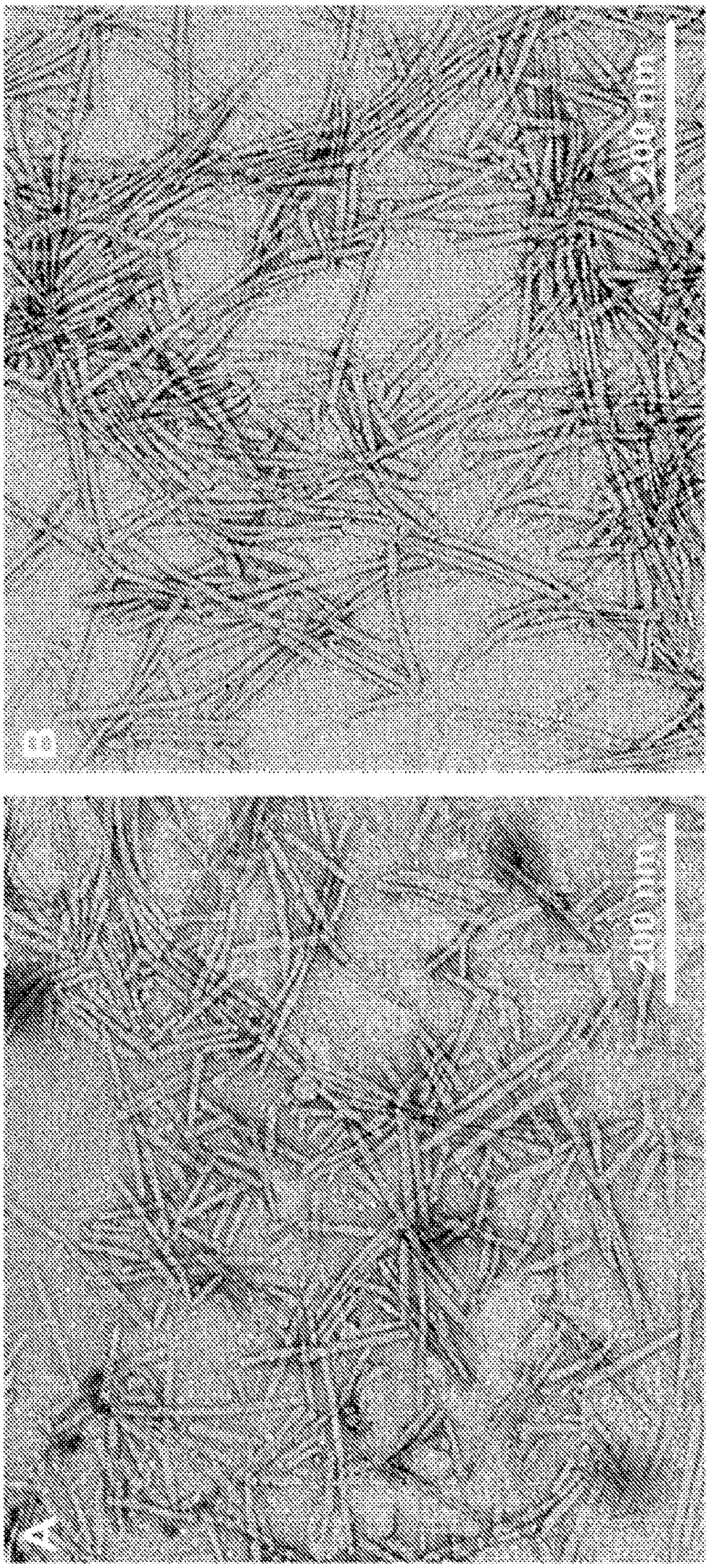
FIGS. 15A-15B show representative TEM images of OPA filaments at 500 μM in aqueous solution after ageing for 2 weeks after a 10 min nebulization event. Filaments from the (15A) nebulized mist and (15B) reservoir appear relatively unchanged compared to the immediately after nebulization condition. Scale bars are 200 nm.
Figures 16A, 16B, 16C, 16D:
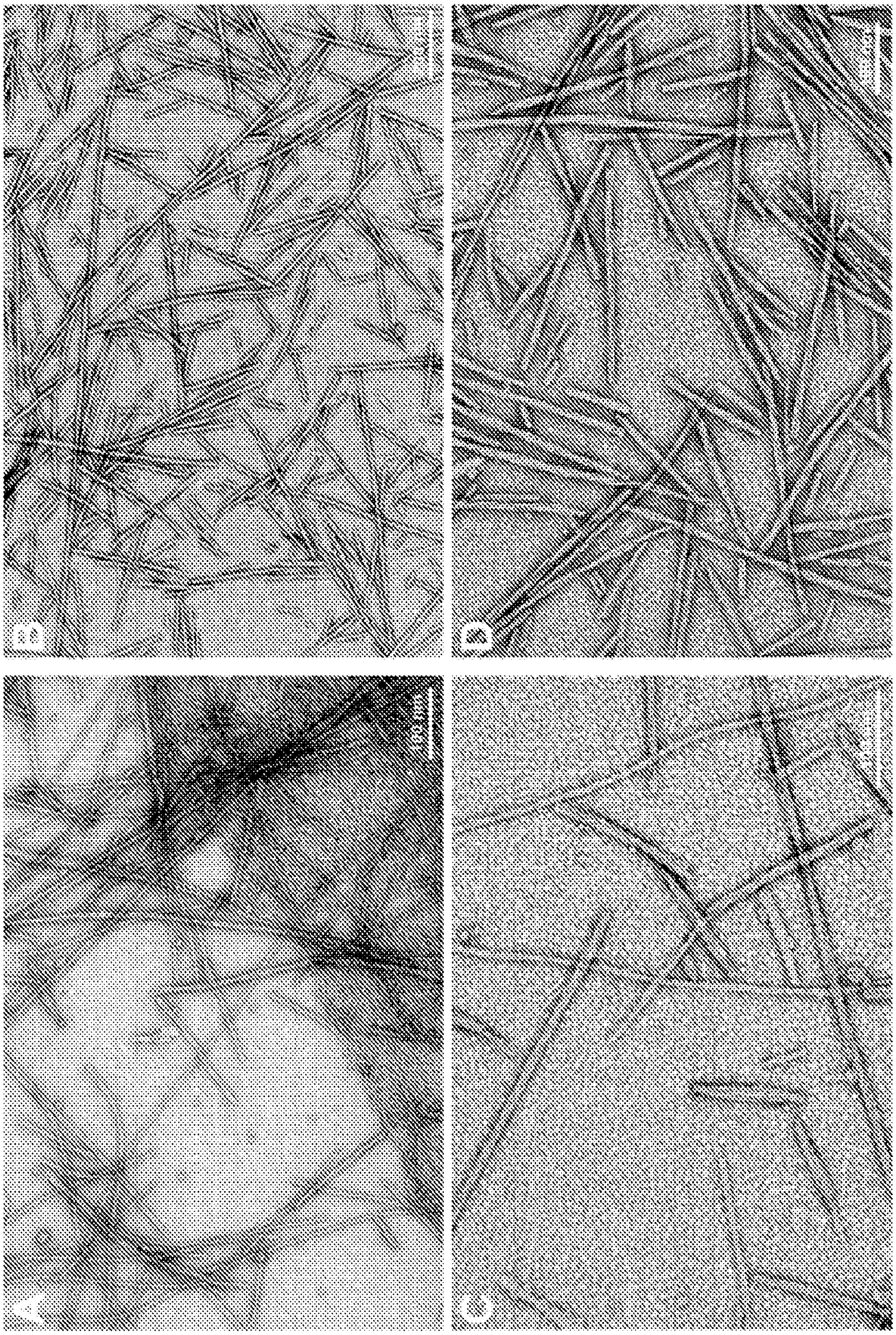
FIGS. 16A-16D show representative TEM images of KPA filaments at 500 μM in aqueous solution after ageing for 2 weeks after a 10 min nebulization event. Structures from the (16A, 16C) nebulized mist and (16B, 16D) reservoir appear relatively unchanged compared to the immediately after nebulization condition. Lower magnification (16A, 16B) and higher magnification (16C, 16D) show the presence of the fibrils, worm-like micelles, and spherical micelles. Alongside the circular dichroism measurements (FIG. 13C), the presence of these structures suggests nebulization induced a conformational change in assembly to a metastable state.

To gain insight into the thermodynamic stability of the new assembly states induced by nebulization, we analyzed the CD signal of the same filament solutions after nebulization after aging for an additional 2 weeks in solution at room temperature. As shown in FIGS. 13A and 13B, the EPA and OPA filaments maintained their β-sheet character with negligible variability in molar ellipticity between the before and after nebulization groups. Moreover, the OPA filaments, which originally showed a sharp increase in β-sheet signal, returned to levels comparable to the before control filaments, suggesting the enhanced hydrogen bonding was temporary and not reflective of a more thermodynamically stable state. Additionally, the shorter EPA and OPA filaments are still observed in the nebulized and reservoir groups with TEM imaging after 2 weeks (FIGS. 14 and 15). As depicted in FIG. 13C, the KPA filaments 2 weeks later continued to display the weakened β-sheet signal in the reservoir group and the random coil character of the nebulized group. Since a transition back to β-sheet character is not observed for the nebulized group, it is likely that nebulization induces the formation of new metastable assemblies of the KPA monomers, which is corroborated by TEM images of the KPA filaments 2 weeks after nebulization, as the fibril, worm-like micelle, and spherical micelle structures are still observed (FIG. 16). Collectively, these results give insight into the impact nebulization induces on the hydrogen bonding within peptide-based supramolecular filaments and suggests that nebulization into aerosol droplets greater influences molecular packing compared to repeated recycling within the reservoir of the nebulizer device.

Example 6

Mechanism of Filament Breakdown in Aerosols.

Figures 17A, 17B, 17C:
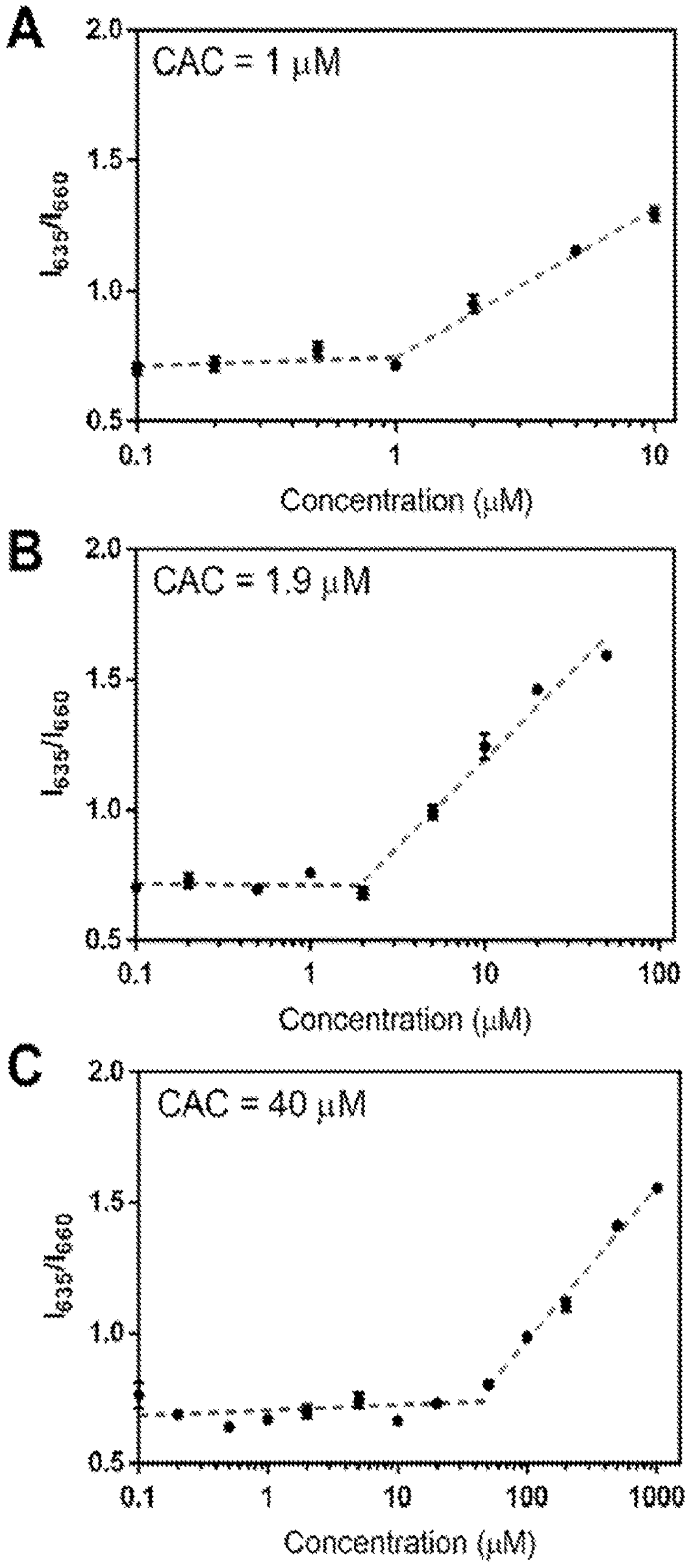
FIGS. 17A-17C depict the critical assembly concentration (CAC) of (17A) EPA, (17B) OPA, and (17C) KPA molecules in water as measured from a Nile Red assay. A fluorescence intensity maximum is shifted from a wavelength of 660 nm to 635 nm as Nile Red dye becomes encapsulated within the supramolecular structures of the peptide amphiphiles (PAs). Blue line represents region of concentrations where Nile Red remains in solution; red line represents region where Nile Red is encapsulated. Data are given as mean±SD (n=3).
Figures 18A, 18B, 18C:
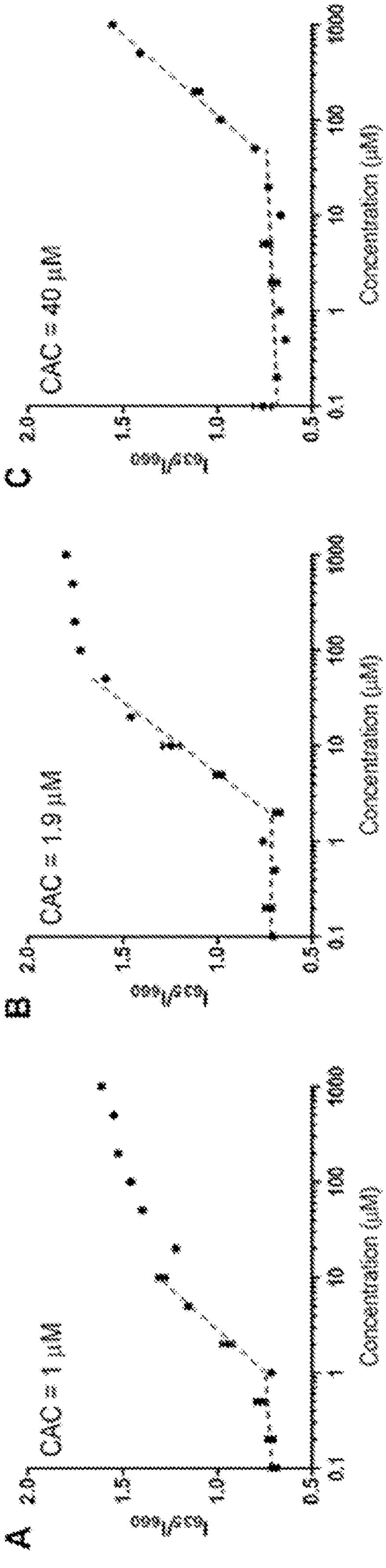
FIGS. 18A-18C depict the critical assembly concentration (CAC) of (18A) EPA, (18B) OPA, and (18C) KPA molecules in water as measure from a Nile Red Assay. Data presented in FIG. 17A-C are also represented here but showing full range of concentrations tested from 0.1 μM to 2 mM.

Based on our observations from our TEM and CD studies, we sought to elucidate the aspects of the molecular design and self-assembly of the supramolecular filaments that influences their behavior during aerosol delivery, as the KPA filaments exhibited distinctly different morphological transitions and hydrogen bonding disruption after nebulization compared to the EPA and OPA filaments. Therefore, we assessed the thermodynamic stability of each supramolecular filament system by measuring their critical assembly concentration (CAC) using a Nile Red assay. As shown in FIGS. 17A-C, the CAC values of EPA, OPA, and KPA were measured to be 1 μM, 1.9 μM, and 40 μM, respectively. Data from the Nile Red assay are given in full in FIG. 18. The differences in CAC between the different PAs are likely reflective of differences in electrostatic repulsion between the charged groups of EPA and KPA and steric effects with respect to the size of the OEG groups of the OPA molecule.[74] We find a direct correlation between the CAC value and nebulization stability of the supramolecular filaments with respect to nanostructure integrity and hydrogen bonding interactions. The EPA and OPA filaments with low CAC values exhibited morphological retention with reduced length and with unaltered to increased hydrogen bonding; in contrast, the KPA filaments with a high CAC value underwent notable filament breakdown with a morphological transition and disruption of the hydrogen bonding network within the supramolecular structures. As the CAC value represents the propensity of the monomer units to aggregate in solution, increasing the strength of hydrophobic interactions alongside other non-covalent interactions through molecular engineering can result in lower CAC systems, and thus create supramolecular filament systems with enhanced stability during aerosol formation.

Example 7

Previous research has been conducted to assess protein and peptide stability during aerosolization for therapeutic applications, which conclude that air-liquid interface (ALI) interactions are the major contributing driving force for their denaturation and aggregation with some influence from shear stress. The formation of liquid aerosols creates droplets with very high surface area-to-volume ratios and thus exposes molecules within the droplets to a highly hydrophobic ALI; this hydrophobic interaction leads to enrichment of surface active and amphiphilic moieties at the interface. Our results suggest that enrichment at the ALI is the major driving force for PA monomer depletion and their respective supramolecular filament degradation during nebulization. This conclusion is particularly corroborated by CD measurements between KPA filaments within the nebulized and reservoir groups (FIG. 13C). The nebulized group, which experiences the greatest ALI interactions, exhibits complete disruption of its β-sheet character, whereas the reservoir group, which experiences lesser ALI interactions and more agitation from repeated recycling within the device, exhibits only weakened β-sheet hydrogen bonding.

While factors like agitation and shear stress may also contribute to the fragmentation of these systems, these are insignificant compared to the ALI, as the TEM analysis of the contour lengths of the filaments would likely be similar for the nebulized and reservoir populations if these factors played a major role.

Figure 19:
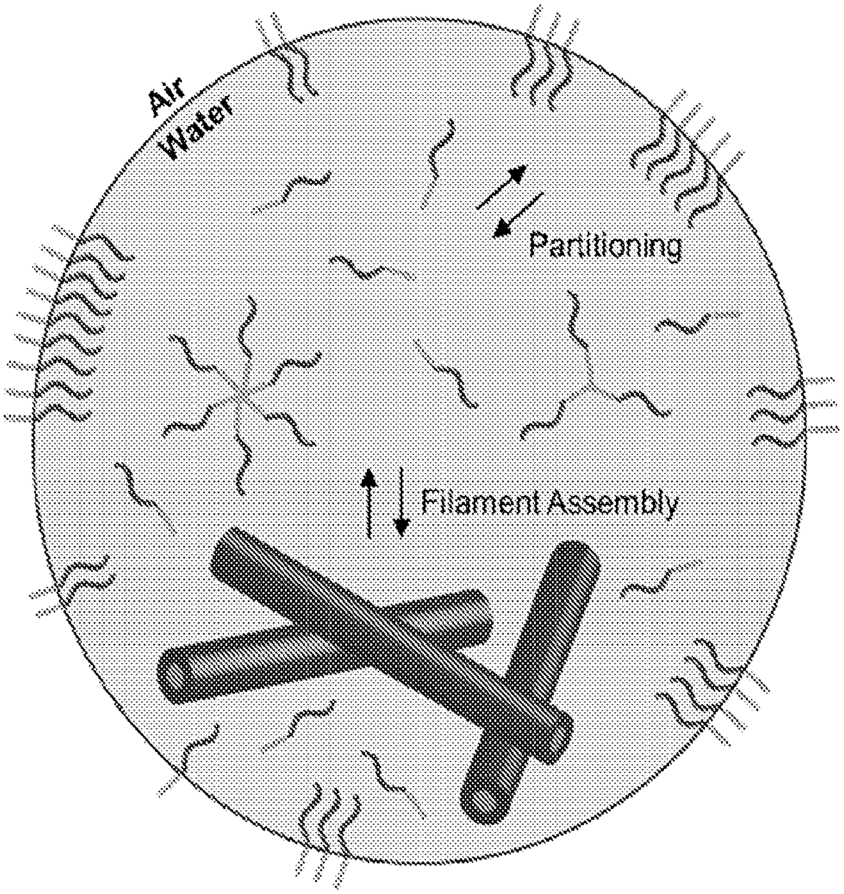
FIG. 19 depicts a scheme for the proposed mechanism of supramolecular filament enrichment at the air-liquid interface (ALI) during liquid aerosol formation from a jet nebulizer. PAs, once exposed to the hydrophobic ALI, may shift the assembly-disassembly equilibrium from their supramolecular structure into the surrounding solution as monomers are drawn from solution to the ALI. The PA monomers may reassemble at this stage into the filaments or partition and enrich the ALI, where their hydrophobic domain (green) is exposed to air and their hydrophilic domain (blue) to water. Each step of the proposed mechanism is reversible and the tendency for PA monomers to remain within their assembled state is dictated by the strength of their non-covalent interactions, which correlates with their CAC value.

As depicted in the scheme in FIG. 19, we propose that peptidic supramolecular filaments interact with the ALI through a two-step mechanism: filament disassembly and subsequent partitioning at the ALI. Peptide amphiphiles exchange frequently between their assembled state and the ALI through their monomeric form in solution, where the strength of hydrophobic and non-covalent interactions within the supramolecular filament compared to the hydrophobic interactions at the ALI influence the partitioning fate of monomeric units during aerosolization. Together, these steps account for the observed filament fragmentation and disruptions to the internal hydrogen bonding of the PA monomers within the filaments: monomers are depleted from the bulk solution to subsequently enrich the ALI, which lowers their concentration in the bulk, and as the CAC is approach, filaments will fragment to replenish the monomer concentration within in the bulk. The surface activity of these molecules at the ALI is further corroborated by the observed foam generation during a nebulization event, suggesting enrichment of monomeric units at the interface. Therefore, through tuning of the molecular design of peptide amphiphile units, particularly through modifications of the C-terminal charge-bearing residues of the peptide sequence, we can influence the degree of filament disruption during nebulization by constructing systems with high stability, as reflected through their CAC value.

Example 8

Drug Encapsulation and Nebulizer Release.

Figures 20A, 20B, 20C:
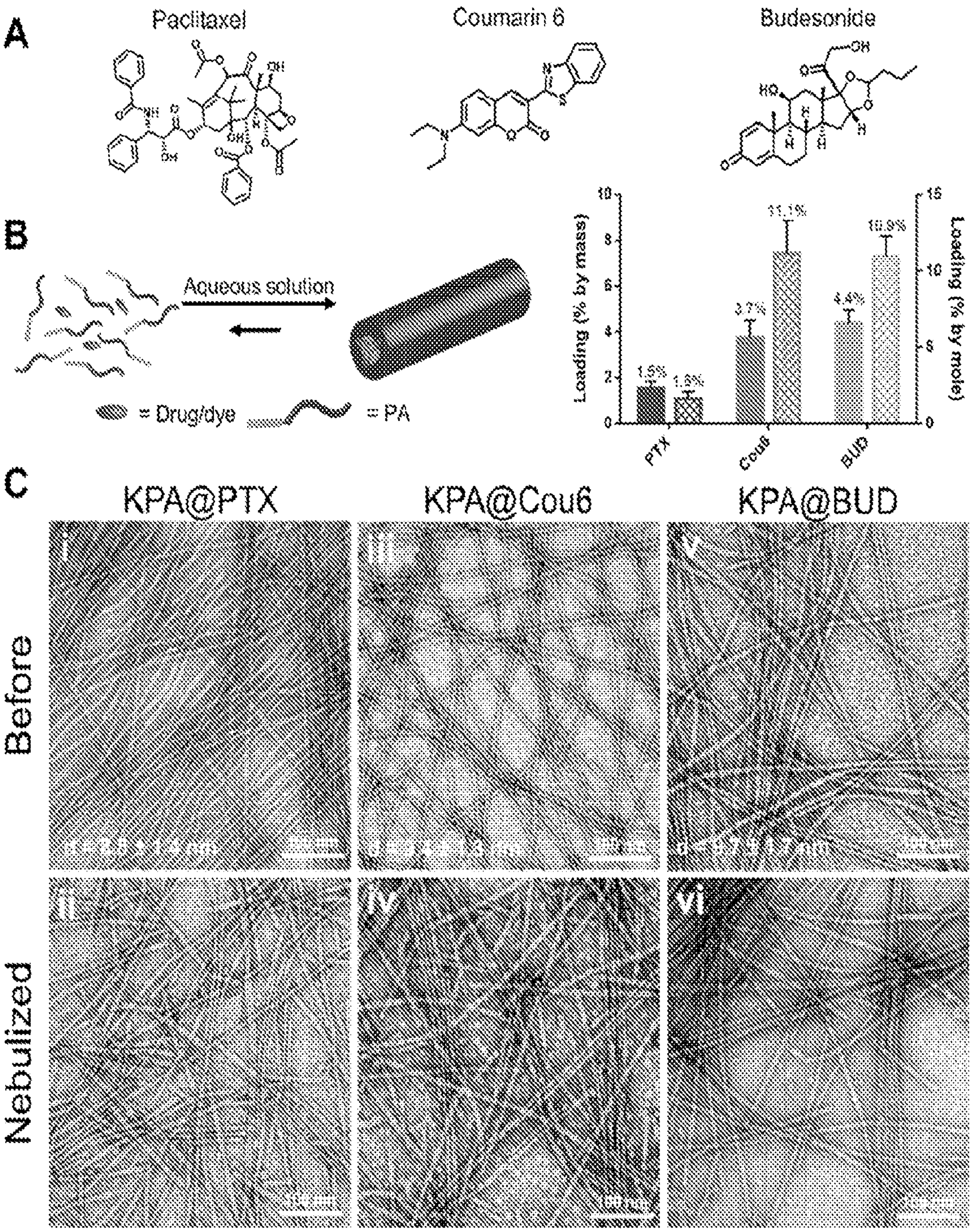
FIGS. 20A-20C show (20A) the molecular structure of the lung disease-relevant drugs and fluorescent dye used in loading within the supramolecular filaments: paclitaxel (PTX, MW=853.92 g/mol), the anticancer drug; coumarin 6 (Cou6, MW=350.44 g/mol), the green fluorescent dye; and budesonide (BUD, MW=430.54 g/mol), the anti-inflammatory glucocorticoid used to treat symptoms of asthma and chronic obstructive pulmonary disease (top). (20B) The encapsulation process of hydrophobic drugs and dyes within supramolecular peptide amphiphile (PA)-based filaments, where dissolution of PA monomers and drug/dye in aqueous solutions results in their self-assembly with the drug/dye loaded within the hydrophobic core (left). The loading capacity of PTX, Cou6, and BUD based on mass (left axis, solid bars) and mole (right axis, checkered bars) percent within KPA supramolecular filaments (right). Data are given as mean±SD (n=5). (20C) Representative transmission electron microscopy (TEM) images of KPA filaments loaded with PTX (i, ii), Cou6 (iii, iv), and BUD (v, vi) before and after nebulization at 500 μM. Diameters are given as mean±SD (n=35). The before images (after aging for 24 hr) show filamentous nanostructures over several microns in length; the nebulized images, representing filaments collected in aerosol mist released from a jet nebulizer immediately after a nebulization event, show a retained filament morphology shorter in length and the appearance of spherical micelles, indicating that loaded drugs/dyes help to stabilize the supramolecular structures during aerosol generation.

With better insight into nebulization stability and the mechanism of supramolecular filament breakdown, we next sought to assess whether these systems can successfully carry drugs and dyes within aerosol droplets for potential inhalation-based therapies. Additionally, we investigated if encapsulation of drugs would influence the stability of the supramolecular structures during nebulization. We chose paclitaxel (PTX), an anticancer drug approved for lung cancer treatment, coumarin 6 (Cou6), a green fluorescent dye, and budesonide (BUD), a corticosteroid used to alleviate symptoms of asthma and chronic obstructive pulmonary disease, to encapsulate within KPA filaments, as influences on structural stability would be most obvious with the least stable system. FIG. 20A depicts the molecular structure of these three drugs and dye. As depicted in FIG. 20B, we dissolved PA monomers with these lung disease-relevant drugs and fluorescent dye in water to encapsulate them within the hydrophobic core of the resulting supramolecular structures. FIG. 20B contains the loading capacities (% by mass or mole) of each drug and dye within the KPA filaments with 1.5%, 3.7%, and 4.4% loading by mass for PTX, Cou6, and BUD, respectively. The increase in loading capacity for Cou6 and BUD compared to PTX is likely a result of their relatively smaller size/molecular weight.

Figures 21A, 21B:
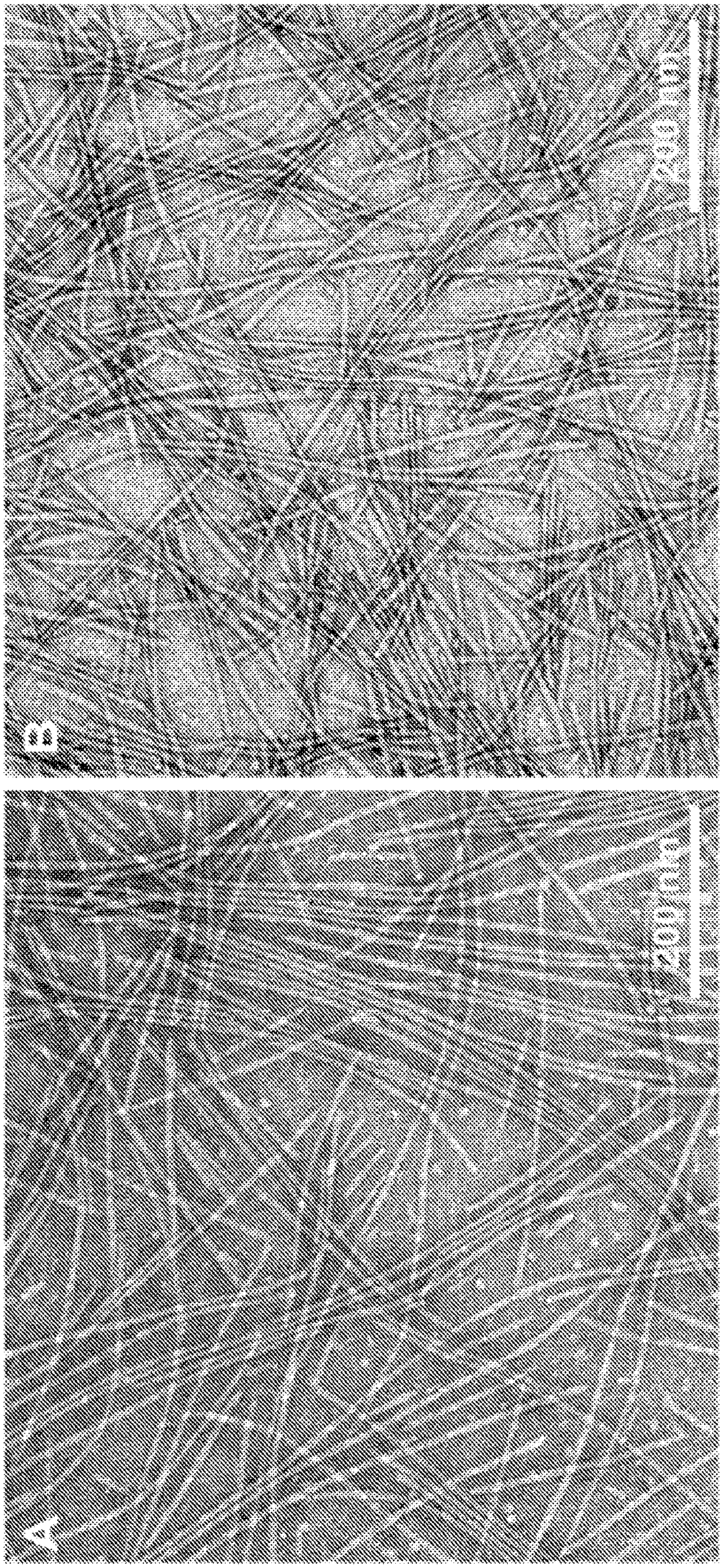
FIGS. 21A-21B show representative low magnification TEM images of paclitaxel (PTX)-loaded KPA filaments at 500 μM in aqueous solution (21A) before nebulization and (21B) after nebulization in the emitted mist. Nebulization induces filament breakdown and spherical micelle formation, but encapsulation of the hydrophobic PTX mitigates the length reduction, suggesting the additional hydrophobic interaction stabilize the filamentous structures. Scale bars are 200 nm.
Figures 22A, 22B:
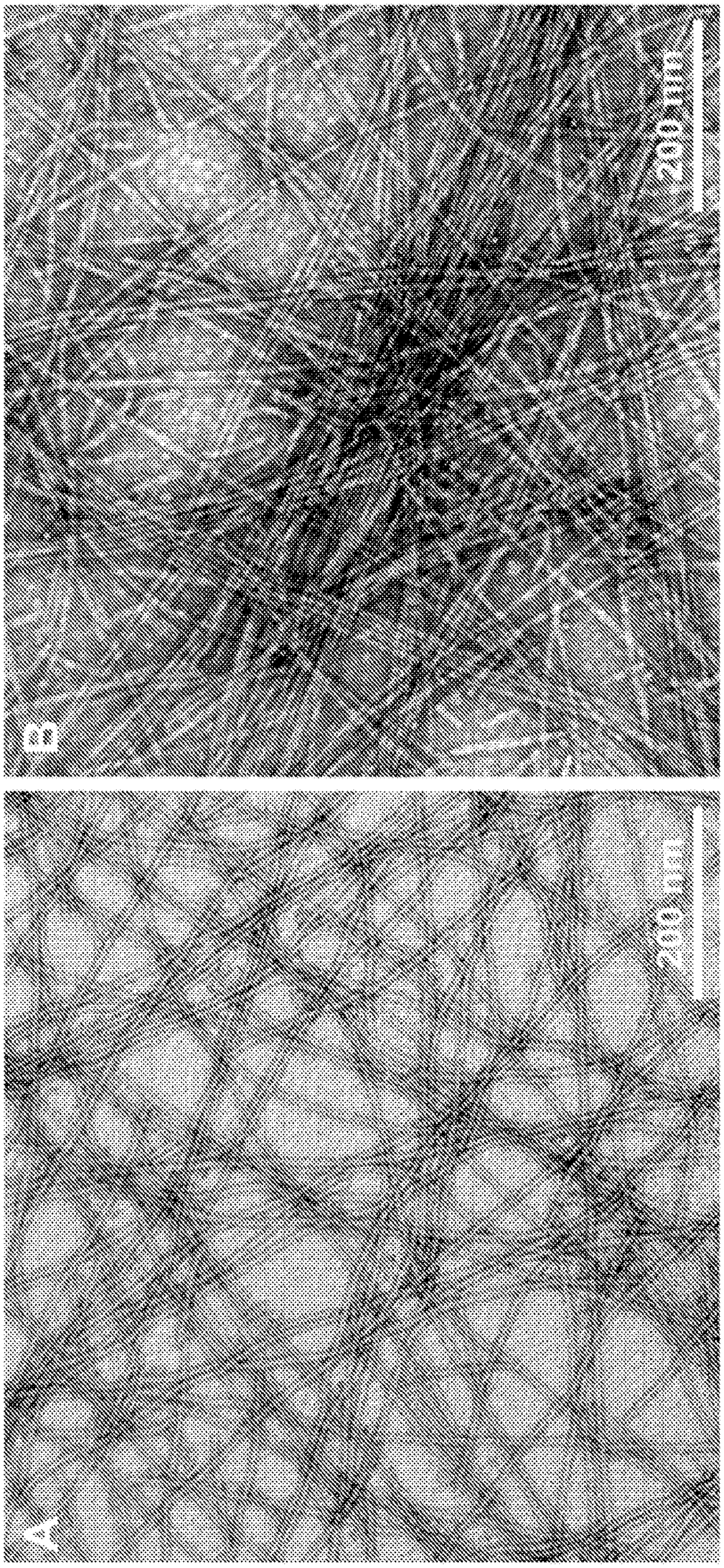
FIGS. 22A-22B show representative low magnification TEM images of coumarin 6 (Cou6)-loaded KPA filaments at 500 μM in aqueous solution (22A) before nebulization and (22B) after nebulization in the emitted mist. Nebulization induces filament breakdown and spherical micelle formation, but encapsulation of the hydrophobic Cou6 mitigates the length reduction, suggesting the additional hydrophobic interaction stabilize the filamentous structures. Scale bars are 200 nm.
Figures 23A, 23B:
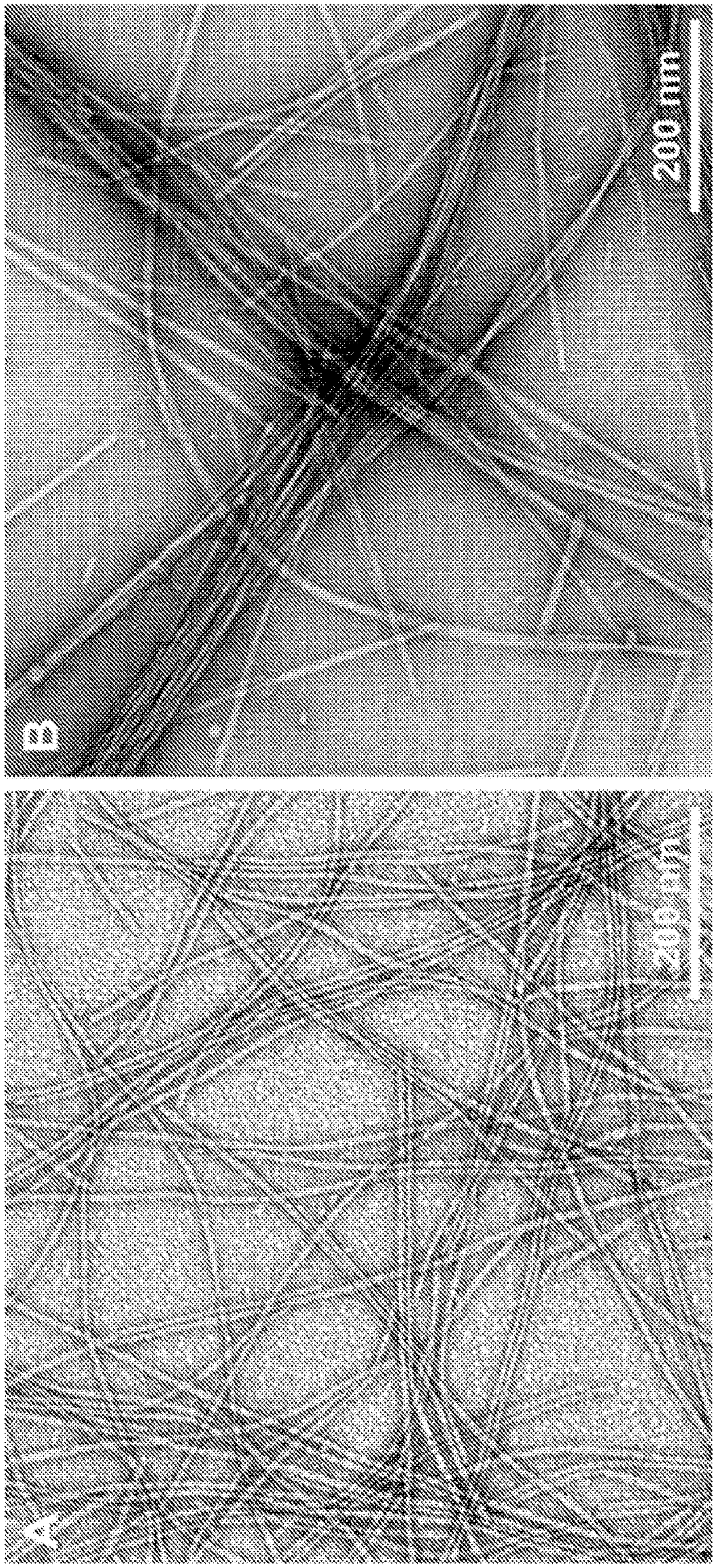
FIGS. 23A-23B show representative low magnification TEM images of budesonide (BUD)-loaded KPA filaments at 500 μM in aqueous solution (23A) before nebulization and (23B) after nebulization in the emitted mist. Nebulization induces filament breakdown and spherical micelle formation, but encapsulation of the hydrophobic BUD mitigates the length reduction, suggesting the additional hydrophobic interaction stabilize the filamentous structures. Scale bars are 200 nm.

After encapsulation, we used TEM imaging to confirm self-assembly of the system into filamentous nanostructures. As shown in FIG. 20C, all three encapsulated molecules within KPA assemblies resulted in the formation of filaments over several microns long (FIG. 20Ci, iii, and v), which measured slightly larger in diameter on average compared to unloaded KPA filaments (FIG. 6G) likely as a result of drug/dye loading. The loaded filaments were then nebulized and representative TEM images of the resultant structures are shown in FIG. 20Cii, iv, and vi. Low magnification images of the two groups for the three loaded drugs/dyes are displayed in FIGS. 21-23. Notably, we observed a distinct difference compared to unloaded KPA filaments after nebulization (FIG. 6H); the observed loaded filaments maintain their fiber morphology and reduce in length, but this size reduction in noticeably smaller in comparison to the unloaded filaments. Spherical micelles are still observed, but the fibril and worm-like structures are not. These results suggest that the encapsulation of drugs/dyes within the filaments enhances their structural stability and thus helps maintain their filamentous shape, likely due to strengthened hydrophobic interactions between the loaded moiety and surrounding PA molecules within the filament core. Moreover, these results give credence to our proposed mechanism of the ALI enrichment as the major driving force for filament fragmentation, as the same level of fragmentation should be observed for the loaded and empty KPA filaments if shear forces were the main factor. In terms of delivering therapeutics in an aerosol, this presents an effective strategy for improving structural stability of supramolecular peptide-based assemblies during nebulization.

Example 9

Figures 24A, 24B, 24C, 24D, 24E, 24F:
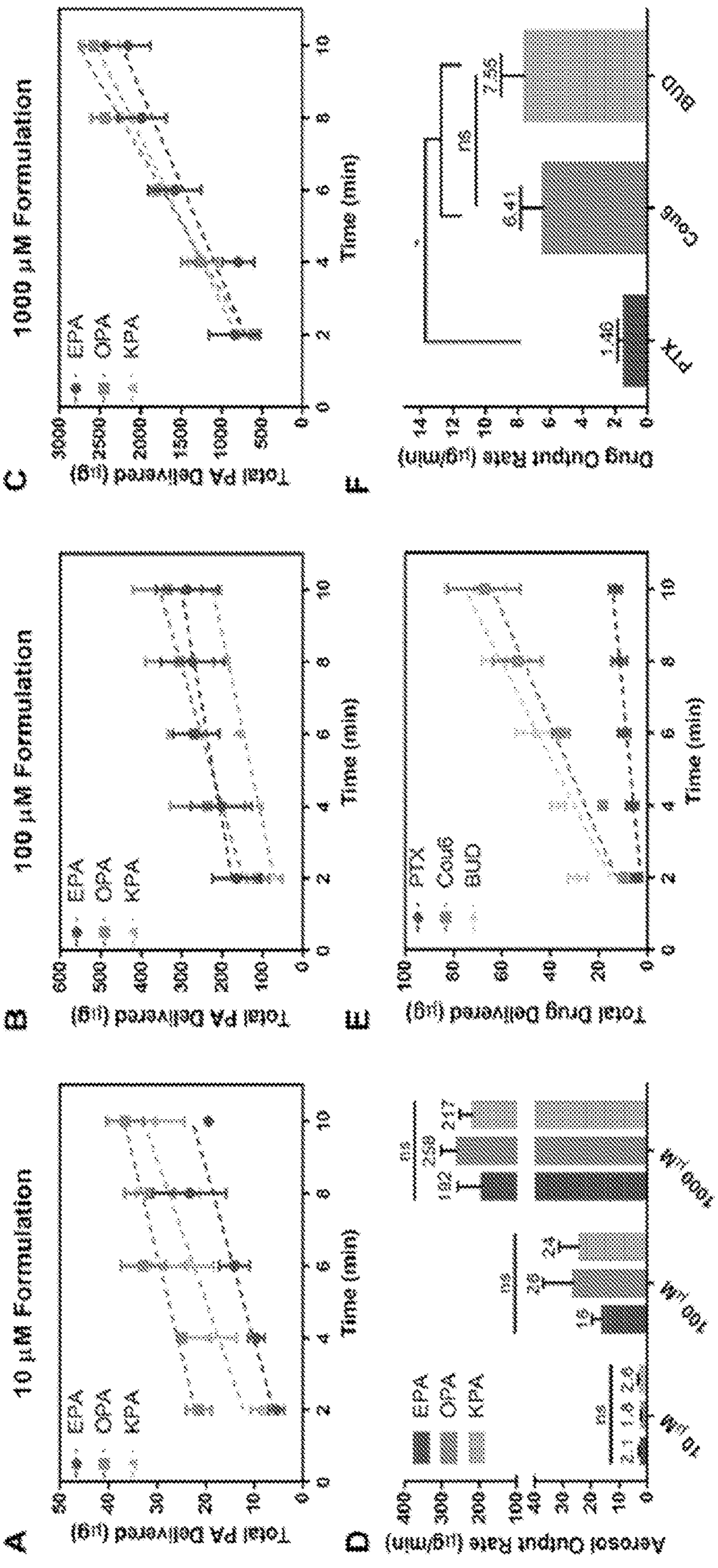
FIGS. 24A-24F are jet nebulizer release profiles of EPA, OPA, and KPA supramolecular filaments with starting formulation concentrations at (24A) 10 μM, (24B) 100 μM, and (24C) 1000 μM, showing a linear release pattern for each system over the course of a 10 min nebulization event (3 mL solution). Data given represent mean #SD (n=3); dashed lines represent line of best fit from linear regression analysis. (24D) The aerosol output rate (μg/min) of the supramolecular filaments from a jet nebulizer at different formulation concentrations, showing no statistically significant difference (ns) between filaments at the same concentration and output rate scales linearly with increasing concentration. Data are given as mean±SD ($p>0.05$ amongst filament systems, **$p<0.0001$ amongst concentrations, two-way ANOVA, n=3). (24E) The drug and dye release profiles of paclitaxel (PTX), coumarin 6 (Cou6), and budesonide (BUD) loaded within KPA filaments (1 mM) from a jet nebulizer, showing a linear release profile for each encapsulated molecule over the course of a 10 min nebulization event (3 mL solution). Data are given as mean±SD (n=3); dashed lines represent line of best fit from linear regression analysis. (24**F) The aerosol output rate of the encapsulated drugs and dye within KPA filaments (1 mM) from a jet nebulizer, where output rate reflects loading capacity. Data are given as mean±SD (ns $p>0.05$, *$p<0.05$, two-tailed unpaired t test, n=3).

We next monitored the release pattern of the supramolecular filaments in aerosol droplets from a jet nebulizer device alongside the output rate. First analyzing the blank EPA, OPA, and KPA filaments, 3 mL solutions of the filaments were loaded into a jet nebulizer at varying concentrations and the remaining concentration of PA molecules and fluid weight loss were monitored over the course of a 10 min nebulization event. FIGS. 24A-C represents the measured release profile of the three filament systems at 10 UM, 100 μM, and 1000 μM, respectively. We observed a linear release rate for all three systems over the course of 10 min. The total percentage of starting fluid released from the nebulizer is detailed in FIG. 25, where regardless of filament system or starting concentration, roughly 60-70% of the fluid is emitted from the nebulizer over 10 min. This is consistent with typical dead volumes commonly reported for jet nebulizers and suggests that changes in surface tension and viscosity with the varying concentrations are not significant enough to heavily impact output. Moreover, for each run, we observe a slight decrease in formulation fluid and total PA delivered after the 8 min time point, which corresponds to sputtering from the nebulizer as the dead volume is approached. Comparing the output rates of the filament systems, as shown in FIG. 24D, we observe that the output rate of the PAs (μg/min) scale linearly with the increasing formulation concentrations. For the same formulation concentration, we observe no statistically significant difference between the output rates of each system, suggesting that neither filament surface charge nor stability influence filament output, thus the nebulizer device itself is likely the more influential factor in output rate.

Figures 25A, 25B, 25C:
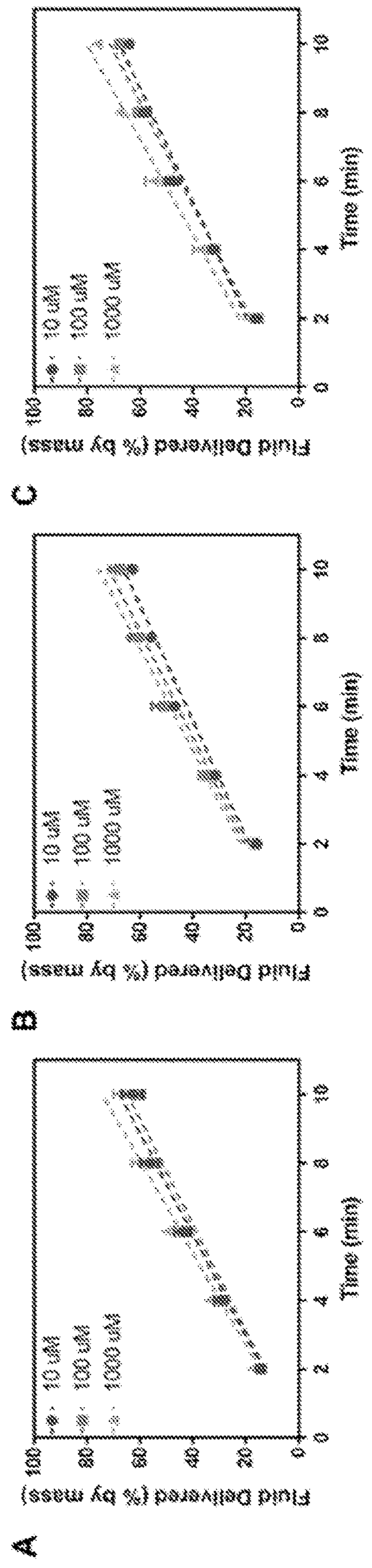
FIGS. 25A-25C depict fluid release from a jet nebulizer containing solutions of (25A) EPA, (25B) OPA, and (25C) KPA filaments at various concentration (10 μM, 100 μM, and 1000 μM) over the course of a 10 min nebulization event. Fluid delivered represented as % by mass based on a starting volume of 3 mL in the reservoir of the device as determined via gravimetric analysis. Differences between formulation concentrations and molecular design are negligible, suggesting changes in surface and tension and viscosity between the concentrations are insignificant and the nebulizer device choice is likely the determining factor for fluid output. Data are given as mean±SD (n=3).
Figures 26A, 26B:
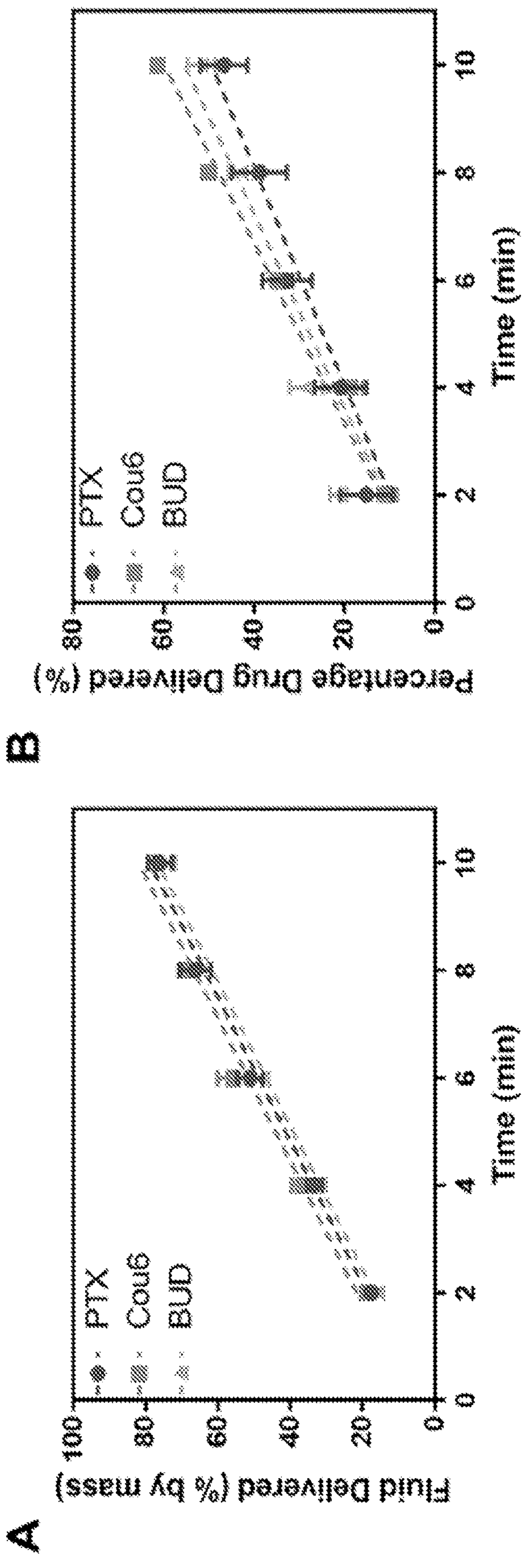
FIGS. 26A-26B depict (26A) the fluid release curve for the drug/dye-loaded KPA filaments at 1 mM in aqueous solution over the course of a 10 min nebulization event starting with 3 mL of solution in a jet nebulizer, showing negligible differences in fluid output (% by mass) between the different loading systems and thus further suggesting fluid output is likely device-dictated. (26B) The total drug delivered from a jet nebulizer (% by mass) over the course of a 10 min nebulization event relative to the starting concentration of drug/dye within the KPA filaments. Differences between the different loading systems are negligible, further suggesting device choice is the critical factor in aerosol output. Differences in aerosol output between the fluid and the loaded drugs/dye suggests that concentration of the loaded moieties and their PA carrier varies amongst emitted droplets and thus filament output is nonhomogeneous over the course of a nebulization event. Data are given as mean±SD (n=3).
Figure 27:
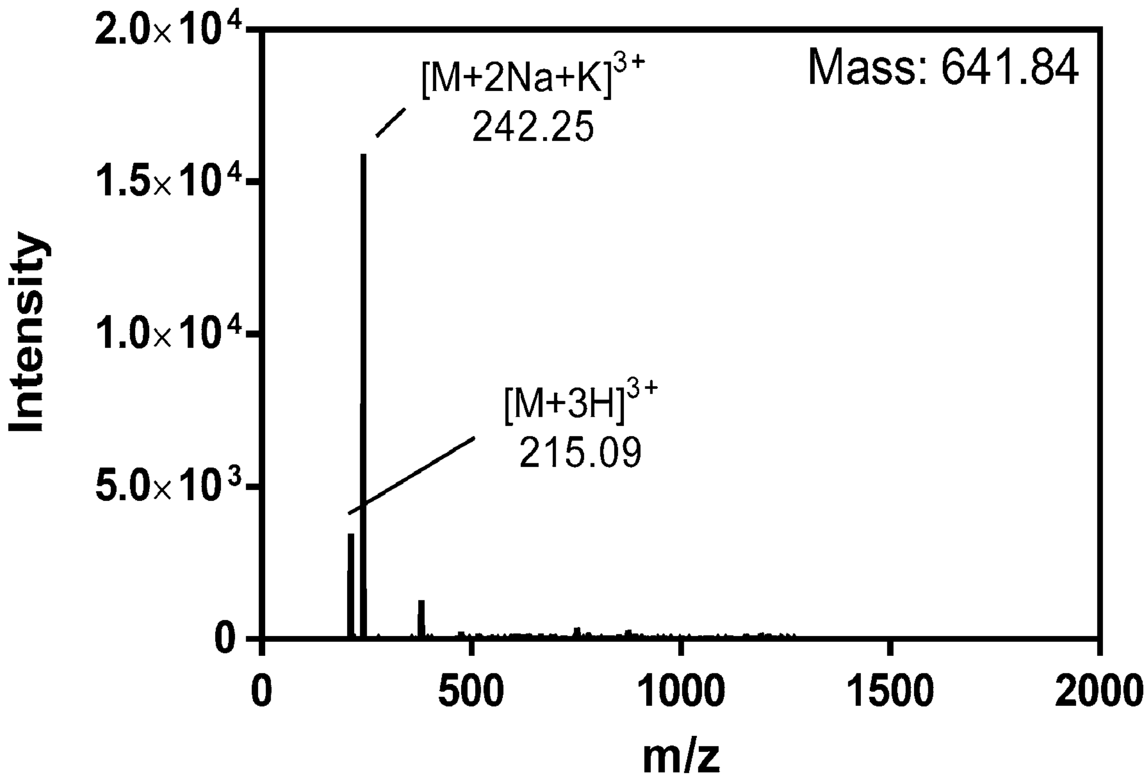
FIG. 27 depicts an ESI mass spectrum of budesonide C2 ester (BUD-buSS) after purification, indicating successful synthesis by confirmation of the correct molecular weight.
Figures 28A, 28B, 28C, 28D, 28E:
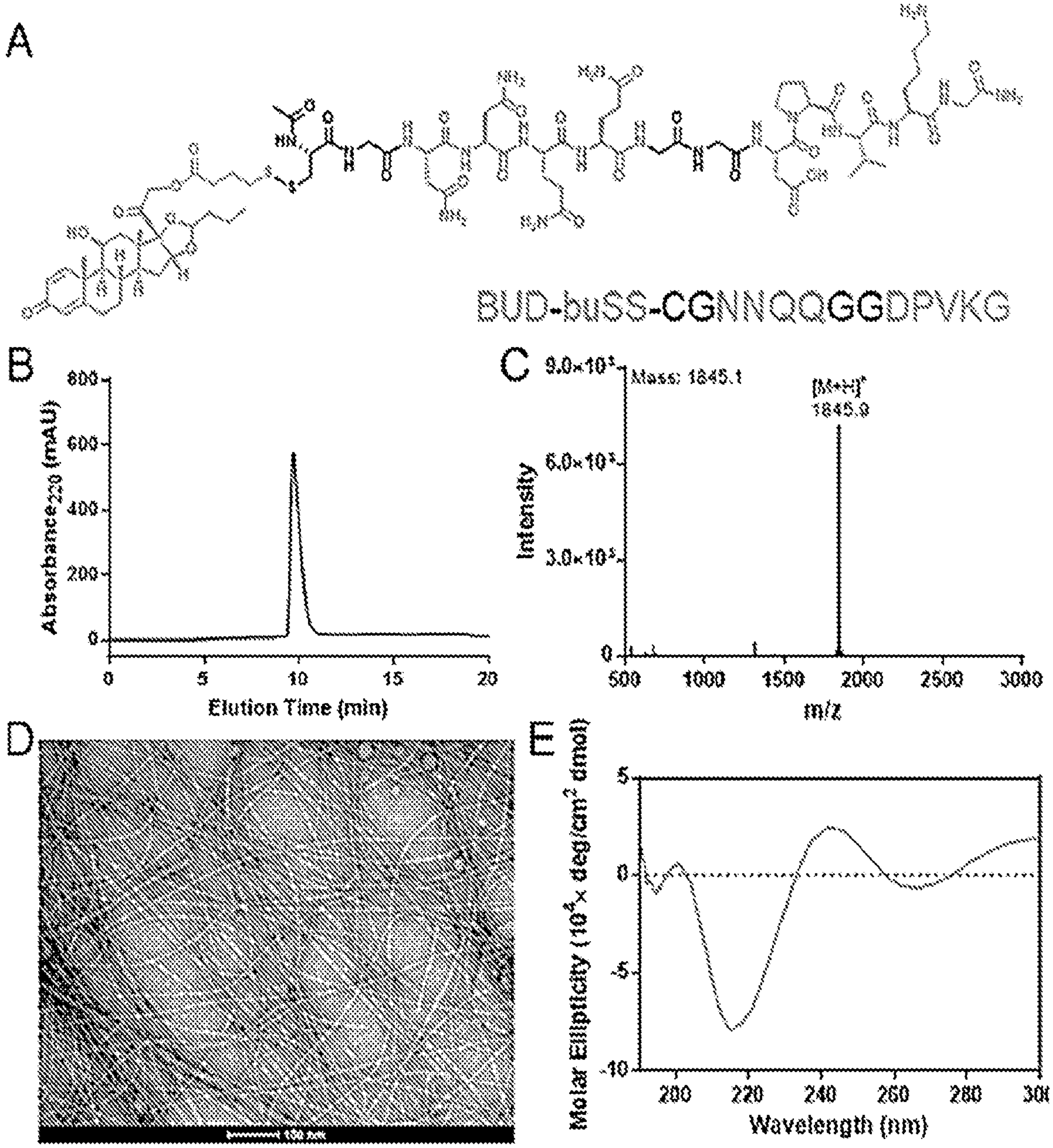
FIGS. 28A-28E: (28A) Chemical structure of budesonide-based drug amphiphile CAB-1, where molecular design is composed of hydrophobic drug budesonide (red) and a hydrophilic peptide, which contains a β-sheet regulating sequence (blue) to promote formation of 1D nanostructures and an anti-inflammatory sequence (pink) to enhance anti-inflammatory efficacy. (28B) Analytical RP-HPLC chromatogram of CAB-1, showing high purity after synthesis. (28C) MALDI-TOF mass spectrum of purified CAB-1, confirming correct molecular weight. (28D) Representative transmission electron microscopy images of CAB-1 at 1 mM at pH 7.4 in water after aging for 24 hours, showing formation of supramolecular filaments. (28E) Circular dichroism spectrum of CAB-1 filaments, indicating β-sheet character by presence of negative peak around 218 nm. CGNNQQGGDPVKG (SEQ ID NO: 17).
Figures 29A, 29B, 29C, 29D, 29E:
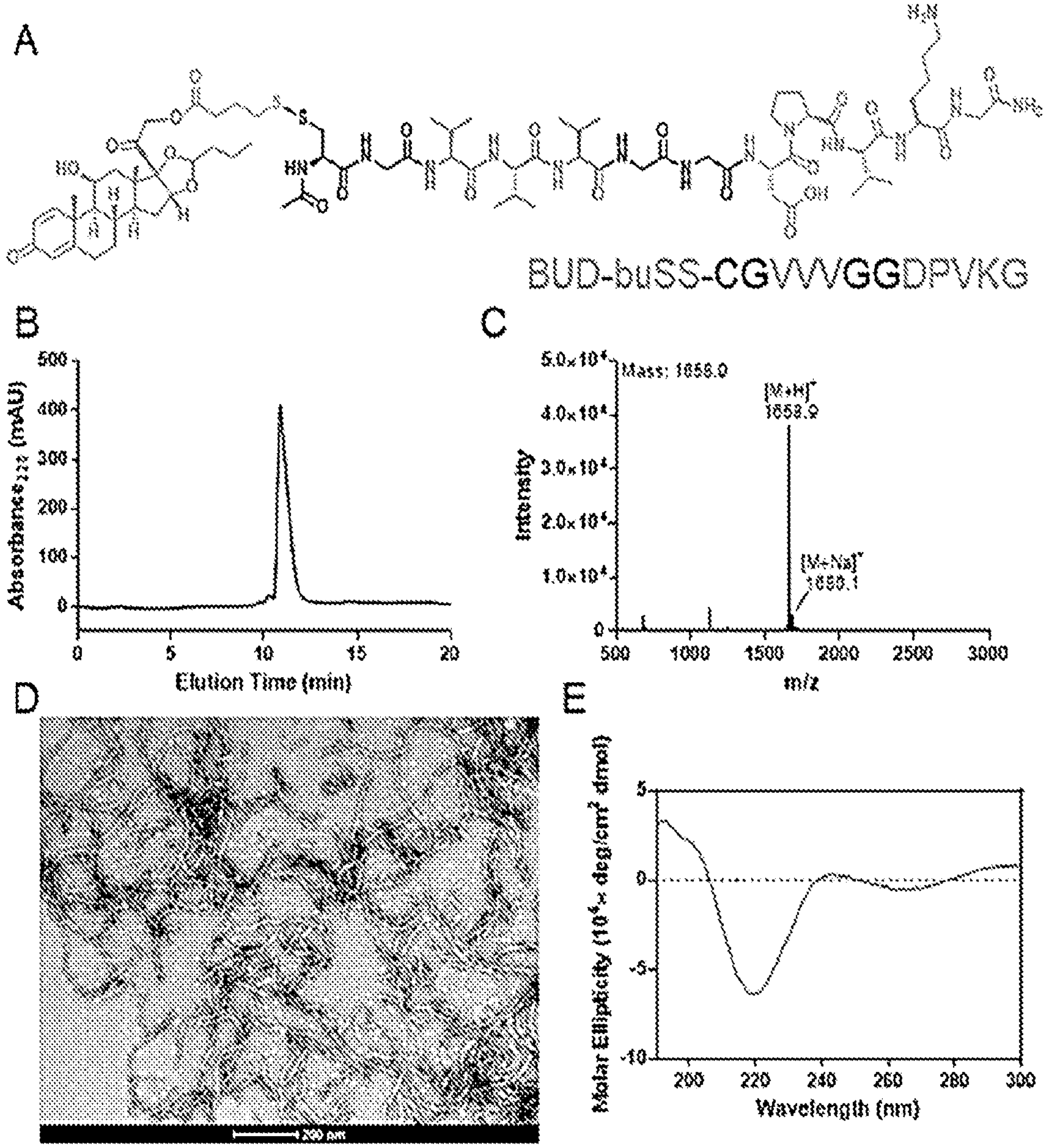
FIGS. 29A-29E: (29A) Chemical structure of budesonide-based drug amphiphile CAB-2, where molecular design is composed of hydrophobic drug budesonide (red) and a hydrophilic peptide, which contains a β-sheet regulating sequence (blue) to promote formation of 1D nanostructures and an anti-inflammatory sequence (pink) to enhance anti-inflammatory efficacy. (29B) Analytical RP-HPLC chromatogram of CAB-2, showing high purity after synthesis. (29C) MALDI-TOF mass spectrum of purified CAB-2, confirming correct molecular weight. (29D) Representative transmission electron microscopy images of CAB-2 at 1 mM at pH 7.4 in water after aging for 24 hours, showing formation of supramolecular filaments. (29E) Circular dichroism spectrum of CAB-2 filaments, indicating β-sheet character by presence of negative peak around 220 nm. CGVVVGGDPVKG (SEQ ID NO: 18).
Figures 30A, 30B, 30C, 30D:
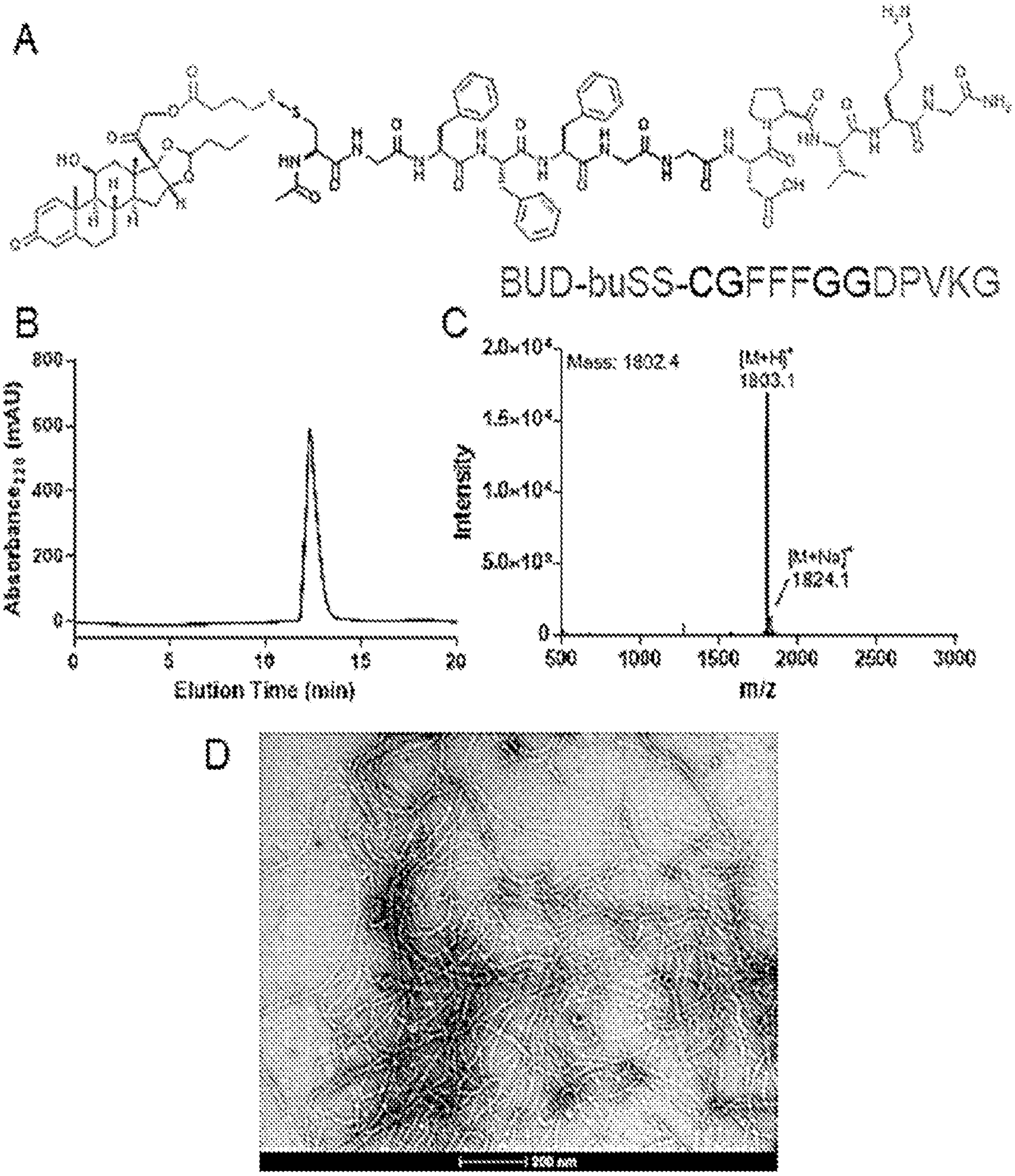
Figures 31A, 31B, 31C, 31D, 31E:
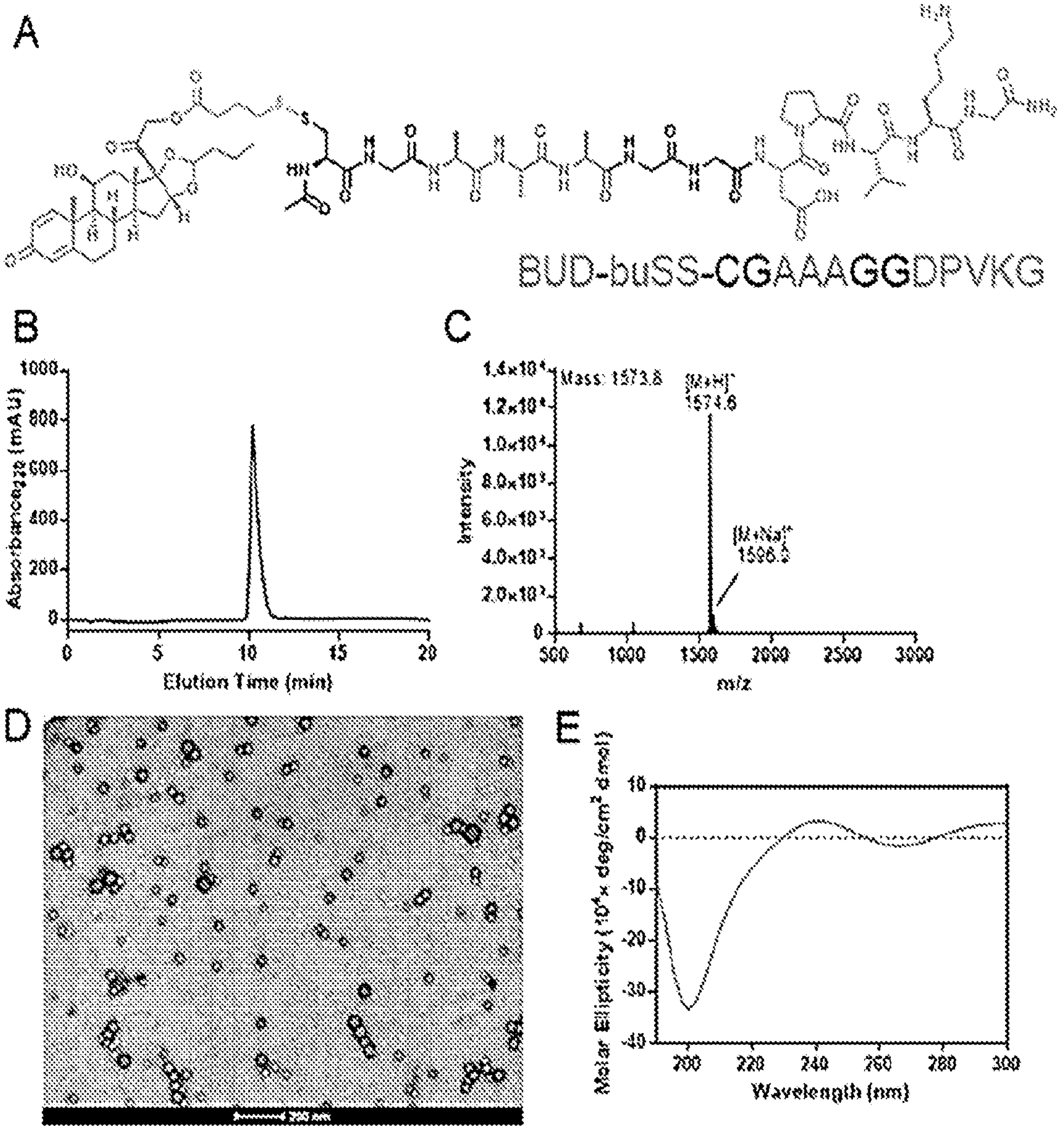
FIGS. 31A-31E: (31A) Chemical structure of budesonide-based drug amphiphile CAB-4, where molecular design is composed of hydrophobic drug budesonide (red) and a hydrophilic peptide, which contains a non-β-sheet regulating sequence (blue) to promote formation of OD nanostructures and an anti-inflammatory sequence (pink) to enhance anti-inflammatory efficacy. (31B) Analytical RP-HPLC chromatogram of CAB-4, showing high purity after synthesis. (31C) MALDI-TOF mass spectrum of purified CAB-4, confirming correct molecular weight. (31D) Representative transmission electron microscopy images of CAB-4 at 2 mM at pH 7.4 in water after aging for 24 hours, showing formation of supramolecular spherical particles and micelles. (31E) Circular dichroism spectrum of CAB-4 filaments, indicating random coil character by presence of negative peak around 200 nm. CGAAAGGDPVKG (SEQ ID NO: 20).
Figure 32A:
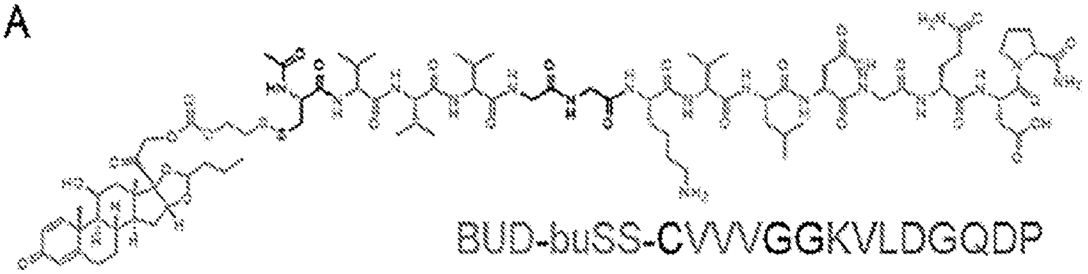
FIGS. 32A-32D: (32A) Chemical structure of budesonide-based drug amphiphile CAB-0 (a prototype design), where molecular design is composed of hydrophobic drug budesonide (red) and a hydrophilic peptide, which contains a β-sheet regulating sequence (blue) to promote formation of 1D nanostructures and an anti-inflammatory sequence (pink) to enhance anti-inflammatory efficacy. (32B) Analytical RP-HPLC chromatogram of CAB-0, showing high purity after synthesis. (32C) MALDI-TOF mass spectrum of purified CAB-0, confirming correct molecular weight. (32D) Representative transmission electron microscopy images of CAB-0 at 500 μM at pH 7.4 in water after aging for 24 hours, showing formation of supramolecular filaments (left) and retention of filaments after a nebulization event with shortened length (right). CVVVGGKVLDGQDP (SEQ ID NO: 9).
Figure 32B:
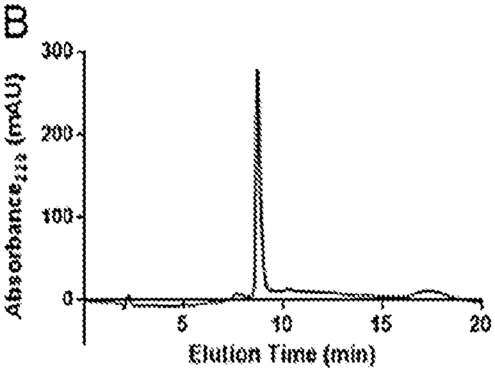
Figure 32C:
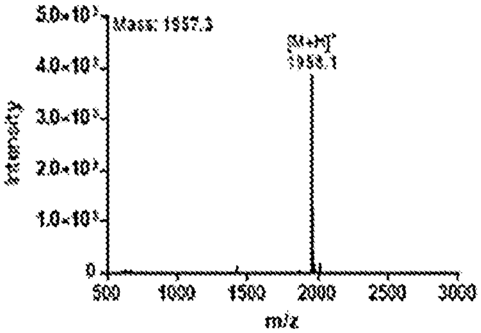
Figure 32D:
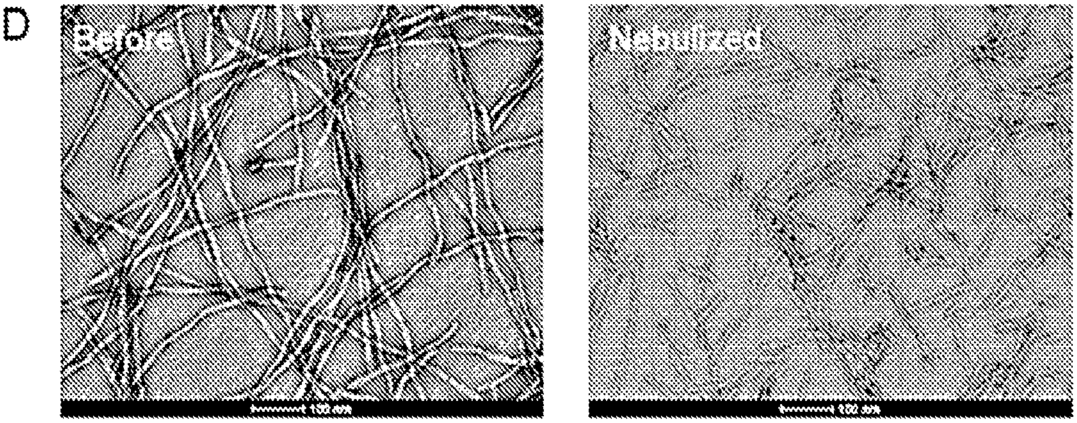

We also examined the release pattern and output rate of the loaded KPA filaments to ascertain if drug/dye encapsulation would influence release pattern. We nebulized PTX-, Cou6-, and BUD-loaded KPA filaments (1 mM KPA, 3 mL) for 10 min and analyzed fluid loss and remaining drug concentration within the device over the course of a 10 min nebulization event. As shown in FIG. 24E, the encapsulated drugs/dye are released linearly from the jet nebulizer. The total percentage of fluid released roughly estimated 70%, whereas the total percentage of drug/dye released averaged around 60-70%, as shown in FIG. 25. While drug concentration is likely to increase with evaporation of water from aerosol droplets as they travel through air, the lower drug/dye output compared to fluid suggests that also the concentration of drug/dye (and thereby their PA carrier) varies from droplet to droplet, and thus filament output deviates slightly from homogeneity over the course of a nebulization event. The output rates of the encapsulated molecules (μg/min) are compared in FIG. 24F. The rates of Cou6 and BUD are comparable but higher than PTX, which is reflective of their differences in loading capacity within the KPA filaments (FIG. 20B). Therefore, by tuning the drug loading through adjustments in the molecular design of the PA molecules, we can influence the delivery rate of encapsulated drugs and dyes in liquid aerosols from a nebulizer device.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A molecule having a general formula H-L1-Pep-L2-C, wherein:

H is a biologically active agent;

Pep is CGNNQQ (SEQ ID NO: 5);

L1 is a C1-C6 acyl sulfhydryl, wherein the sulfhydryl of L1 and the sulfhydryl in the cysteine residue of Pep form a disulfide bond;

L2 is a linker consisting of an amino acid or a peptide of 2 to 4 amino acids; and C is DPVKG (SEQ ID NO: 15).

2. The molecule of claim 1, wherein H comprises budesonide or paclitaxel.

3. The molecule of claim 1, wherein Pep-L2-C is CGNNQQGGDPVKG (SEQ ID NO: 17).

4. The molecule of claim 1, comprising a molecule having a structure of:

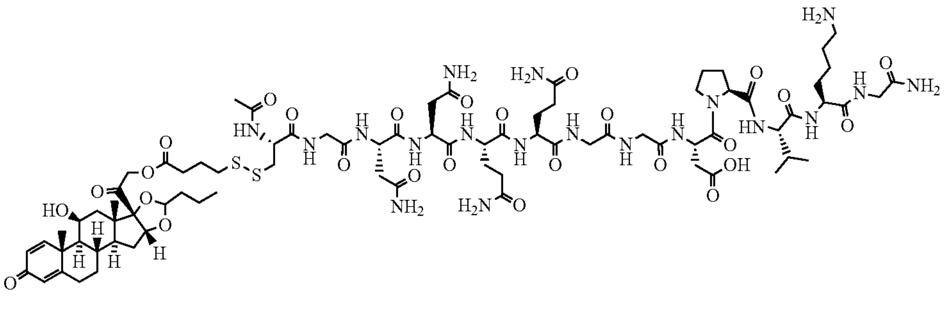

wherein CGNNQQGGDPVKG is SEQ ID NO: 17.

5. A supramolecular filament composition comprising the molecule of claim 1.

6. The supramolecular filament composition of claim 5, formulated for delivery to a lung as an inhalable spray or aerosol.

7. The molecule of claim 1, wherein the biologically active agent is a hydrophobic biologically active agent.

8. The molecule of claim 1, wherein the biologically active agent is a drug.

* * * * *

SEQUENCE LISTING

```
<160> NUMBER OF SEQ ID NOS: 23

<210> SEQ ID NO 1
<211> LENGTH: 4
<212> TYPE: PRT
<213> ORGANISM: Artificial Sequence
<220> FEATURE:
<223> OTHER INFORMATION: Synthetic sequence

<400> SEQUENCE: 1

Tyr Val Val Val
1


<210> SEQ ID NO 2
<211> LENGTH: 9
<212> TYPE: PRT
<213> ORGANISM: Artificial Sequence
<220> FEATURE:
<223> OTHER INFORMATION: Synthetic sequence

<400> SEQUENCE: 2

Tyr Val Val Val Gly Gly Glu Glu Glu
1               5


<210> SEQ ID NO 3
<211> LENGTH: 8
<212> TYPE: PRT
<213> ORGANISM: Artificial Sequence
<220> FEATURE:
<223> OTHER INFORMATION: Synthetic sequence

<400> SEQUENCE: 3

Tyr Val Val Val Gly Gly Lys Lys
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Synthetic sequence

<400> SEQUENCE: 4

Tyr Val Val Val Gly Gly Lys Lys Lys
1               5


<210> SEQ ID NO 5
<211> LENGTH: 6
<212> TYPE: PRT
<213> ORGANISM: Artificial Sequence
<220> FEATURE:
<223> OTHER INFORMATION: synthetic sequence

<400> SEQUENCE: 5

Cys Gly Asn Asn Gln Gln
1               5


<210> SEQ ID NO 6
<211> LENGTH: 9
<212> TYPE: PRT
<213> ORGANISM: Artificial Sequence
<220> FEATURE:
<223> OTHER INFORMATION: synthetic sequence

<400> SEQUENCE: 6

Cys Gly Asn Asn Gln Gln Lys Lys Lys
1               5


<210> SEQ ID NO 7
<211> LENGTH: 4
<212> TYPE: PRT
<213> ORGANISM: Artificial Sequence
<220> FEATURE:
<223> OTHER INFORMATION: synthetic sequence

<400> SEQUENCE: 7

Cys Val Val Val
1


<210> SEQ ID NO 8
<211> LENGTH: 8
<212> TYPE: PRT
<213> ORGANISM: Artificial Sequence
<220> FEATURE:
<223> OTHER INFORMATION: synthetic sequence

<400> SEQUENCE: 8

Lys Val Leu Asp Gly Gln Asp Pro
1               5


<210> SEQ ID NO 9
<211> LENGTH: 14
<212> TYPE: PRT
<213> ORGANISM: Artificial Sequence
<220> FEATURE:
<223> OTHER INFORMATION: synthetic sequence

<400> SEQUENCE: 9

Cys Val Val Val Gly Gly Lys Val Leu Asp Gly Gln Asp Pro
1               5                   10


<210> SEQ ID NO 10
```

<211> LENGTH: 6
<212> TYPE: PRT
<213> ORGANISM: Artificial Sequence
<220> FEATURE:
<223> OTHER INFORMATION: synthetic sequence

<400> SEQUENCE: 10

Cys Gly Gly Val Val Val
1 5

<210> SEQ ID NO 11
<211> LENGTH: 9
<212> TYPE: PRT
<213> ORGANISM: Artificial Sequence
<220> FEATURE:
<223> OTHER INFORMATION: synthetic sequence

<400> SEQUENCE: 11

Cys Gly Gly Val Val Val Gly Gly Lys
1 5

<210> SEQ ID NO 12
<211> LENGTH: 10
<212> TYPE: PRT
<213> ORGANISM: Artificial Sequence
<220> FEATURE:
<223> OTHER INFORMATION: synthetic sequence

<400> SEQUENCE: 12

Gln His Trp Ser Tyr Gly Leu Arg Pro Gly
1 5 10

<210> SEQ ID NO 13
<211> LENGTH: 13
<212> TYPE: PRT
<213> ORGANISM: Artificial Sequence
<220> FEATURE:
<223> OTHER INFORMATION: synthetic sequence

<400> SEQUENCE: 13

Cys Gly Gly Gln His Trp Ser Tyr Gly Leu Arg Pro Gly
1 5 10

<210> SEQ ID NO 14
<211> LENGTH: 8
<212> TYPE: PRT
<213> ORGANISM: Artificial Sequence
<220> FEATURE:
<223> OTHER INFORMATION: synthetic sequence

<400> SEQUENCE: 14

Lys Val Leu Asp Pro Val Lys Gly
1 5

<210> SEQ ID NO 15
<211> LENGTH: 5
<212> TYPE: PRT
<213> ORGANISM: Artificial Sequence
<220> FEATURE:
<223> OTHER INFORMATION: synthetic sequence

<400> SEQUENCE: 15

Asp Pro Val Lys Gly
1 5

<210> SEQ ID NO 16
<211> LENGTH: 4

<212> TYPE: PRT
<213> ORGANISM: Artificial Sequence
<220> FEATURE:
<223> OTHER INFORMATION: synthetic sequence

<400> SEQUENCE: 16

Asn Asn Gln Gln
1

<210> SEQ ID NO 17
<211> LENGTH: 13
<212> TYPE: PRT
<213> ORGANISM: Artificial Sequence
<220> FEATURE:
<223> OTHER INFORMATION: synthetic sequence

<400> SEQUENCE: 17

Cys Gly Asn Asn Gln Gln Gly Gly Asp Pro Val Lys Gly
1 5 10

<210> SEQ ID NO 18
<211> LENGTH: 12
<212> TYPE: PRT
<213> ORGANISM: Artificial Sequence
<220> FEATURE:
<223> OTHER INFORMATION: synthetic sequence

<400> SEQUENCE: 18

Cys Gly Val Val Val Gly Gly Asp Pro Val Lys Gly
1 5 10

<210> SEQ ID NO 19
<211> LENGTH: 12
<212> TYPE: PRT
<213> ORGANISM: Artificial Sequence
<220> FEATURE:
<223> OTHER INFORMATION: synthetic sequence

<400> SEQUENCE: 19

Cys Gly Phe Phe Phe Gly Gly Asp Pro Val Lys Gly
1 5 10

<210> SEQ ID NO 20
<211> LENGTH: 12
<212> TYPE: PRT
<213> ORGANISM: Artificial Sequence
<220> FEATURE:
<223> OTHER INFORMATION: synthetic sequence

<400> SEQUENCE: 20

Cys Gly Ala Ala Ala Gly Gly Asp Pro Val Lys Gly
1 5 10

<210> SEQ ID NO 21
<211> LENGTH: 14
<212> TYPE: PRT
<213> ORGANISM: Artificial Sequence
<220> FEATURE:
<223> OTHER INFORMATION: synthetic sequence

<400> SEQUENCE: 21

Cys Val Val Val Gly Gly Lys Val Leu Asp Gly Gln Asp Pro
1 5 10

<210> SEQ ID NO 22
<211> LENGTH: 10
<212> TYPE: PRT

-continued

```
<213> ORGANISM: Artificial Sequence
<220> FEATURE:
<223> OTHER INFORMATION: synthetic sequence

<400> SEQUENCE: 22

Cys Gly Asn Asn Gln Gln Gly Gly Lys Lys
1               5                   10


<210> SEQ ID NO 23
<211> LENGTH: 8
<212> TYPE: PRT
<213> ORGANISM: Artificial Sequence
<220> FEATURE:
<223> OTHER INFORMATION: synthetic sequence

<400> SEQUENCE: 23

Cys Gly Ala Ala Ala Lys Lys Lys
1               5
```